(12) United States Patent
Chodavarapu et al.

(10) Patent No.: US 12,667,545 B2
(45) Date of Patent: *Jun. 30, 2026

(54) LYOPHILIZED COMPOSITIONS OF PHENOBARBITAL SODIUM SALT

(71) Applicant: Nivagen Pharmaceuticals, Inc., Sacramento, CA (US)

(72) Inventors: Bala Tripura Sundari Chodavarapu, Davis, CA (US); Thirupathi Mangali, Sacramento, CA (US); Jay Shukla, Sacramento, CA (US); Anand Shukla, Denver, CO (US); Dasaradhi Lakkaraju, Sacramento, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 895 days.

This patent is subject to a terminal disclaimer.

(21) Appl. No.: 17/854,914

(22) Filed: Jun. 30, 2022

(65) Prior Publication Data

US 2022/0354794 A1 Nov. 10, 2022

Related U.S. Application Data

(63) Continuation-in-part of application No. 17/025,881, filed on Sep. 18, 2020, now Pat. No. 11,406,598.

(60) Provisional application No. 62/903,511, filed on Sep. 20, 2019.

(51) Int. Cl.
| | |
|---|---|
| *A61K 9/16* | (2006.01) |
| *A61K 9/19* | (2006.01) |
| *A61K 31/515* | (2006.01) |
| *A61K 47/02* | (2006.01) |

(52) U.S. Cl.
CPC .............. *A61K 9/19* (2013.01); *A61K 31/515* (2013.01); *A61K 47/02* (2013.01)

(58) Field of Classification Search
CPC ........ A61K 9/19; A61K 31/515; A61K 47/02; A61K 9/0019
See application file for complete search history.

(56) References Cited

U.S. PATENT DOCUMENTS

| | | | |
|---|---|---|---|
| 6,077,545 A | 6/2000 | Roskos et al. | |
| 9,138,456 B2 | 9/2015 | O'Connor et al. | |
| 11,406,598 B2 * | 8/2022 | Chodavarapu | ............ A61P 1/00 |

(Continued)

FOREIGN PATENT DOCUMENTS

| | | |
|---|---|---|
| CN | 104940149 A | 9/2015 |
| WO | 2017085687 A1 | 5/2017 |

OTHER PUBLICATIONS

An Internet Archive capture of Lynne Kelly, Phenobarbital sodium, Critical Care Trauma Centre (2018).

(Continued)

*Primary Examiner* — Carlos A Azpuru
(74) *Attorney, Agent, or Firm* — Martin Fessenmaier; Umberg Zipser LLP

(57) ABSTRACT

A composition of, method for producing, and use of an amorphous lyophilized Phenobarbital Sodium having high purity are presented. The amorphous lyophilized Phenobarbital Sodium is storage-stable being essentially void of impurities (e.g., phenyl ethylacetylurea (PEAU), 2-ethyl-2-phenylmalonamide (2EPMM), and/or alpha-phenylbutyrylguanidine (PBG)) upon reconstitution in water.

20 Claims, 39 Drawing Sheets

(56) References Cited

U.S. PATENT DOCUMENTS

| | | | |
|---|---|---|---|
| 11,878,076 B2 * | 1/2024 | Chodavarapu ....... | A61K 31/515 |
| 2010/0035904 A1 | 2/2010 | Sun et al. | |
| 2017/0143719 A1 * | 5/2017 | Parker ................. | A61K 31/515 |
| 2021/0085608 A1 | 3/2021 | Chodavarapu et al. | |

OTHER PUBLICATIONS

Annex 10: Stability testing of active pharmaceutical ingredients and finished pharmaceutical products, in Who Technical Report Series No. 1010, World Health Organization 309-51 (2018).

Declaration of Raj Suryanarayanan, Ph.D. for Inter Partes Review of U.S. Pat. No. 11,878,076.

Dejan S. Przic et al., Lyophilization—The Process and Industrial Use, 58(12) Chem. Ind. 552 (2004).

Duncan Q.M. Craig et al., The relevance of the amorphous state to pharmaceutical dosage forms: glassy drugs and freeze dried systems, 179 Int. J. Pharm. 179 (1999).

Excerpts of USP 40—NF 35: The United States Pharmacopeia and National Formulary vol. 1, U.S. Pharmacopeial Convention (2017).

Freeze-Drying/Lyophilization of Pharmaceutical and Biological Products (2010).

Guidance for Industry Q1A(R2) Stability Testing of New Drug Substances and Products, U.S. FDA (Nov. 2003).

ICH Topic Q1A Stability Testing Guidelines: Stability Testing of New Drug Substances and Products—Step 5, CPMP/ICH/380/95, EMEA (1995).

Bardat et al., "Moisture Measurement: A New Method for Monitoring Freeze-drying Cycles," Journal of Parenteral Science & Technology, Nov.-Dec. 1993; 47(6):293-299.

Dietz et al., "Phenobarbital Stability in Different Dosage Forms: Alternatives for Elixirs, " Pharmaceutical Research, 1988; 5(12):803-805.

FDA, "Lyophilization of Parenteral: Guide to Inspections of Lyophilization of Parenterals," published Nov. 11, 2014; 22 pgs.

Gupta, V. Das, "Effect of Ethanol, Glycerol, and Propylene Glycol on the Stability of Phenobarbital Sodium," Journal of Pharmaceutical Sciences, Nov. 1, 1984; 73(11):1661-1662. Abstract only.

Jatul, Bernard B., "The Stability of Solutions of Phenobarbital Sodium," A Dissertation Presented to the Graduate Council of the University of Florida, Feb. 1943; 170 pgs.

Kelly et al., "Phenobarbital Sodium," London Health Sciences Centre; Last Update: Oct. 11, 2018; 4 pgs. Retrieved from the internet on Nov. 18, 2020: https://www.Ihsc.on.ca/critical-care-trauma-centre/phenobarbital-sodium.

Nahata et al., "Stability of phenobarbital sodium diluted in 0.9% sodium chloride injection," American Journal of Hospital Pharmacy, Feb. 1986; 43:384-385.

Nayyar et al., "Phenytoin-Folate Interactions: How Far is Safe Folate Supplementation in Phenytoin Treated Epileptic Patients?" Journal of Applied Pharmaceutical Science, 2012; 02(06):230-235.

Snyder, Meg, "Lyophilization: The Basics—Drug Discovery and Development," Mar. 7, 2017; pp. 1-5. Retrieved from the internet on Nov. 19, 2020: https://www.drugdiscoverytrends.com/lyophilization-the-basics/#:~:text=Some of the advantages of,to heat the product excessively.

Staudt, "Phenobarbital in newborn infants: Overview," Monatsschr Kinderheilkd, Apr. 1984; 132(4):194-202. Abstract only.

Jane D. Siegel et al., 2007 guideline for isolation precautions: preventing transmission of infectious agents in health care settings, 35 Am. J. Infect. Control S65-164 (2007).

Joanne Broadhead, Parenteral Dosage Forms, in Pharmaceutical Preformulation and Formulation: A Practical Guide From Candidate Drug Selection To Commercial Dosage Form 331 (Mark Gibson ed., 2001).

Joel Bernstein, Polymorphism in Molecular Crystals (2002).

John K. Haleblian, Characterization of Habits and Crystalline Modification of Solids and Their Pharmaceutical Applications, 64(8) J. Pharm. Sci. 1269 (1975).

Jumpei Saito et al., Potentially Harmful Excipients in Neonatal Medications: An Observational and Cross-Regional Comparison of Japan and Europe, 4(2) Neonat. Pediatr. Med. 172 (2018).

Kou Kawada et al., A Clinical Trial Assessing the Efficacy and Safety of a New Injectable Formula of Sodium Phenobarbital Containing No Additives for the Treatment of Neonatal Seizures, 42(4) Jpn. J. Clin. Pharmacol. Ther. 205 (2011).

Lian Yu, Amorphous pharmaceutical solids: preparation, characterization and stabilization, 48 Adv. Drug Deliv. Rev. 27 (2001).

Lyophilization of Parenteral (7/93): Guide to Inspections of Lyophilization of Parenterals, U.S. Food and Drug Administration (1993).

Meg Snyder, Lyophilization: The basics, Drug Discovery & Development (2017).

Michael J. Pikal, Freeze Drying, in Encyclopedia of Pharmaceutical Technology vol. 1, 1807-33 (2007).

Nancy J. Dietz et al., Phenobarbital Stability in Different Dosage Forms: Alternatives for Elixirs, 5(12) Pharm. Res. 803 (1988).

Neal G. Anderson, Practical Process Research & Development (2000).

Neal G. Anderson, Practical Process Research & Development (2012).

Pharmaceutical Interview Form, Nobelpharma Co. (Jul. 2010).

Phenobarbital Sodium—phenobarbital sodium injection, Dailymed (Aug. 2011).

Polymorphism in Pharmaceutical Solids (1999).

Pradip Hiwale et al., Variables Affecting Reconstitution Time of Dry Powder for Injection, Pharmaceutical Technology 32(7) (Jul. 2, 2008).

Sakthivel Lakshmana Prabu & T.N.K. Suriyaprakash, Impurities and Its Importance in Pharmacy, 3(2) Int. J. Pharm. Sci. Rev. Res. 66 (2010).

Selection of the Appropriate Package Type Terms and Recommendations for Labeling Injectable Medical Products Packaged in Multiple-Dose, Single-Dose, and Single-Patient-Use Containers for Human Use Guidance for Industry, U. S. Food and Drug Administration (Oct. 2018).

Sun Hee Kim et al., Physicochemical Stability of Reconstituted Decitabine (Dacogen®) Solutions and Ready-to-Administer Infusion Bags when Stored Refrigerated or Frozen, 2(4) Pharm. Technol. Hosp. Pharm. 145 (2017).

Takuya Iwamoto et al., Performance evaluation of the compounding robot, APOTECAchemo, for injectable anticancer drugs in a Japanese hospital, J. Pharm. Health Care Sci. 3(12) (2017).

TomažEinfalt et al., Methods of amorphization and investigation of the amorphous state, 63 Acta Pharm. 305 (2013).

Assignment abstract of title for U.S. Appl. No. 18/100,804, retrieved on Feb. 4, 2025; 1 page.

Declaration of Raj Suryanarayanan, Ph.D. for Inter Partes Review of U.S. Pat. No. 11,878,076 dated Apr. 12, 2025; 177 pgs.

Declaration of Tanya Zeif of Internet Archive dated Dec. 31, 2024 and URL https://web.archive.org/web/20110313193709/http://www.nobelpharma.co.jp:80/medical/pdf/Nobelbar/interviewform.pdf; 48 pages.

Declaration of Tanya Zeif of Internet Archive dated Jan. 3, 2025 and URL https://web.archive.org/web/20151004050809/http://dailymed.nlm.nih.gov/dailymed/drugInfo.cfm?setid=ffcaa218-ed6a-4557-9645-b9a91128a214; 15 pages.

Defendants' Motion To Dismiss for Improper Venue Or, in the Alternative, Transfer dated Jun. 24, 2024; 29 pages.

File History of U.S. Appl. No. 17/854,914—"Lyophilized Compositions of Phenobarbital Sodium Salt," compiled on Feb. 5, 2025; 182 pages.

File History of U.S. Pat. No. 11,406,598—"Lyophilized compositions of phenobarbital sodium salt," compiled on Feb. 13, 2025; 1285 pages.

File History of U.S. Pat. No. 11,878,076—"Lyophilized compositions of phenobarbital sodium salt," compiled on Feb. 5, 2025; 367 pages.

File History of U.S. Appl. No. 62/903,511—"Lyophilized Compositions of Phenobarbital Sodium Salt," compiled on Feb. 5, 2025; 133 pages.

Petition for Inter Partes Review of U.S. Pat. No. 11,878,076 dated Apr. 22, 2005; 96 pgs.

(56)                    References Cited

OTHER PUBLICATIONS

Translation Certification of https://web.archive.org/web/
20110313193709/http:/www.nobelpharma.co.jp:80/medical/pdf/
Nobelbar/interviewform.pdf dated Dec. 23, 2024; 1 page.

* cited by examiner

SampleName Blank                    Result Id 16563

| | Peak Name | RT | Area | s/n | USP Plate Count | USP Tailing |
|---|---|---|---|---|---|---|
| 1 | Phenobarbital | 4.597 | 9769 | 1054.848570 | 7861.1 | 1.1 |

| | PeakName | RT | Area | Amount | s/n | USP Plate Count | USP Tailing |
|---|---|---|---|---|---|---|---|
| 1 | Phenobarbital | 4.597 | 38614 | 0.001 | 2906.846635 | 7746.3 | 1.2 |

SampleName 2EPMM imp          Result Id 6572

| | PeakName | RT | Area | % Area | s/n | USP Plate Count | USP Tailing | Purity Angle | Purity Threshold |
|---|---|---|---|---|---|---|---|---|---|
| 1 | 2EPMM | 2.119 | 18797 | 100.00 | 1472 | 10573.6 | 1.2 | 0.674 | 1.633 |

—— SampleName PBG imp                    Result Id 6573

| | PeakName | RT | Area | % Area | s/n | USP Plate Count | USP Tailing | Purity/Angle | Purity/Threshold |
|---|---|---|---|---|---|---|---|---|---|
| 1 | PBG | 3.350 | 41778 | 100.00 | 2090 | 86019 | 1.5 | 21.848 | 62.982 |

—— SampleName PEAU_0.2%; Channel Description W2489 ChA 210nm; Result Id 28698

—— SampleName Assay W_STD                Result Id 16442

| | PeakName | RT | Area | Amount | s/n | USP Plate Count | USP Tailing |
|---|---|---|---|---|---|---|---|
| 1 | Phenobarbital | 4.582 | 897147 | 0.476 | 5094.058185 | 7493.0 | 1.2 |

SampleName RLD_058407_65 mg/mL　　　Result Id 2485

| | Peak Name | RT | Area | Amount | USP Resolution | USP Plate Count | USP Tailing | Assay |
|---|---|---|---|---|---|---|---|---|
| 1 | Phenobarbital | 10.130 | 2396458 | 60.823 | 17.9 | 17534.1 | 1.0 | 112.1 |

| | Peak Name | RT | Area | % Area | Amount | Units | Assay | USP Resolution | USP Tailing |
|---|---|---|---|---|---|---|---|---|---|
| 1 | Benzyl Alcohol | 3.391 | 87091 | 10.96 | 14.994 | mg/mL | 105.2 | 23.7 | 1.7 |
| 2 | Blank | 1.356 | 828 | 0.10 | 0.068 | mg/mL | | | 1.0 |
| 3 | Phenobarbital | 4.537 | 697184 | 87.71 | 57.200 | mg/mL | 96.3 | 7.2 | 1.5 |
| 4 | RRT_1.82 | 8.319 | 9745 | 1.23 | 0.800 | mg/mL | | 15.0 | 1.3 |

| | Peak Name | RT | Area | % Area | Amount | Units | Assay | USP Resolution | USP Tailing |
|---|---|---|---|---|---|---|---|---|---|
| 1 | Benzyl Alcohol | 3.392 | 84435 | 11.25 | 14.537 | mg/mL | 102.0 | 23.7 | 1.7 |
| 2 | Blank | 1.357 | 798 | 0.11 | 0.065 | mg/mL | | | 1.1 |
| 3 | Phenobarbital | 4.536 | 627538 | 83.64 | 51.486 | mg/mL | 86.7 | 7.2 | 1.5 |
| 4 | RRT_1.82 | 8.321 | 37484 | 5.00 | 3.075 | mg/mL | | 14.6 | 1.2 |

—— SampleName RLD_058407_65 mg/mL; Channel Description 2998 (205-400)nm; Result Id 3537

| | PeakName | RT | Area | % Area | USP Resolution | s/n | USP Plate Count | USP Tailing |
|---|---|---|---|---|---|---|---|---|
| 1 | Benzyl alcohol | 3.855 | 4623585 | 21.07 | 17.1 | 390.1 | 12312.8 | 1.5 |
| 2 | Pheno_Impurity A | 1.829 | 2803 | 0.01 | 5.2 | 0.3 | 7608.2 | 1.6 |
| 3 | Phenobarbital | 5.238 | 17188084 | 78.32 | 8.0 | 1018.9 | 11238.0 | 1.4 |
| 4 | RRT_1.867_Pheno degrdnproudct | 9.781 | 92287 | 0.42 | 16.5 | 3.5 | 13191.8 | 1.2 |

— SampleName RLD 65 mg_RT_6M; Result Id 24718; Channel Name 210.0nm

| | Peak Name | RT | Area | % Area | Amount | Units | USP Resolution | USP Tailing |
|---|---|---|---|---|---|---|---|---|
| 1 | Benzyl Alcohol | 3.391 | 3972837 | 21.25 | 16.272 | mg/mL | 13.8 | 1.7 |
| 2 | Phenobarbital | 4.537 | 14515521 | 77.64 | 56.435 | mg/mL | 7.1 | 1.5 |
| 3 | RRT_1.82 | 8.321 | 200110 | 1.07 | 0.778 | mg/mL | 14.6 | 1.3 |

Sample Name RLD 65 mg_ACC_6M ; Result Id 24719; Channel Name 210.0nm

| | Peak Name | RT | Area | % Area | Amount | Units | USP Resolution | USP Tailing |
|---|---|---|---|---|---|---|---|---|
| 1 | Benzyl Alcohol | 3.392 | 3833550 | 21.50 | 15.701 | mg/mL | 12.8 | 1.7 |
| 2 | Phenobarbital | 4.536 | 13183528 | 73.94 | 51.257 | mg/mL | 7.1 | 1.5 |
| 3 | RRT_1.82 | 8.321 | 762556 | 4.28 | 2.965 | mg/mL | 14.6 | 1.3 |
| 4 | RRT_1.949 | 9.000 | 42716 | 0.24 | 0.166 | mg/mL | 1.9 | 1.3 |

| | Peak Name | RT | Area | Amount | USP Resolution | USP Plate Count | USP Tailing | Assay |
|---|---|---|---|---|---|---|---|---|
| 1 | Phenobarbital | 10.131 | 2358542 | 119.721 | 17.9 | 17563.1 | 1.0 | 110.3 |

| | Peak Name | RT | Area | % Area | Amount | Units | Assay | USP Resolution | USP Tailing |
|---|---|---|---|---|---|---|---|---|---|
| 1 | Benzyl Alcohol | 3.391 | 43232 | 5.84 | 14.886 | mg/mL | 104.5 | | 1.7 |
| 2 | Phenobarbital | 4.535 | 688747 | 93.10 | 113.015 | mg/mL | 95.2 | 7.2 | 1.5 |
| 3 | RRT_1.82 | 8.322 | 7837 | 1.06 | 1.286 | mg/mL | | 14.5 | 1.2 |

—— SampleName RLD 130 mg_ACC_6M; Result Id 24862; Channel Name 254.0nm

| | Peak Name | RT | Area | % Area | Amount | Units | Assay | USP Resolution | USP Tailing |
|---|---|---|---|---|---|---|---|---|---|
| 1 | Benzyl Alcohol | 3.391 | 43440 | 5.94 | 14.958 | mg/mL | 105.0 | | 1.7 |
| 2 | Phenobarbital | 4.537 | 657548 | 89.99 | 107.895 | mg/mL | 90.9 | 7.2 | 1.5 |
| 3 | RRT_1.82 | 8.323 | 29742 | 4.07 | 4.880 | mg/mL | | 14.6 | 1.2 |

──── SampleName RLD_058409_130 mg/mL; Channel Description 2998 (205-400)nm; Result Id 3539

| | Peak Name | RT | Area | % Area | USP Resolution | s/n | USP Plate Count | USP Tailing |
|---|---|---|---|---|---|---|---|---|
| 1 | Benzyl alcohol | 3853 | 2394223 | 11.87 | 20.8 | 2239 | 12438.0 | 1.5 |
| 2 | Phenobarbital | 5235 | 17661984 | 87.59 | 8.0 | 1144.4 | 11214.3 | 1.4 |
| 3 | RRT_1.867_Pheno degrd product | 9778 | 83640 | 0.41 | 16.6 | 3.5 | 13612.7 | 1.1 |

| | Peak Name | RT | Area | % Area | Amount | Units | USP Resolution | USP Tailing |
|---|---|---|---|---|---|---|---|---|
| 1 | Benzyl Alcohol | 3.391 | 1963213 | 11.91 | 16.081 | mg/mL | 13.4 | 1.7 |
| 2 | Phenobarbital | 4.535 | 14347574 | 87.06 | 111.565 | mg/mL | 7.1 | 1.5 |
| 3 | RRT_1.82 | 8.320 | 162620 | 0.99 | 1.265 | mg/mL | 14.6 | 1.3 |

— SampleName RLD 130 mg_ACC_6M; Result Id 24721; Channel Name 210.0nm

| | Peak Name | RT | Area | % Area | Amount | Units | USP Resolution | USP Tailing |
|---|---|---|---|---|---|---|---|---|
| 1 | Benzyl Alcohol | 3.391 | 1984788 | 12.10 | 16.258 | mg/mL | 12.8 | 1.7 |
| 2 | Phenobarbital | 4.536 | 13768702 | 83.93 | 107.064 | mg/mL | 7.1 | 1.5 |
| 3 | RRT_1.82 | 8.322 | 594916 | 3.63 | 4.626 | mg/mL | 14.6 | 1.2 |
| 4 | RRT_1.949 | 8.984 | 48228 | 0.29 | 0.375 | mg/mL | 1.8 | 1.3 |

SampleName #NPH1907_Lyo_65mg/mL_Initial; Channel Description W2489 ChB 254nm; Result Id 13991

| | Peak Name | RT | Area | Amount | Units | Assay | USP Resolution | s/n | USP Plate Count | USP Tailing |
|---|---|---|---|---|---|---|---|---|---|---|
| 1 | Phenobarbital | 4.706 | 887698 | 58.858 | mg/mL | 99.1 | 19.3 | 52343.5 | 7952.5 | 1.2 |
| 2 | Sodium | 1.153 | 3626 | | | | | 388.4 | 9439 | 1.1 |

—— SampleName NPH1907_65mg_RT_6M ; Channel Description W2489 ChB 254nm ; Result Id 31317

| | Peak Name | RT | Area | Amount | Units | Assay | USP Resolution | s/n | USP Plate Count | USP Tailing |
|---|---|---|---|---|---|---|---|---|---|---|
| 1 | Phenobarbital | 4.556 | 903872 | 59.328 | mg/mL | 100.0 | 20.8 | 44822.6 | 8704.0 | 1.1 |
| 2 | Sodium/Blank | 1.129 | 10057 | 0.661 | mg/mL | | | 616.7 | 1292.0 | 1.3 |

—— SampleName NPH1907_65mg_ACC_6M; Channel Description W2489 ChB 254nm; Result Id 31320

| | Peak Name | RT | Area | Amount | Units | Assay | USP Resolution | s/n | USP Plate Count | USP Tailing |
|---|---|---|---|---|---|---|---|---|---|---|
| 1 | Phenobarbital | 4.552 | 896990 | 58.956 | mg/mL | 99.3 | 21.1 | 48295.1 | 85733 | 1.1 |
| 2 | Sodium/Blank | 1.122 | 5564 | 0.366 | mg/mL | | | 364.9 | 1275.7 | 1.3 |

SampleName #NPH1907_Lyo_65mg/mL_Initial; Channel Description W2489 ChA 210nm; Result Id 14043

| | Peak Name | RT | Area | % Area | Amount | Units | USP Resolution | s/n | USP Plate Count | USP Tailing |
|---|---|---|---|---|---|---|---|---|---|---|
| 1 | Phenobarbital | 4.715 | 1814319 | 99.88 | 58.872 | mg/mL | 17.3 | 1073101.3 | 7604.1 | 1.2 |
| 2 | RRT_0.37 | 1.688 | 7980 | 0.04 | 0.026 | mg/mL | 37 | 772.4 | 28026 | 1.2 |
| 3 | Sodium | 1.158 | 13483 | 0.07 | 0.044 | mg/mL | | 1197.5 | 1039.2 | 1.2 |

SampleName NPH1907_65mg_RT_6M; Channel Description W2489 ChA 210nm; Result Id 31629

| | PeakName | RT | Area | % Area | Amount | Units | USP Resolution | s/n | USP Plate Count | USP Tailing |
|---|---|---|---|---|---|---|---|---|---|---|
| 1 | Blank2 | 1.384 | 4013 | 0.02 | | | 1.9 | 826.1 | 2241.7 | 1.1 |
| 2 | PEAU | 8.276 | 4512 | 0.02 | 0.013 | mg/mL | 14.8 | 278.0 | 12299.1 | 1.1 |
| 3 | Phenobarbital | 4.565 | 18206837 | 99.56 | 53.971 | mg/mL | 15.2 | 1516675.4 | 8239.9 | 1.1 |
| 4 | RRT_0.37 | 1.644 | 12808 | 0.07 | 0.038 | mg/mL | 1.9 | 1270.5 | 1640.7 | 1.1 |
| 5 | Sodium/Blank | 1.135 | 58253 | 0.32 | 0.173 | mg/mL | | 8406.1 | 1363.0 | 1.1 |

—— SampleName NPH1907_65mg_ACC_6M ; ChannelDescription W2489 ChA 210nm; Result Id 31632

| | Peak Name | RT | Area | % Area | Amount | Units | USP Resolution | s/n | USP Plate Count | USP Tailing |
|---|---|---|---|---|---|---|---|---|---|---|
| 1 | Blank2 | 1.361 | 5848 | 0.03 | | | 1.9 | 899.0 | 21439 | 1.0 |
| 2 | PEAU | 8.275 | 6741 | 0.04 | 0.020 | mg/mL | 14.6 | 427.7 | 11918.8 | 1.0 |
| 3 | Phenobarbital | 4.561 | 18093753 | 99.70 | 53.636 | mg/mL | 15.2 | 1583108.6 | 8445.9 | 1.1 |
| 4 | RRT_0.37 | 1.638 | 10466 | 0.06 | 0.031 | mg/mL | 1.9 | 1064.2 | 14825 | 1.1 |
| 5 | SodiumBlank | 1.123 | 32199 | 0.18 | 0.095 | mg/mL | | 4392.6 | 1362.2 | 1.1 |

SampleName #NPH1912_Lyo_130mg/mL_Initial; Channel Description W2489 ChB 254nm; Result Id 13996

| | Peak Name | RT | Area | Amount | Units | Assay | USP Resolution | s/n | USP Plate Count | USP Tailing |
|---|---|---|---|---|---|---|---|---|---|---|
| 1 | Phenobarbital | 4.704 | 880753 | 116.796 | mg/mL | 98.3 | 19.3 | 40192.1 | 7866.8 | 1.2 |
| 2 | Sodium | 1.151 | 2171 | | | | | 148.3 | 959.0 | 1.0 |

—— SampleName NPH1912_130mg_RT_6M; Channel Description W2489 ChB 254nm; Result Id 31325

| | Peak Name | RT | Area | Amount | Units | Assay | USP Resolution | s/n | USP Plate Count | USP Tailing |
|---|---|---|---|---|---|---|---|---|---|---|
| 1 | Phenobarbital | 4.564 | 905459 | 118.985 | mg/mL | 100.2 | 20.7 | 59858.2 | 8639.9 | 1.1 |
| 2 | Sodium/Blank | 1.133 | 4686 | 0.615 | mg/mL | | | 359.4 | 1362 | 1.4 |

—— SampleName NPH1912_130mg_ACC_6M ; Channel Description W2489 ChB 254nm; Result Id 31328

| | Peak Name | RT | Area | Amount | Units | Assay | s/n | USP Plate Count | USP Tailing |
|---|---|---|---|---|---|---|---|---|---|
| 1 | Phenobarbital | 4.562 | 896191 | 118.030 | mg/mL | 99.4 | 53755 | 8698.8 | 1.1 |

SampleName #NPH1912_Lyo_130mg/mL_Initial; Channel Description W2489 ChA 210nm; Result Id 14049

| | Peak Name | RT | Area | % Area | Amount | Units | USP Resolution | s/n | USP Plate Count | USP Tailing |
|---|---|---|---|---|---|---|---|---|---|---|
| 1 | Phenobarbital | 4.713 | 18027682 | 99.93 | 116.995 | mg/mL | 17.0 | 1301026.8 | 7849.3 | 1.2 |
| 2 | RRT_0.37 | 1.682 | 4819 | 0.03 | 0.031 | mg/mL | 3.6 | 423.7 | 2401.3 | 1.2 |
| 3 | Sodium | 1.156 | 7967 | 0.04 | 0.052 | mg/mL | | 849.1 | 941.5 | 1.1 |

—— SampleName NPH1912_130mg_RT_6M; Channel Description W2489 ChA 210nm; Result Id 31637

| | PeakName | RT | Area | % Area | Amount | Units | USP Resolution | s/n | USP Plate Count | USP Tailing |
|---|---|---|---|---|---|---|---|---|---|---|
| 1 | Blank2 | 1.366 | 1069 | 0.01 | | | 1.9 | 143.5 | 2247.2 | 1.1 |
| 2 | PEAU | 8.291 | 4082 | 0.02 | 0.024 | mg/mL | 14.8 | 213.9 | 12463.8 | 1.0 |
| 3 | Phenobarbital | 4.572 | 18248178 | 99.78 | 108.187 | mg/mL | 15.9 | 1373502.2 | 8426.5 | 1.1 |
| 4 | RRT_0.37 | 1.650 | 9642 | 0.05 | 0.057 | mg/mL | 2.0 | 832.7 | 1618.4 | 1.1 |
| 5 | SodiumBlank | 1.139 | 28215 | 0.15 | 0.167 | mg/mL | | 3439.2 | 1382.8 | 1.1 |

—— SampleName NPH1912_130mg_ACC_6M; Channel Description W2489 ChA 210nm; Result Id 31640

| | Peak Name | RT | Area | % Area | Amount | Units | USP Resolution | s/n | USP Plate Count | USP Tailing |
|---|---|---|---|---|---|---|---|---|---|---|
| 1 | Blank2 | 1.365 | 5461 | 0.03 | | | 1.9 | 827.2 | 2149.1 | 1.1 |
| 2 | PEAU | 8.292 | 5068 | 0.03 | 0.033 | mg/mL | 14.6 | 256.0 | 12326.6 | 1.0 |
| 3 | Phenobarbital | 4.570 | 18122566 | 99.73 | 107.442 | mg/mL | 15.1 | 1336868.2 | 6330.4 | 1.1 |
| 4 | RRT_0.37 | 1.646 | 9209 | 0.05 | 0.065 | mg/mL | 1.8 | 725.3 | 1481.9 | 1.1 |
| 5 | Sodium/Blank | 1.135 | 28641 | 0.16 | 0.171 | mg/mL | | 3440.5 | 1382.6 | 1.1 |

LYOPHILIZED COMPOSITIONS OF PHENOBARBITAL SODIUM SALT

RELATED APPLICATIONS

This application is a continuation-in-part application of our copending and allowed U.S. application with the Ser. No. 17/025,881, filed Sep. 18, 2020, which claims the benefit of U.S. Provisional Patent Application No. 62/903, 511, filed on Sep. 20, 2019, which is incorporated by reference in its entirety.

FIELD OF THE INVENTION

The present disclosure relates to compositions of storage-stable lyophilized Phenobarbital Sodium having high purity that are essentially void of impurities upon reconstitution in water.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Phenobarbital Sodium is a well-known barbiturate that is most commonly administered as an anti-convulsant for the treatment of seizures and may also be administered as a sedative, a sleep aide, or a pre-anesthetic. Phenobarbital Sodium is typically a liquid formulation administered intramuscularly (IM) or intravenously (IV) with crystalline granules or crystals dissolved in an aqueous solvent. For example, WO 2017/085687 to Parker et al. discloses a liquid formulation of Phenobarbital Sodium dissolved in water along with a C1-C4 alcohol and a glycol.

The stability of solubilized Phenobarbital Sodium has been a recurring problem because it readily hydrolyzes in water forming various degradation products. In particular, in water alone or in water with an increase in pH, Phenobarbital Sodium forms the degradation products phenylethylacetylurea (PEAU), 2-ethyl-2-phenylmalonamide (2EPMM), and alpha-phenylbutyrylguanidine (PBG). While these degradation impurities may not directly compromise the effectiveness of the Phenobarbital Sodium for its therapeutic activity, these degradation impurities are toxic and cause severe side effects. Specifically, PEAU was previously administered as Pheneturide for severely affected epileptics. However, the Food and Drug Administration (FDA) withdrew approval of Pheneturide due to its toxic effects. In particular, Pheneturide is reported to be a potent liver enzyme inducer that disrupts both calcium and folate metabolism. (Nayyar et al., 2012, *J. of Appl. Pharm Sci.,* 2:230-235.) Prior to its removal as an FDA-approved drug, patients treated with Pheneturide showed low levels of serum calcium and folate.

Over the years of medical administration, efforts have been made to decrease the formation of the toxic degradation products in the Phenobarbital Sodium liquid formulation. For example, Gupta, V. D., (*J. Pharm Sci.,* 1984, 73:1661-1662) describes the effects of ethanol, glycerol, and propylene glycol on the stability of Phenobarbital Sodium in aqueous solutions. Specifically, Gupta discloses that ethanol has the best effect followed by propylene glycol and glycerol relative to water alone. Years after Gupta, Parker et al., (WO 2017/085687) focused on minimizing the total amount of water to reduce the hydrolysis and consequently the formation of the degradation products. Parker addresses the hydrolysis issue by limiting the amount of water (e.g., to no more than 50 mg/mL) in the liquid formulation. Parker's minimized water formulations also include a C1-C4 alcohol such as ethanol and a glycol such as propylene glycol. However, while the amount of impurities in Parker's liquid formulation may have decreased compared to prior formulations, impurities such a PEAU are still present in undesirable amounts, particularly after extended storage.

In addition to the degradation impurities, the current marketed liquid formulation of Phenobarbital Sodium (e.g., Phenobarbital Sodium for Injection USP, 65 mg/mL or 130 mg/mL), includes organic solvents such as alcohol, which are not desirable in general and indeed not suitable for administration to newborns as described in the art, e.g., Williams et al., 1998, "Evaluating Toxic Alcohol Poisoning in the Emergency Setting," *Laboratory Medicine,* Vol. 29, No. 2; Wood et al., 2007, *J. of Perinatology,* 27:183-185; Kumar, 1985, "Adverse Drug Reactions in the Newborn," *Annals of Clin. And Lab. Sci,* Vol. 15, No. 3; and Cuzzolin, 2018, *J. Pediatric and Neonatal Individualized Med.,* doi: 10.7363/070112.

Accordingly, there is still a need for a stable Phenobarbital Sodium formulation in a formulation that is storage stable and void or essentially void of degradation impurities upon solubilization in water.

SUMMARY

Disclosed herein are compositions of, methods of producing, and use of a lyophilized Phenobarbital Sodium formulation. The contemplated composition is an amorphous lyophilized Phenobarbital Sodium with high stability and purity. The lyophilized composition may include no less than 98% Phenobarbital Sodium. The amorphous composition is a storage-stable form of lyophilized Phenobarbital Sodium.

The lyophilized amorphous formulation that was produced resulted in surprising, unexpected and desirable results. The quantity of undesirable and/or toxic degradation impurities that are produced from this formulation are less than those in current commercial products. And the stability of this formulation is superior to that of current commercial products. These results are particularly surprising and unexpected in view of the fact that conventional wisdom teaches that crystalline material is more stable than amorphous material (see e.g., C. Ahlneck and G. Zografi "The Molecular Basis for Moisture Effects on the Physical and Chemical Stability of Drugs in the Solid-State," Int. J. Pharm. 1990, 62, 87-95). Thus, one of ordinary skill in the art would want to avoid using amorphous material in pharmaceutical formulations.

Preferably the percentage of the lyophilized formulation that is amorphous is at least 20%, 25%, 30%, 35%, 40%, 45%, 50%, 55%, 60%, 65%, 70%, 75%, 80%, 85%, 90%, or 95%. Alternatively, the percentage of the lyophilized formulation that is amorphous can be 100%. In addition, the percentage of the lyophilized formulation that is amorphous can be within any range between (and including) 20% to 100% (e.g., 20%-100%, 25%-95%. etc.).

Methods for producing the storage-stable form of lyophilized Phenobarbital Sodium composition result in a lyophilized powder in which the impurity phenylethylacetylurea (PEAU) is below detection limit and is never more than 0.2% of the specification limit even after storage of the lyophilized Phenobarbital Sodium for up to 6 months under accelerated stability conditions (40° C., 75% RH). In some embodiments, the method for producing the storage-stable lyophilized Phenobarbital Sodium includes adding Phenobarbital Sodium to water to form a Phenobarbital Sodium solution, having a pH between 9.2 to 10.2, and lyophilizing the bulk solution. In some embodiments, the water is Water for Injection.

In preferred embodiments, the Water for Injection is sparged with nitrogen prior to adding the Phenobarbital Sodium. Typically, the Water for Injection is sparged with nitrogen for at least 30 minutes prior to adding the Phenobarbital Sodium. In additional embodiments, the water (e.g., Water for Injection) is cooled to or between 2 to 8° C. prior to adding the Phenobarbital Sodium.

For adjusting the pH of the Phenobarbital Sodium solution, the method for producing the storage-stable form of lyophilized Phenobarbital Sodium composition may also include measuring the pH of the Phenobarbital Sodium solution, wherein if the pH is higher than 10.2, the adjusting includes adding hydrochloric acid (HCl).

Typically, the resulting lyophilized Phenobarbital Sodium forms no more than 0.1% PEAU when reconstituted in an aqueous solution after storage of the lyophilized Phenobarbital Sodium for up to 6 months both at RT and accelerated stability conditions. More typically, the resulting lyophilized Phenobarbital Sodium forms no more than 0.05% PEAU when reconstituted in an aqueous solution after storage of the lyophilized Phenobarbital Sodium for up to 6 months at room temperature (RT) and under accelerated stability conditions (40° C.). Additionally, or alternatively, the resulting lyophilized Phenobarbital Sodium forms either an amount below the quantitative limit (BQL, 0.05%) or no detectable amount of PEAU, 2-ethyl-2-phenylmalonamide (2EPMM), or alpha-phenylbutyrylguanidine (PBG) when reconstituted in the aqueous solution after storage of the lyophilized Phenobarbital Sodium for up to 6 months at RT and accelerated stability conditions.

According to contemplated embodiments as disclosed herein, the amorphous lyophilized Phenobarbital Sodium composition is stable up to at least 6 months under accelerated stability conditions which is equivalent to 24 months at RT. In this respect, in some embodiments, the stability of the lyophilized Phenobarbital Sodium is determined by reconstituting the lyophilized Phenobarbital Sodium in an aqueous solution and measuring the amount of or the presence of phenylethylacetylurea (PEAU), 2-ethyl-2-phenylmalonamide (2EPMM), and/or alpha-phenylbutyrylguanidine (PBG).

Additional embodiments include the method for producing the storage-stable form of lyophilized Phenobarbital Sodium composition as disclosed in which the Phenobarbital Sodium solution is filtered prior to lyophilization.

Further embodiments include the method for producing the storage-stable form of lyophilized Phenobarbital Sodium composition as disclosed in which the Phenobarbital Sodium solution is aliquoted into a vial prior to lyophilization, and after lyophilization, a closure is applied to the vial under vacuum.

Aspects of the present disclosure also include a method of reducing formation of degradation products of Phenobarbital Sodium reconstituted in an aqueous solution, in which the method includes adding Phenobarbital Sodium to water to form a Phenobarbital Sodium solution, adjusting the pH of the Phenobarbital Sodium solution to or between 9.2 to 10.2, and lyophilizing the Phenobarbital Sodium solution to form stable white lyophilized powder of Phenobarbital Sodium.

In preferred embodiments, the Water for Injection is sparged with nitrogen prior to adding the Phenobarbital Sodium. Typically, the Water for Injection is sparged with nitrogen for at least 30 minutes prior to adding the Phenobarbital Sodium. In additional embodiments, the water (e.g., Water for Injection) is cooled to or between 2 to 8° C. prior to adding the Phenobarbital Sodium.

For adjusting the pH of the Phenobarbital Sodium solution, the method of reducing formation of degradation products of Phenobarbital Sodium reconstituted in an aqueous solution may also include measuring the pH of the Phenobarbital Sodium solution, wherein if the pH is higher than 10.2, the adjusting includes adding Hydrochloric acid (HCl).

In typical embodiments, the degradation products of Phenobarbital Sodium reconstituted in an aqueous solution include phenylethylacetylurea (PEAU), 2-ethyl-2-phenylmalonamide (2EPMM), and/or alpha-phenylbutyrylguanidine (PBG), and analysis of the formation of the degradation products includes reconstituting the stable lyophilized Phenobarbital Sodium in an aqueous solution to form a reconstituted solution, and quantitating the amount of or presence of PEAU, 2 EPMM, and/or PBG in the reconstituted solution.

In typical embodiments, the method of reducing formation of degradation products of Phenobarbital Sodium reconstituted in an aqueous solution results in the reconstituted solution having no less than 96% Phenobarbital Sodium. In more typical embodiments, the reconstituted solution has no less than 97% Phenobarbital Sodium. In some preferred embodiments, the reconstituted solution has no less than 98% Phenobarbital Sodium, and in other preferred embodiments between 95% and 105% Phenobarbital Sodium. In additional or alternative embodiments, the reconstituted solution has no more than 0.2% PEAU, 2 EPMM, and/or PBG, and preferably has 0.05% or less PEAU and no detectable amount of 2 EPMM or PBG.

Further aspects of the present disclosure include methods of treating an individual in need of Phenobarbital Sodium. These methods include adding saline or dextrose to the lyophilized powder of Phenobarbital Sodium as disclosed herein immediately prior to administration to form a Phenobarbital Sodium reconstituted solution and administering the Phenobarbital Sodium reconstituted solution to the individual. In some embodiments, the individual in need of Phenobarbital Sodium suffers from epilepsy. In particular embodiments, the individual in need of Phenobarbital Sodium is a newborn suffering from neonatal epilepsy. In other embodiments, the lyophilized amorphous Phenobarbital Sodium is a powder dose of 65 mg, 130 mg, 100 mg or 200 mg. In typical embodiments, the administering of the Phenobarbital Sodium reconstituted solution to the individual includes intramuscular injection or intravenous injection.

Additional aspects of the present disclosure include a pharmaceutical product including a vial containing the white lyophilized powder of Phenobarbital Sodium for reconstitution prior to administration, in which the composition was lyophilized in the vial and the vial includes a closure positioned in order to seal the vial under vacuum after Lyophilization.

Therefore, the inventors also contemplate lyophilized Phenobarbital Sodium.

Various objects, features, aspects, and advantages will become more apparent from the following detailed description of preferred embodiments, along with the accompanying drawings.

DETAILED DESCRIPTION

The inventors have surprisingly discovered a method for making a storage-stable and highly purified Phenobarbital Sodium composition that is void of any detectable impurities in its lyophilized powder form and is essentially void of impurities upon reconstitution in water. The contemplated Phenobarbital Sodium composition is a lyophilized powder that is no less than 98% Phenobarbital Sodium and is stable (25° C., 65% RH and 40° C., 75% RH) for up to at least 6 months under accelerated conditions which is equivalent to 24 months at RT. Upon reconstitution (e.g. solubilization/resuspension) in water, the lyophilized Phenobarbital Sodium forms no more than 0.05% of 2-ethyl-2-phenylmalonamide (2EPMM) or alpha-phenylbutyrylguanidine (PBG), and phenylethylacetylurea (PEAU).

The Phenobarbital Sodium composition as described herein refers to Phenobarbital Sodium having an IUPAC (International Union of Pure and Applied Chemistry) name of sodium 5-ethyl-4,6-dioxo-5-phenyl-1H-pyrimidin-2-olate, a Chemical Abstract Service (CAS) No. 57-30-7, and a molecular formula of $C_{12}H_{11}N_2NaO_3$.

In order to avoid hydrolysis of Phenobarbital Sodium and therefore the formation of its toxic degradation products, the inventors have unexpectedly discovered that a lyophilized Phenobarbital Sodium formed by the methods disclosed herein results in a storage-stable lyophilized powder of Phenobarbital Sodium. In particular, with reference to the polarized light photomicrographs of FIGS. 1A-1F and the XRPD analysis shown in FIG. 5A-5D, the storage-stable lyophilized powder of Phenobarbital Sodium has an amorphous structure. Without wishing to be bound by any theory or hypothesis, the lyophilized Phenobarbital Sodium produced following the methods according to embodiments of the present disclosure produces an amorphous structure that contributes to the observed stability of this composition upon reconstitution in water. Irrespective of the mechanism of action, the contemplated lyophilized Phenobarbital Sodium composition is stable and upon reconstitution in water, does not form significant (e.g., not measurable or not detectable) amounts of the toxic degradation products—namely PEAU, 2EPMM, or PBG.

Figure 1A:
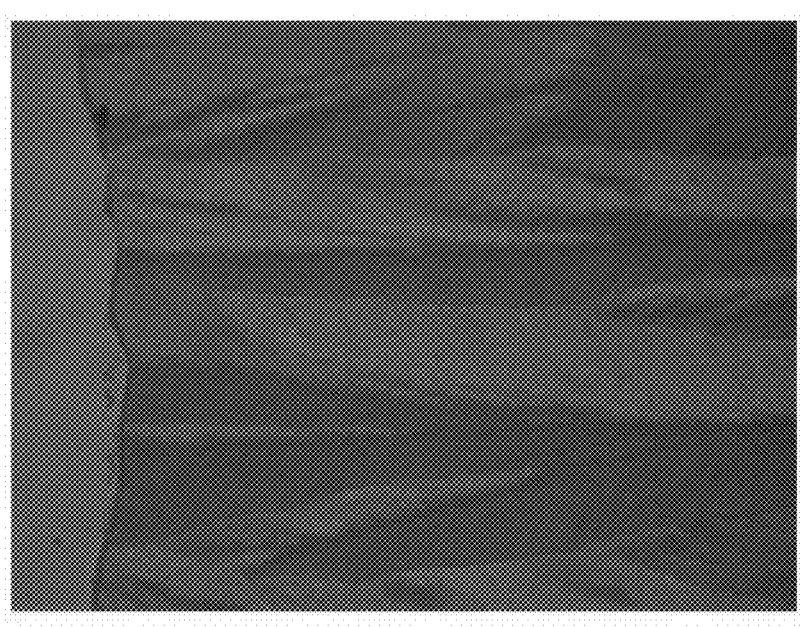
FIG. 1A is a polarized light photomicrograph of the presently disclosed Phenobarbital Sodium in water during Lyophilization microscopy at −50° C., as indicated.
Figure 1B:
FIG. 1B is a polarized light photomicrograph of the presently disclosed Phenobarbital Sodium in water during Lyophilization microscopy at −45.5° C. as indicated.
Figure 1C:
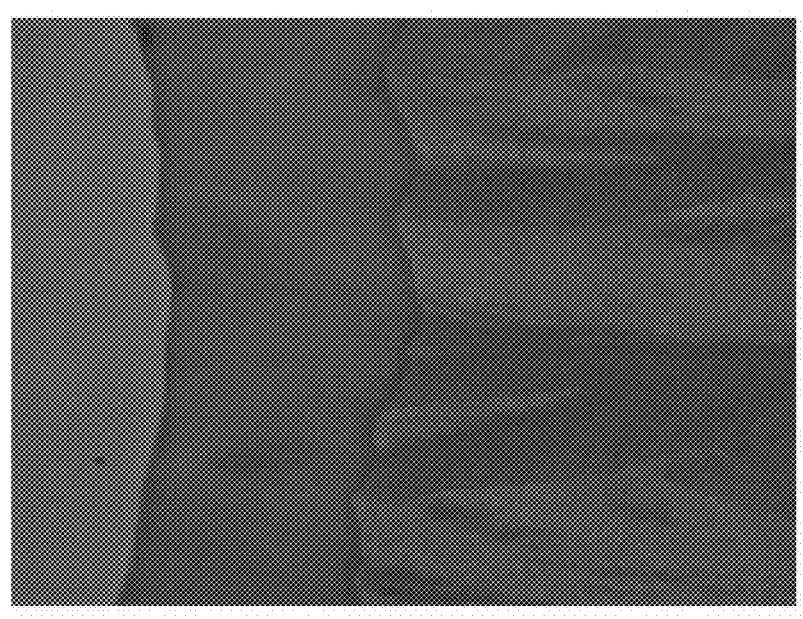
FIG. 1C is a polarized light photomicrograph of the presently disclosed Phenobarbital Sodium in water during Lyophilization microscopy at −40.0° C. as indicated.
Figure 1D:
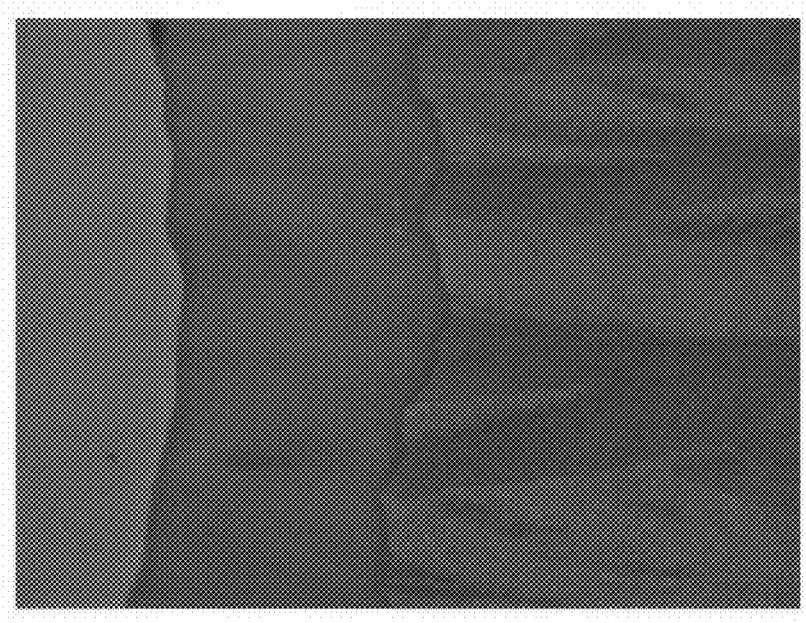
FIG. 1D is a polarized light photomicrograph of the presently disclosed Phenobarbital Sodium in water during Lyophilization microscopy at −39.6° C. as indicated.
Figure 1E:
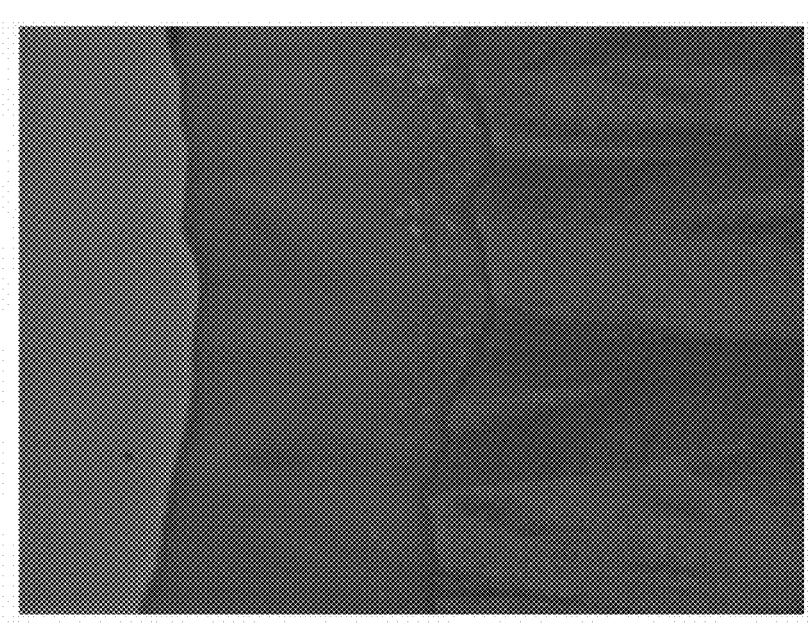
FIG. 1E is a polarized light photomicrograph of the presently disclosed Phenobarbital Sodium in water during Lyophilization microscopy at −39.2° C. as indicated.
Figure 1F:
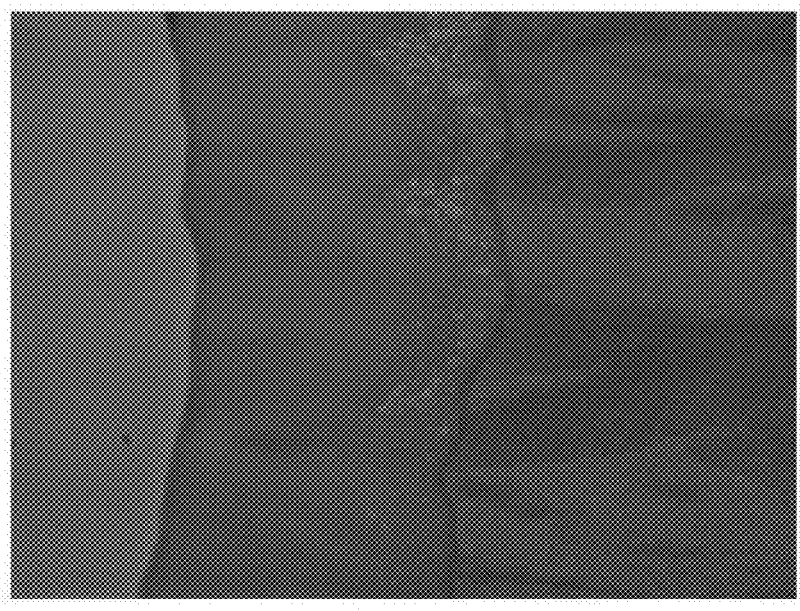
FIG. 1F is a polarized light photomicrograph of the presently disclosed Phenobarbital Sodium in water during Lyophilization microscopy at −38.8° C. as indicated.
Figure 2A:
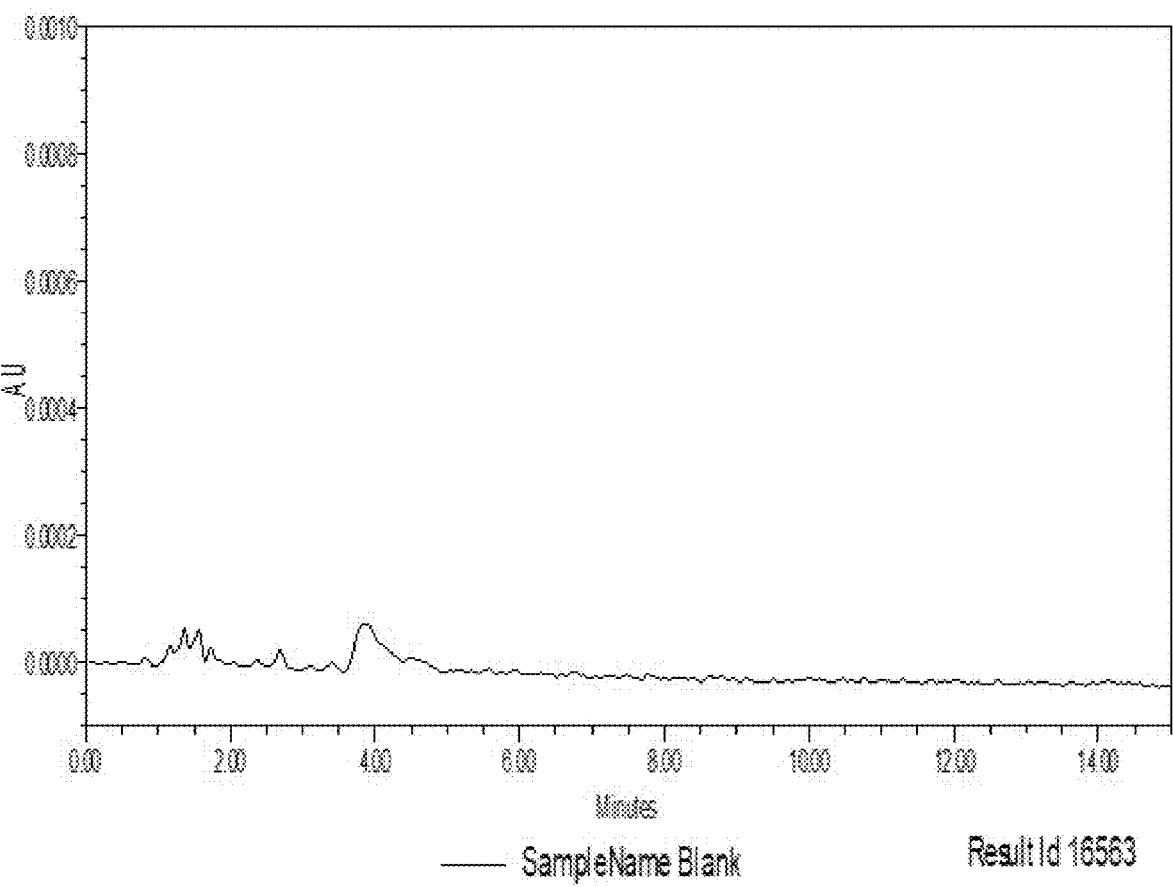
FIG. 2A is a chromatogram from an injection of a "blank solution" for assay by high performance liquid chromatography (HPLC) at a detection wavelength of 210 nanometers (nm), as described herein.
Figure 2B:
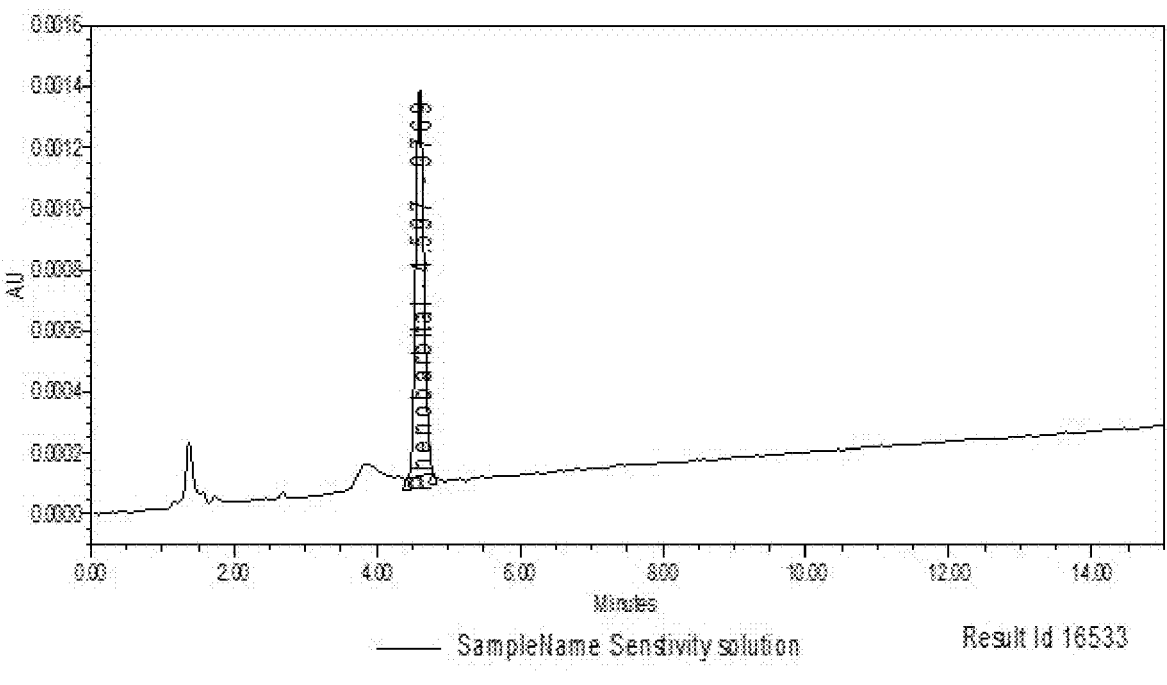
FIG. 2B is a chromatogram from an injection of the "Sensitivity solution" of Phenobarbital for related substances by HPLC at a detection wavelength of 210 nm, as described herein.
Figure 2C:
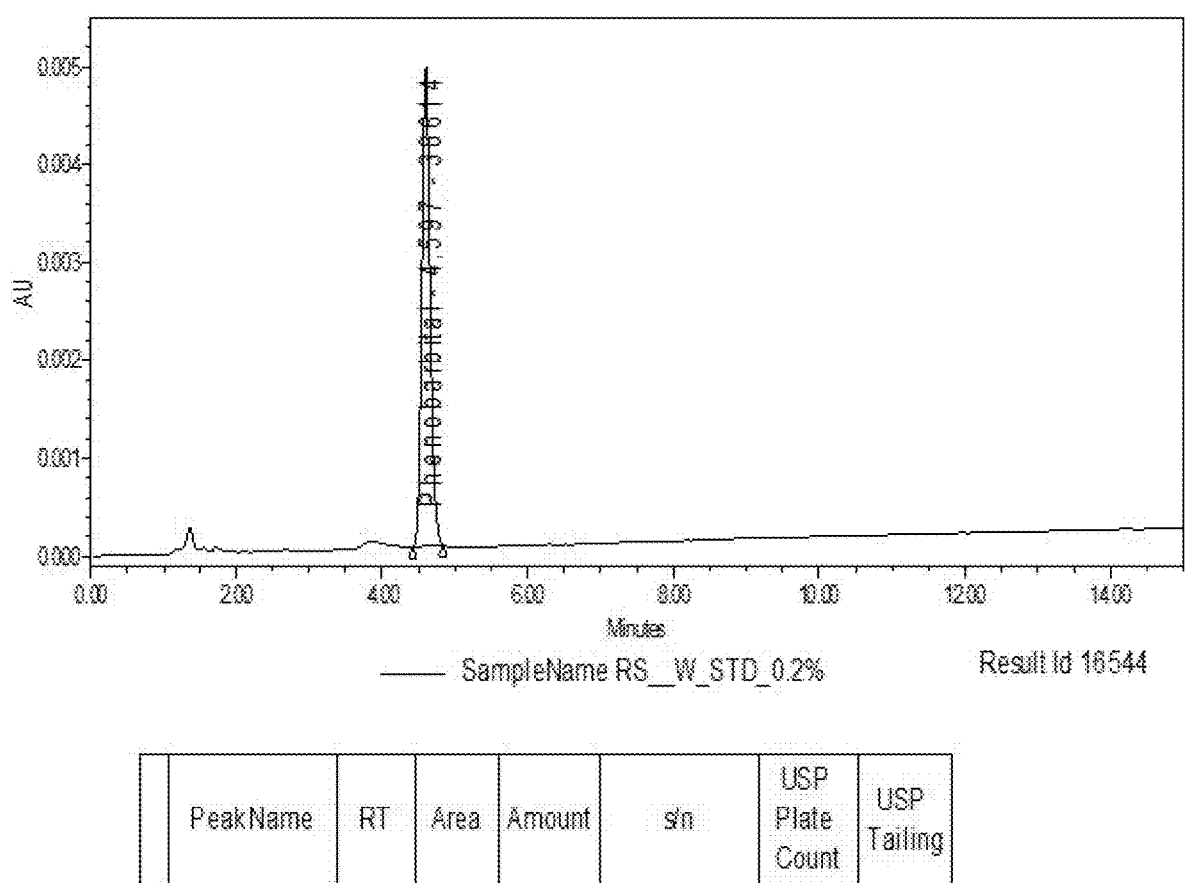
FIG. 2C is a chromatogram from an injection of a "related substance" (RS) working standard at 0.2% impurity level) for assay of related substances by HPLC at a detection wavelength of 210 nm, as described herein.
Figure 2D:
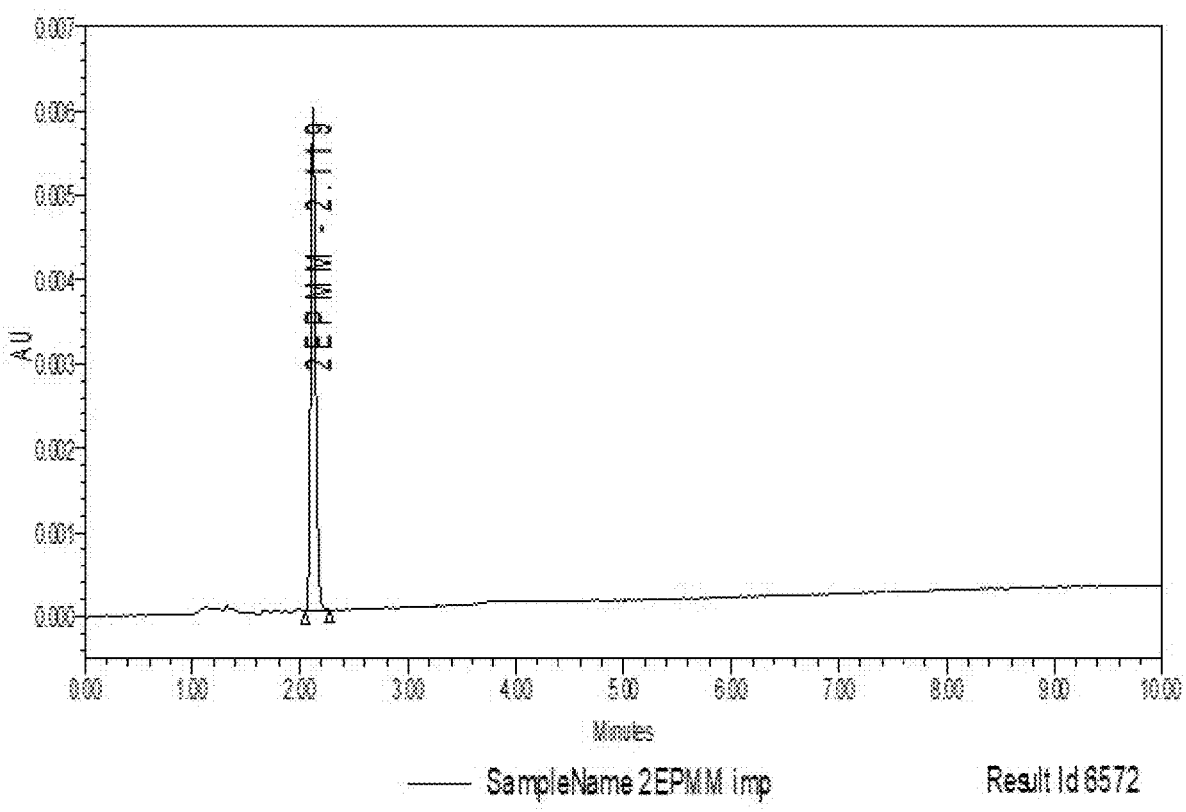
FIG. 2D is a chromatogram from an injection of 2-ethyl-2-phenylmalonamide (2EPMM) for assay of related substances by HPLC at a detection wavelength of 210 nm, as described herein.
Figure 2E:
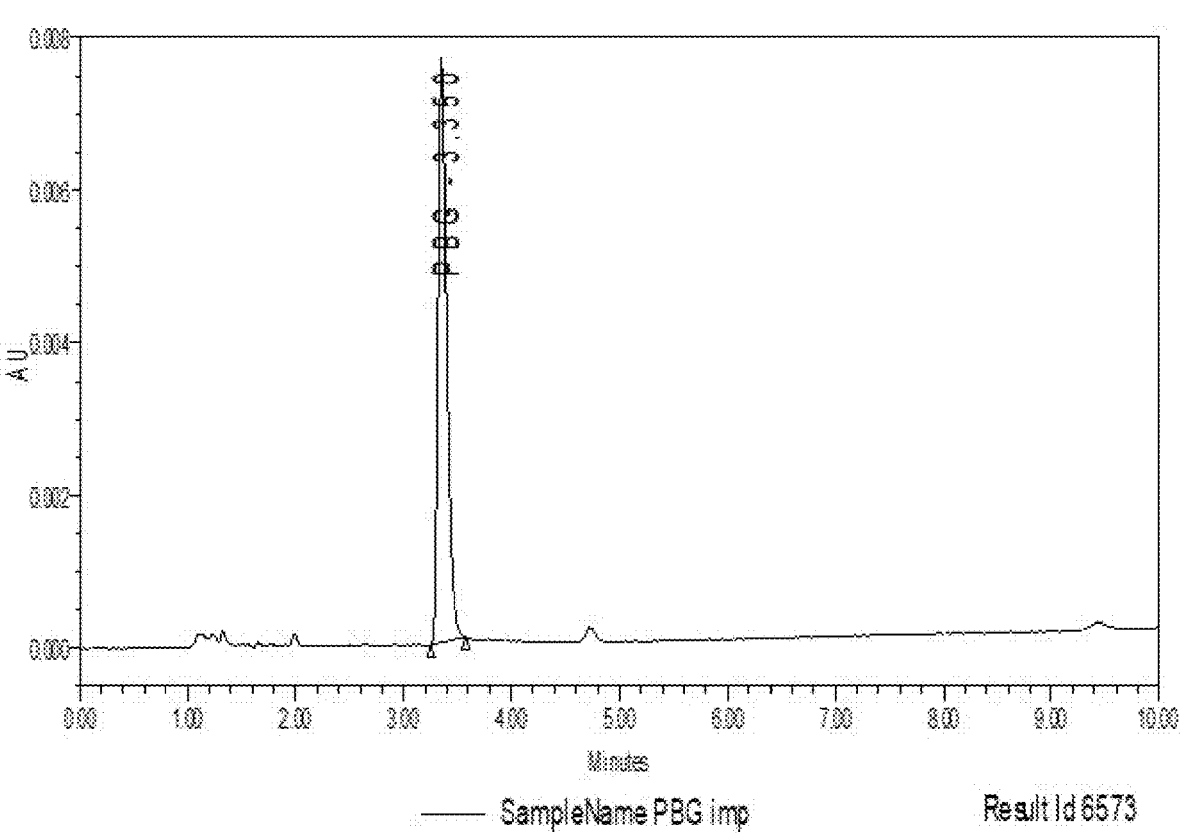
FIG. 2E is a chromatogram from an injection of alpha-phenylbutyrylguanidine (PBG) for assay of related substances by HPLC at a detection wavelength of 210 nm, as described herein.
Figure 2F:
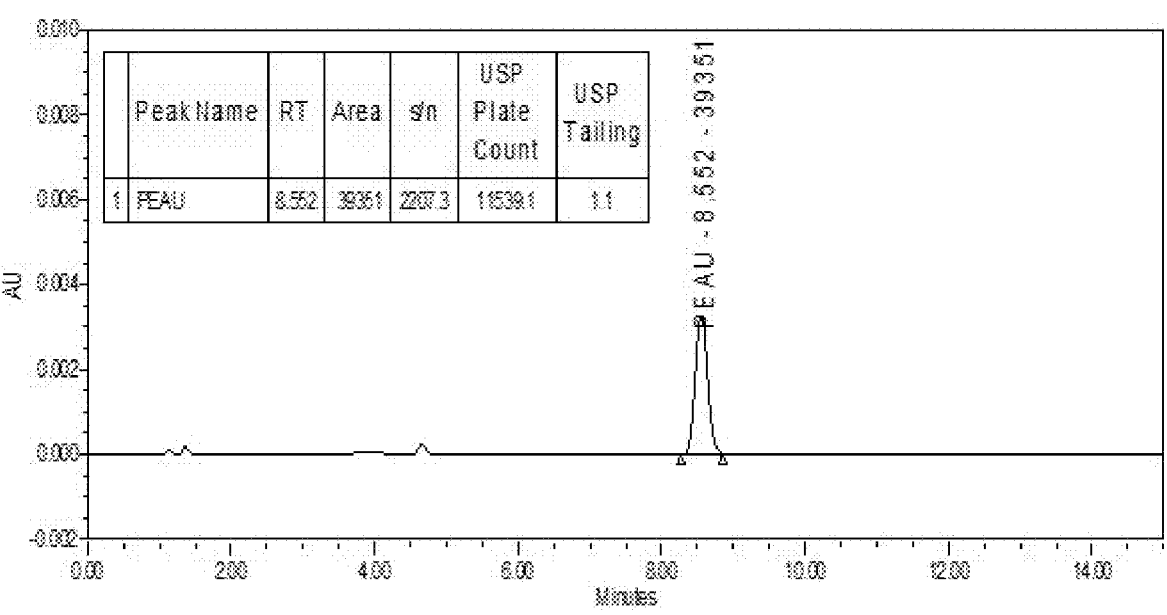
FIG. 2F is a chromatogram from an injection of phenylethylacetylurea (PEAU) for assay of related substances by HPLC at a detection wavelength of 210 nm, as described herein.
Figure 2G:
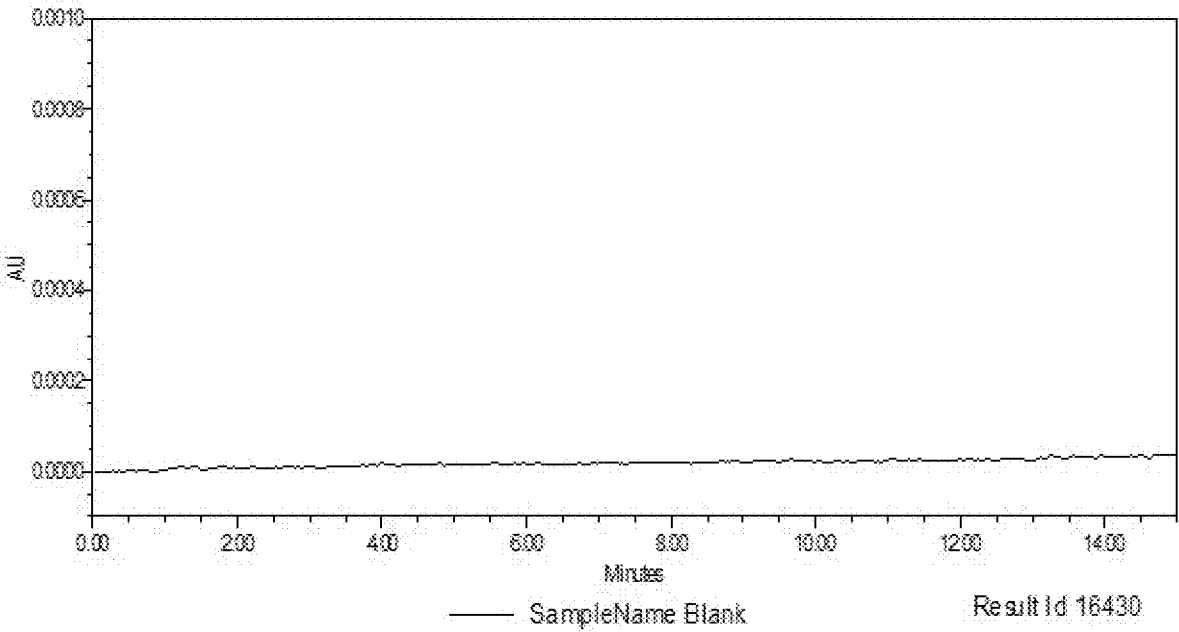
FIG. 2G is a chromatogram from an injection of a "blank solution" for assay by HPLC at a detection wavelength of 254 nm, as described herein.
Figure 2H:
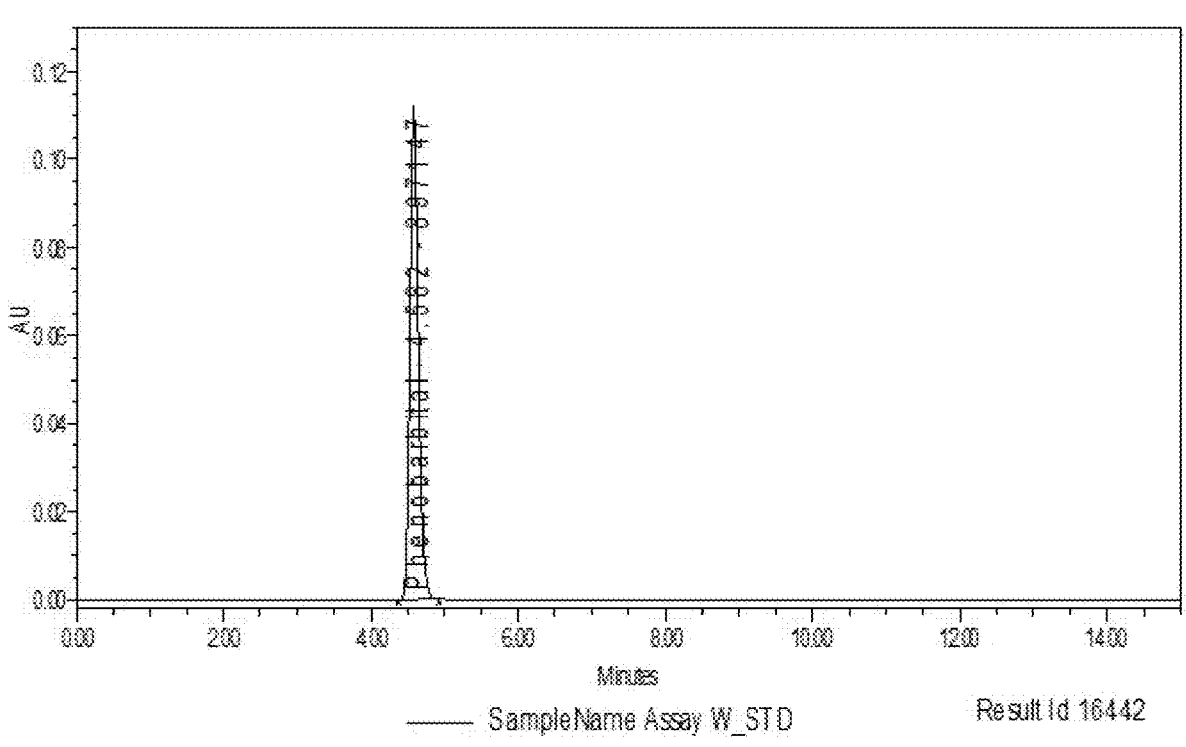
FIG. 2H is a chromatogram from an injection of an "assay working standard" for assay by HPLC at a detection wavelength of 254 nm, as described herein.
Figure 3A:
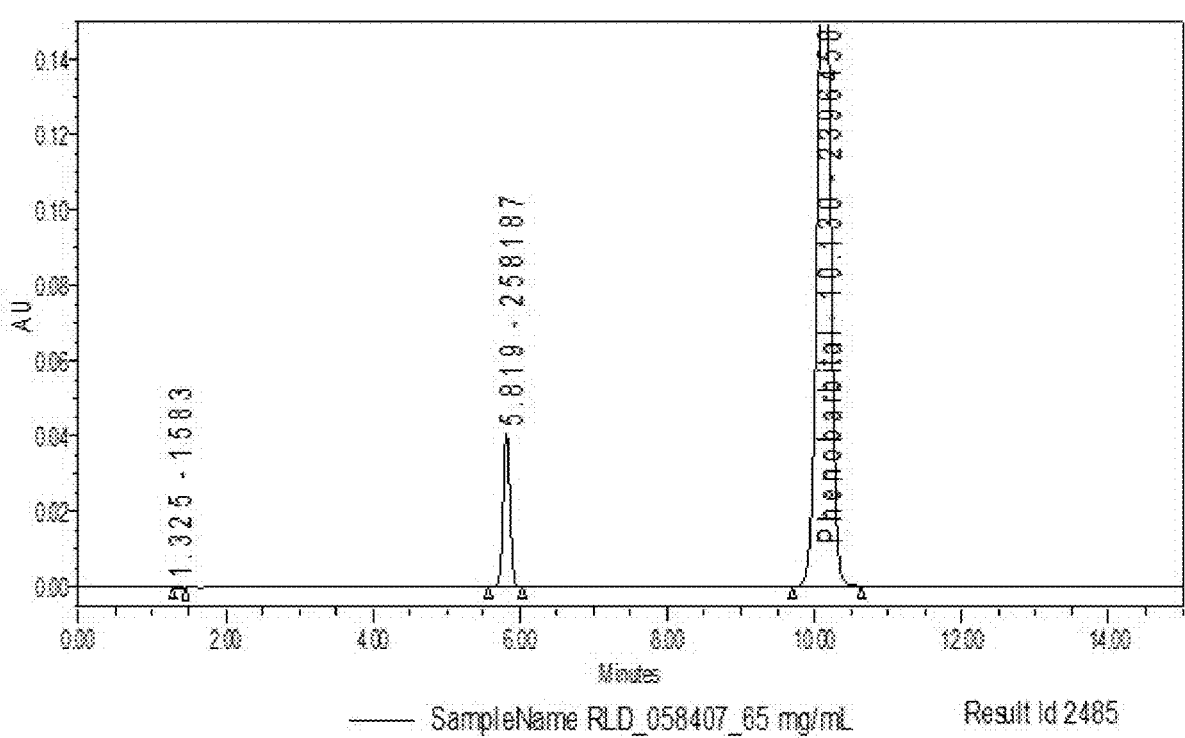
FIG. 3A is a chromatogram from an injection of a marketed liquid formulation of Phenobarbital Sodium at 65 mg/mL at initial time point for assay by HPLC at a detection wavelength of 254 nm, as described herein.
Figure 3B:
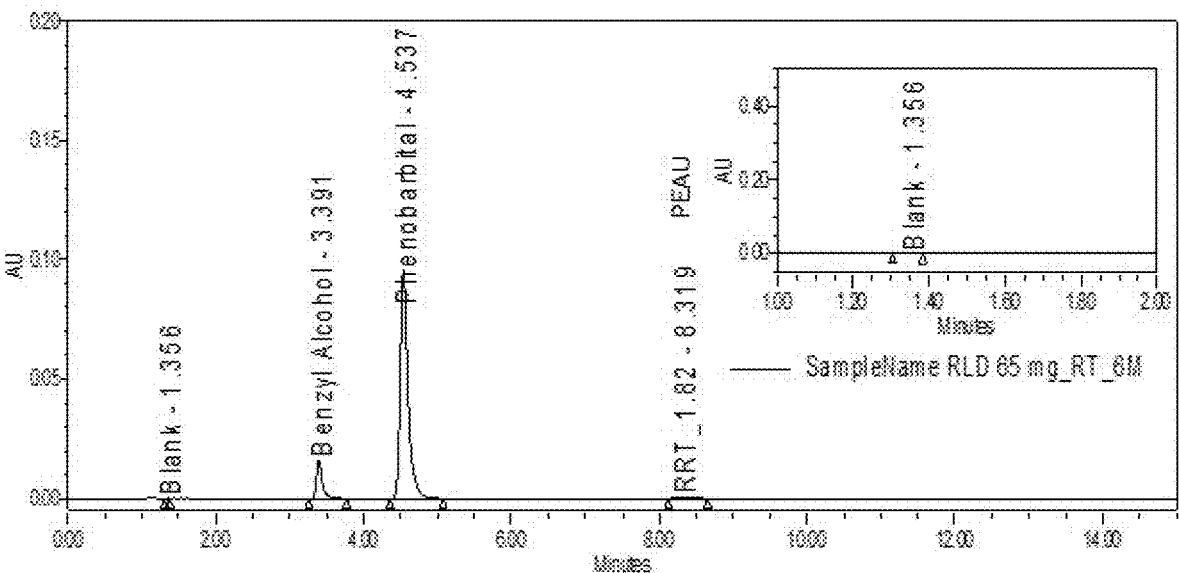
FIG. 3B is a chromatogram from an injection of a marketed liquid formulation of Phenobarbital Sodium at 65 mg/mL at 6 months from initial time point at room temperature (RT) for assay by HPLC at a detection wavelength of 254 nm, as described herein.
Figure 3C:
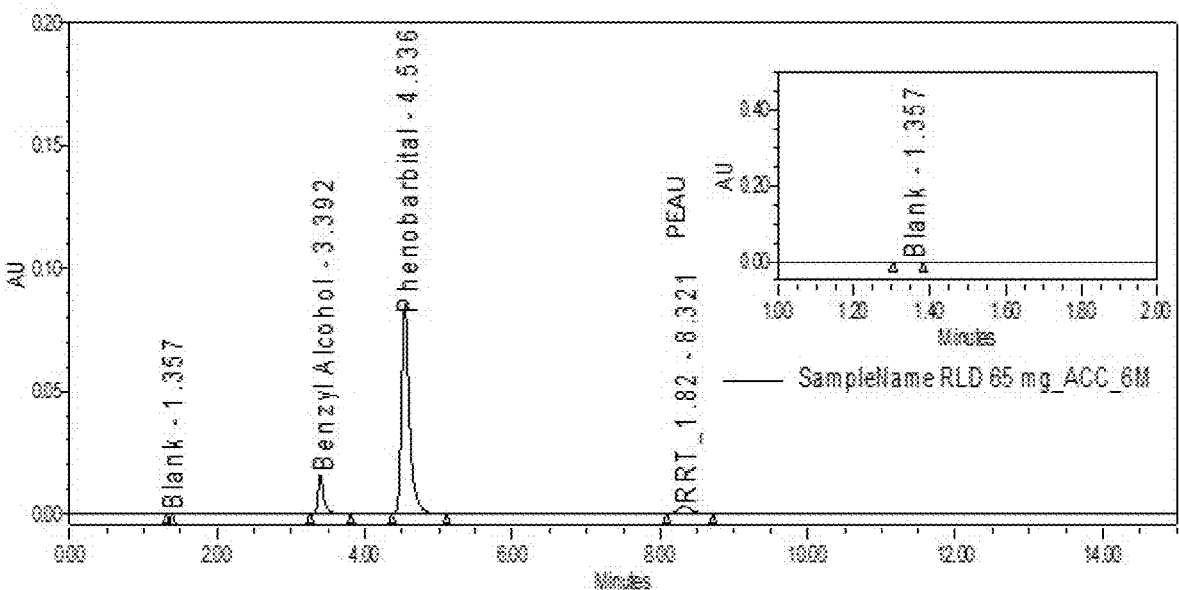
FIG. 3C is a chromatogram from an injection of a marketed liquid formulation of Phenobarbital Sodium at 65 mg/mL at 6 months from initial time point at accelerated stability conditions (ACC) for assay by HPLC at a detection wavelength of 254 nm, as described herein.
Figure 3D:
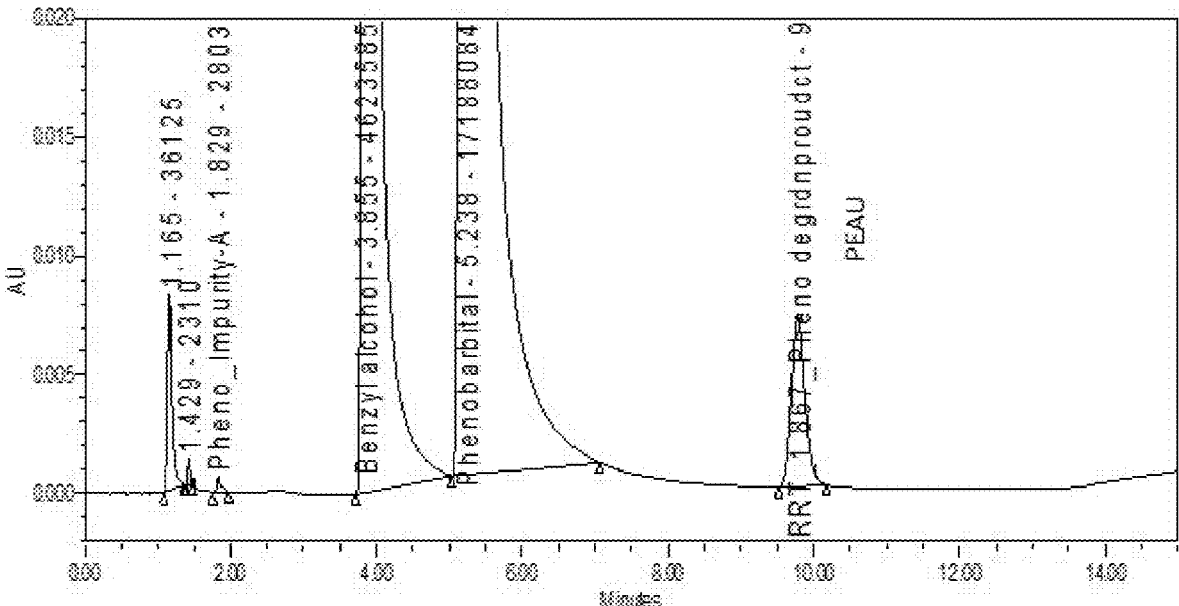
FIG. 3D is a chromatogram from an injection of a marketed liquid formulation of Phenobarbital Sodium at 65 mg/mL at initial time point for related substances by HPLC at a detection wavelength of 210 nm, as described herein.
Figure 3E:
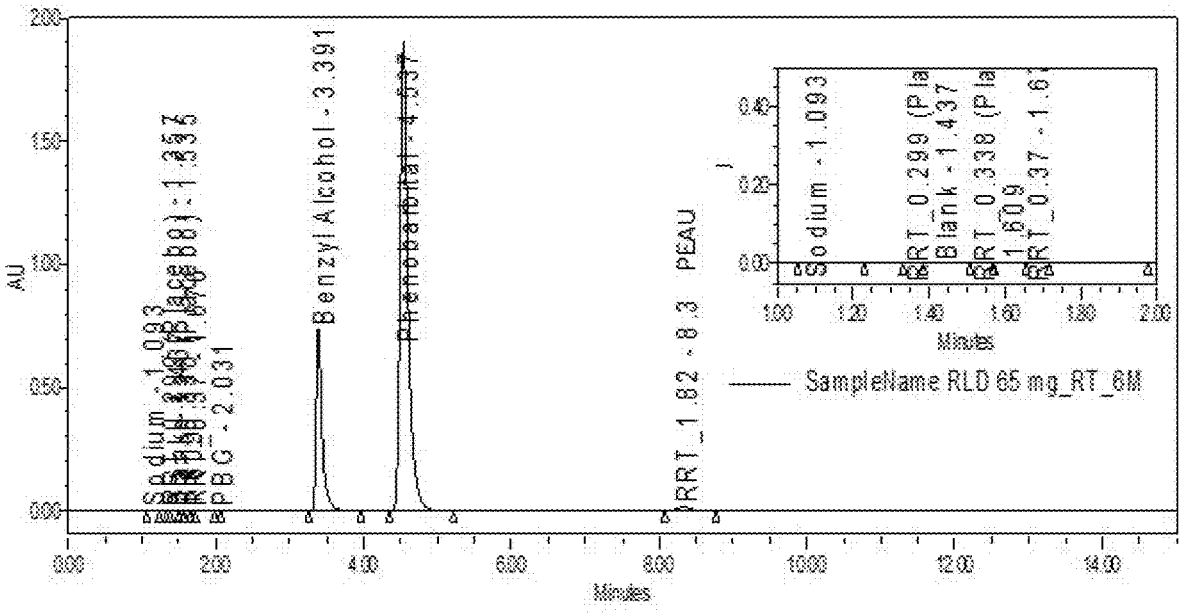
FIG. 3E is a chromatogram from an injection of a marketed liquid formulation of Phenobarbital Sodium at 65 mg/mL at 6 months from initial time point at room temperature (RT) for related substances by HPLC at a detection wavelength of 210 nm, as described herein.
Figure 3F:
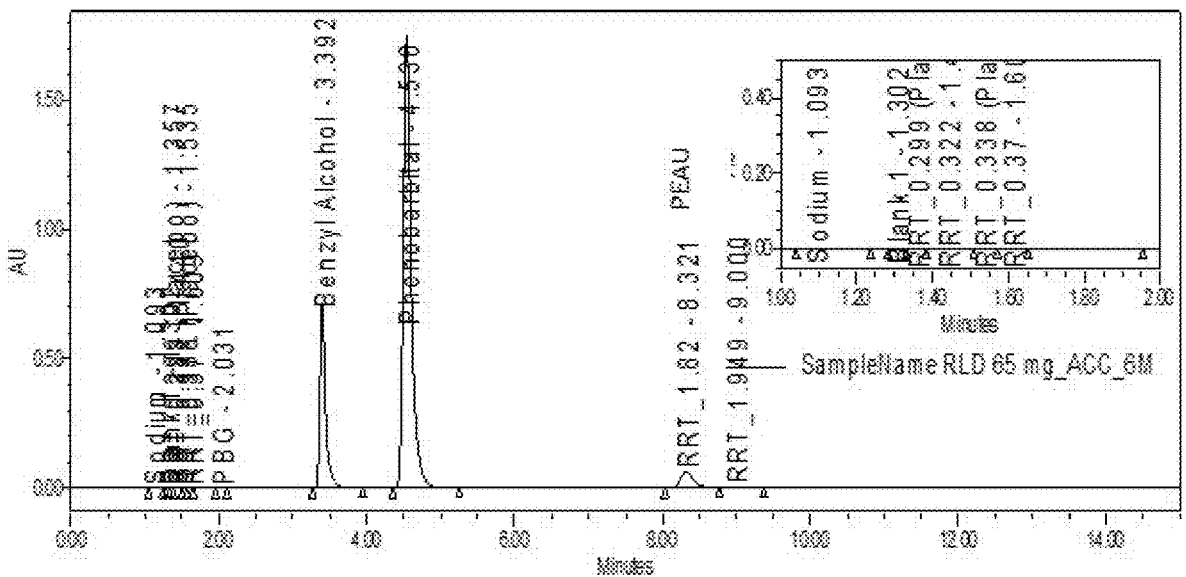
FIG. 3F is a chromatogram from an injection of a marketed liquid formulation of Phenobarbital Sodium at 65 mg/mL at 6 months from initial time point at accelerated stability conditions (ACC) for related substances by HPLC at a detection wavelength of 210 nm, as described herein.
Figure 3G:
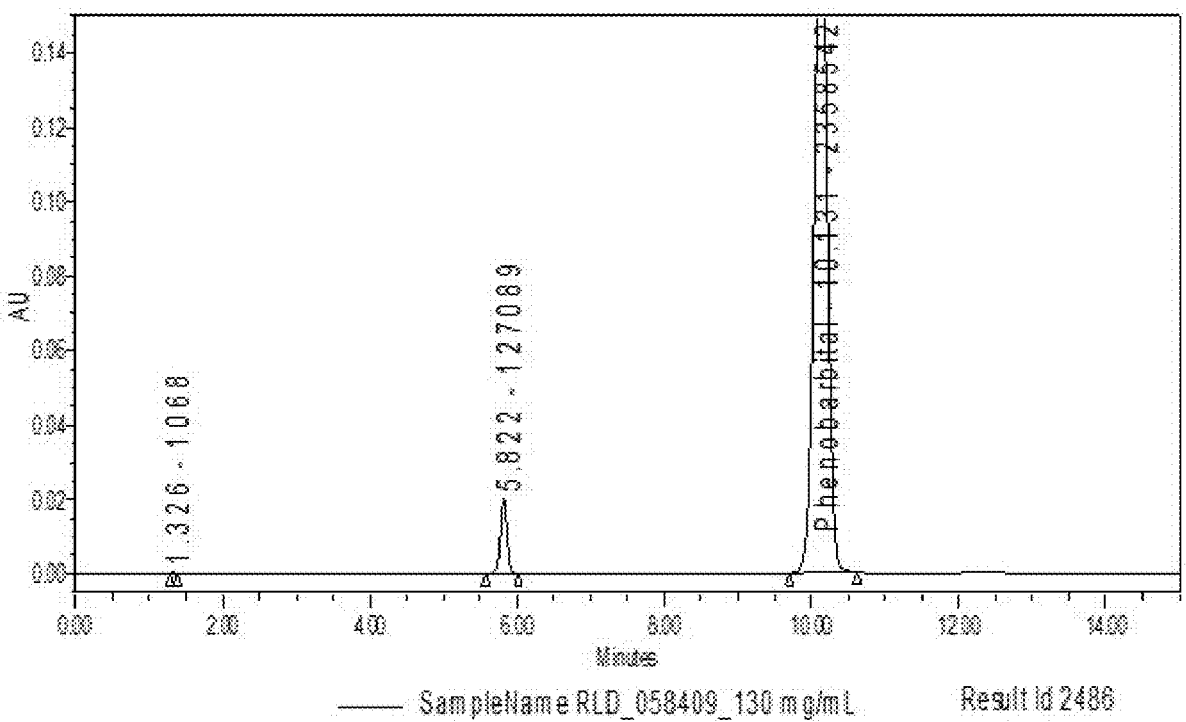
FIG. 3G is a chromatogram from an injection of a marketed liquid formulation of Phenobarbital Sodium at 130 mg/mL at initial time point for assay by HPLC at a detection wavelength of 254 nm, as described herein.
Figure 3H:
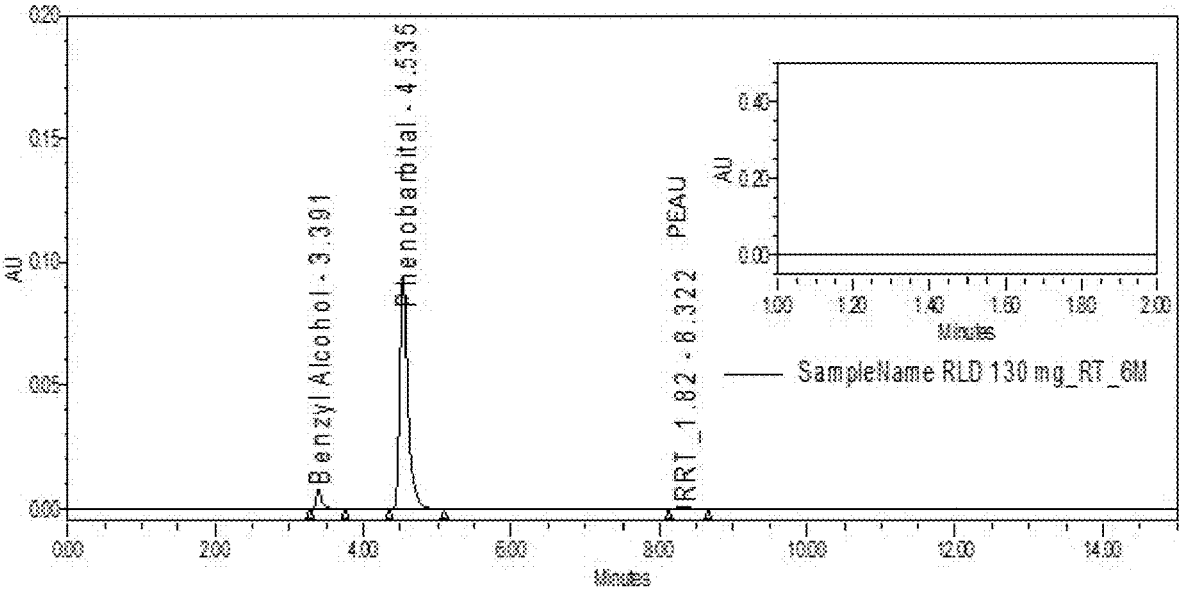
FIG. 3H is a chromatogram from an injection of a marketed liquid formulation of Phenobarbital Sodium at 130 mg/mL at 6 months from initial time point at room temperature (RT) for assay by HPLC at a detection wavelength of 254 nm, as described herein.
Figure 3I:
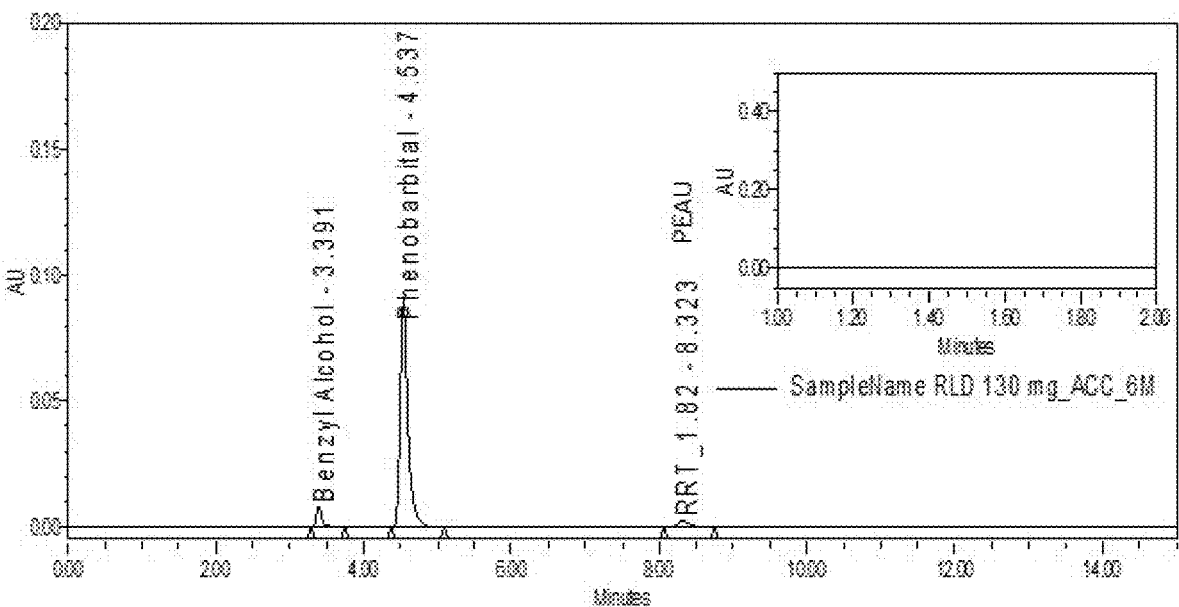
FIG. 3I is a chromatogram from an injection of a marketed liquid formulation of Phenobarbital Sodium at 130 mg/mL at 6 months from initial time point at accelerated stability conditions (ACC) for assay by HPLC at a detection wavelength of 254 nm, as described herein.
Figure 3J:
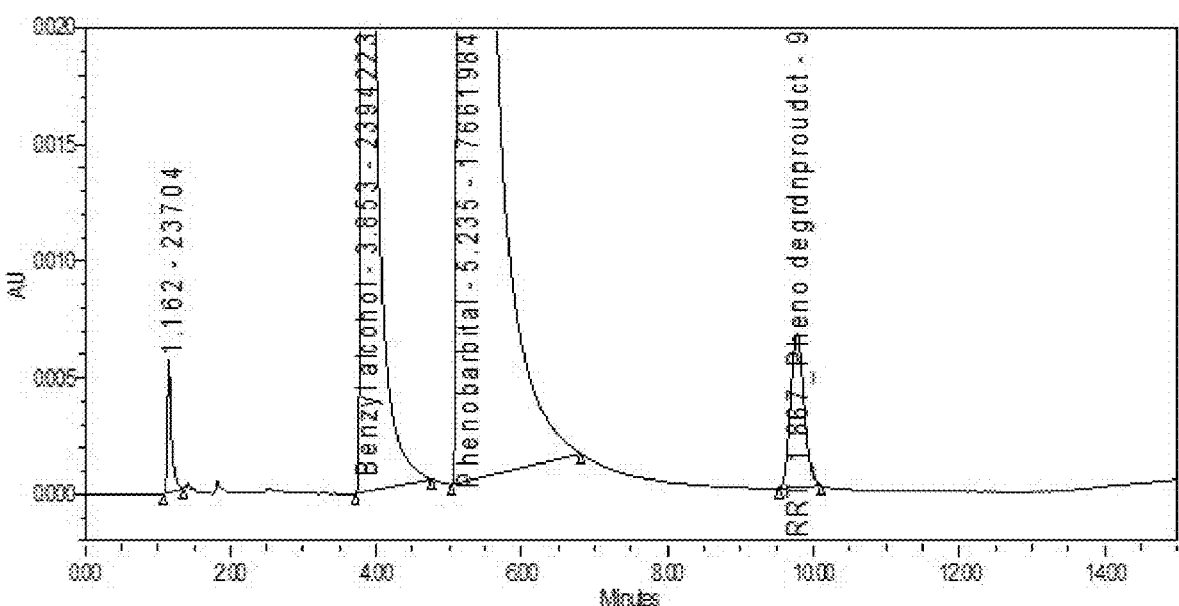
FIG. 3J is a chromatogram from an injection of a marketed liquid formulation of Phenobarbital Sodium at 130 mg/mL at initial time point for related substances by HPLC at a detection wavelength of 210 nm, as described herein.
Figure 3K:
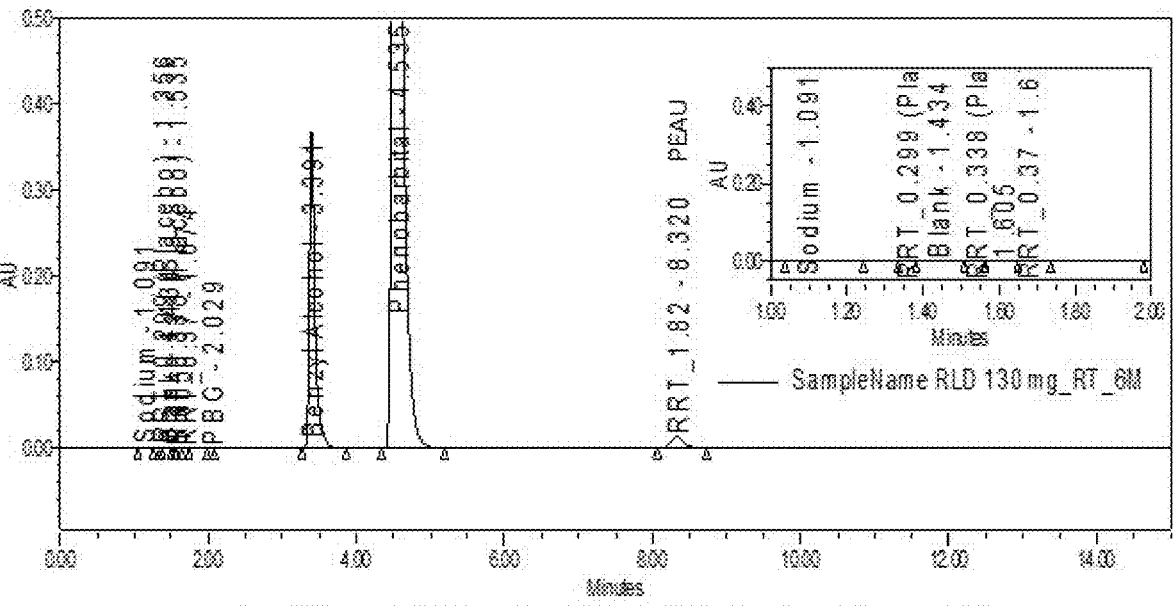
FIG. 3K is a chromatogram from an injection of a marketed liquid formulation of Phenobarbital Sodium at 130 mg/mL at 6 months from initial time point at room temperature (RT) for related substances by HPLC at a detection wavelength of 210 nm, as described herein.
Figure 3L:
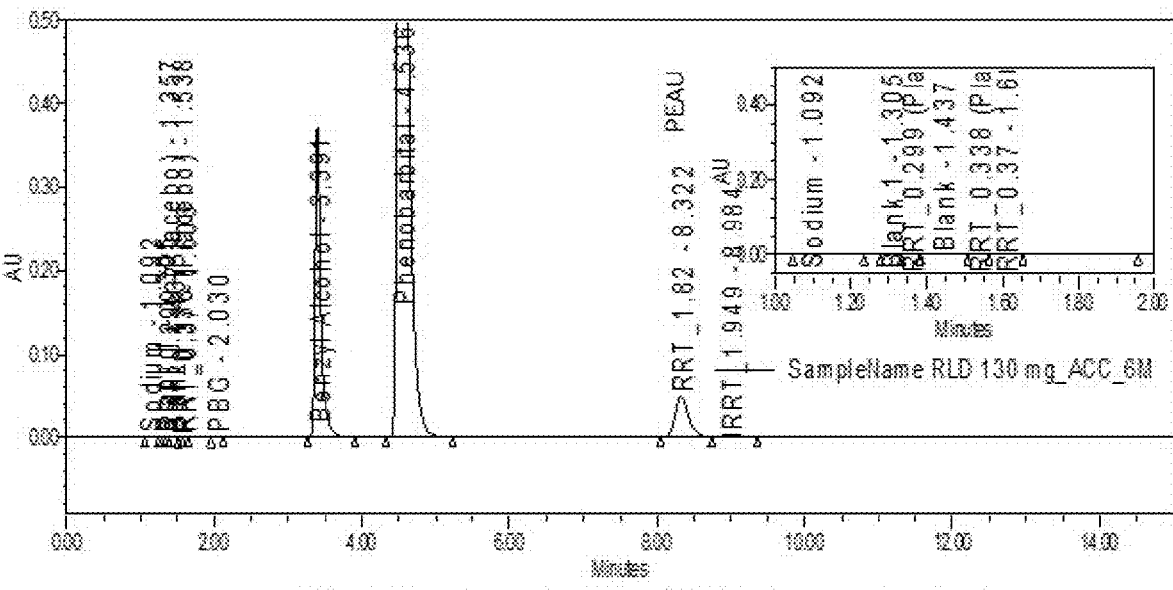
FIG. 3L is a chromatogram from an injection of a marketed liquid formulation of Phenobarbital Sodium at 130 mg/mL at 6 months from initial time point at accelerated stability conditions (ACC) for related substances by HPLC at a detection wavelength of 210 nm, as described herein.
Figure 4A:
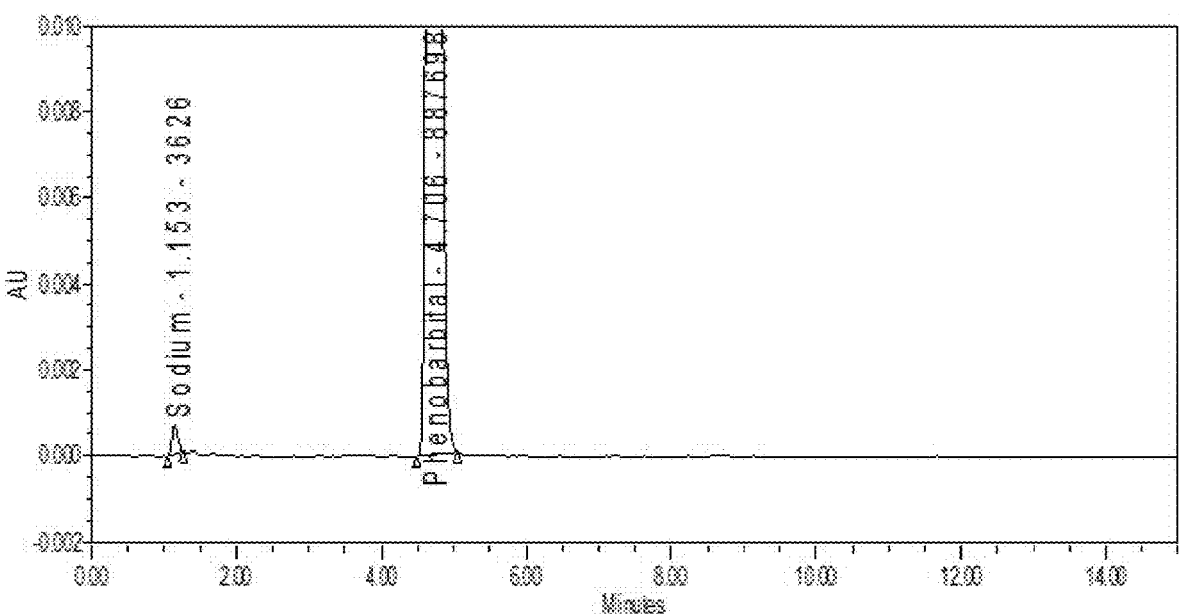
FIG. 4A is a chromatogram from an injection of the disclosed reconstituted lyophilized formulation of Phenobarbital Sodium at 65 mg/mL at initial time point for assay by HPLC at a detection wavelength of 254 nm, according to embodiments of the present invention.
Figure 4B:
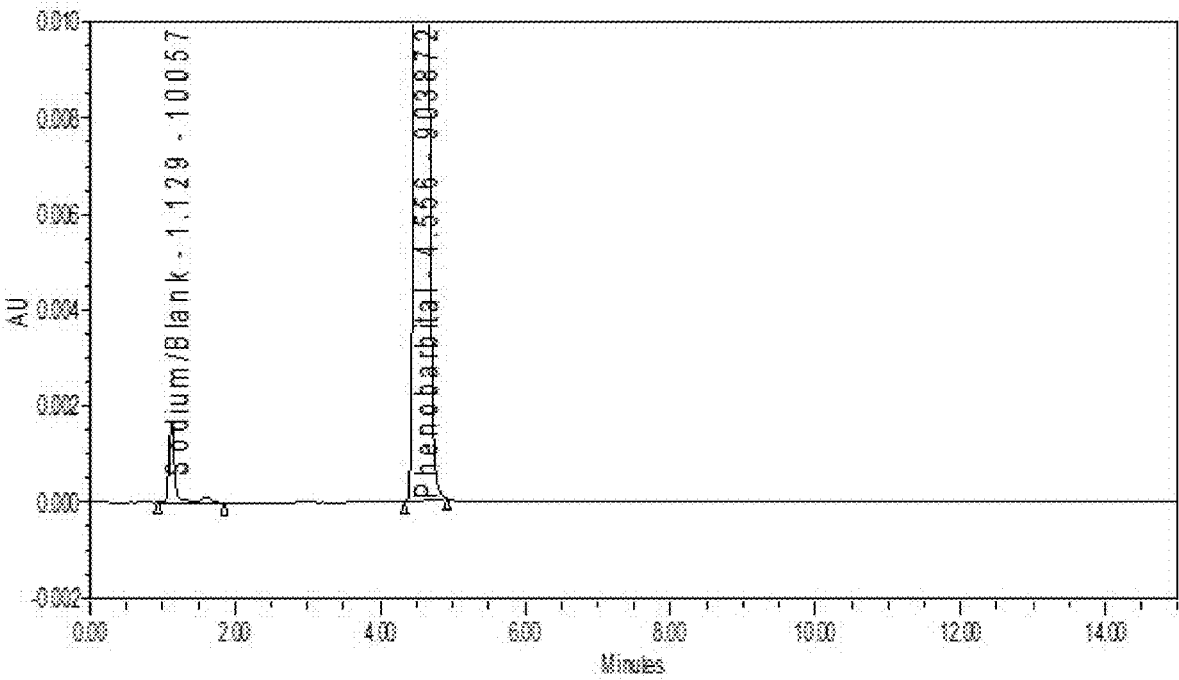
FIG. 4B is a chromatogram from an injection of the disclosed reconstituted lyophilized formulation of Phenobarbital Sodium at 65 mg/mL at 6 months from initial time point at room temperature (RT) for assay by HPLC at a detection wavelength of 254 nm, according to embodiments of the present invention.
Figure 4C:
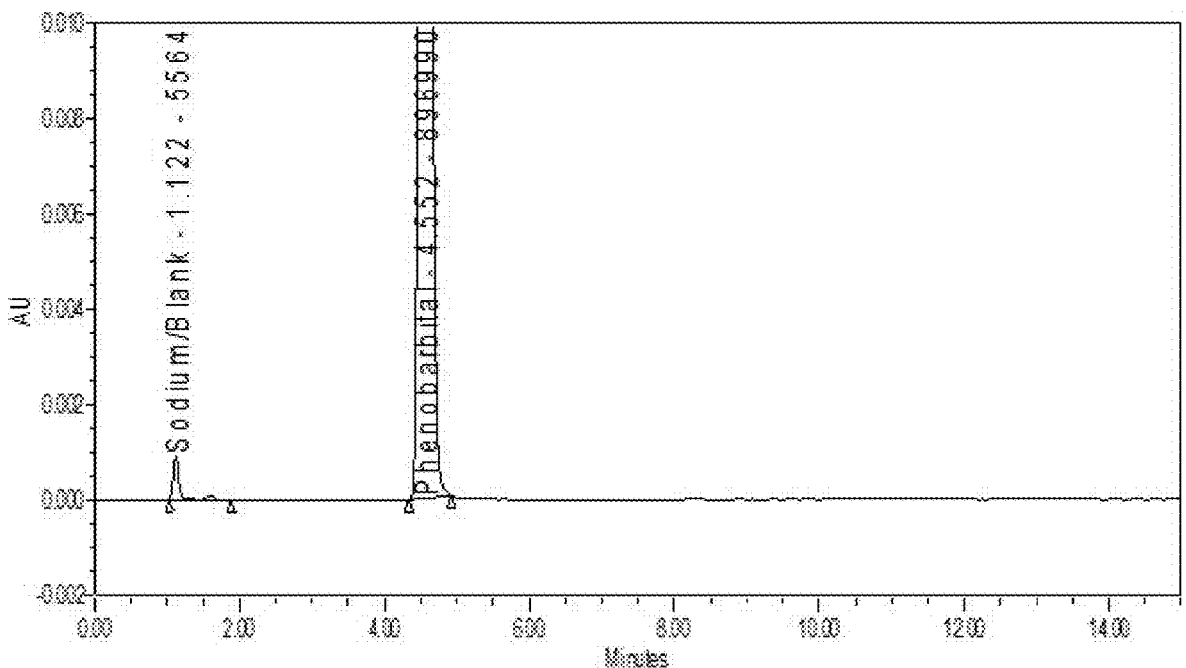
FIG. 4C is a chromatogram from an injection of the disclosed reconstituted lyophilized formulation of Phenobarbital Sodium at 65 mg/mL at 6 months from initial time point at accelerated stability conditions (ACC) for assay by HPLC at a detection wavelength of 254 nm, according to embodiments of the present invention.
Figure 4D:
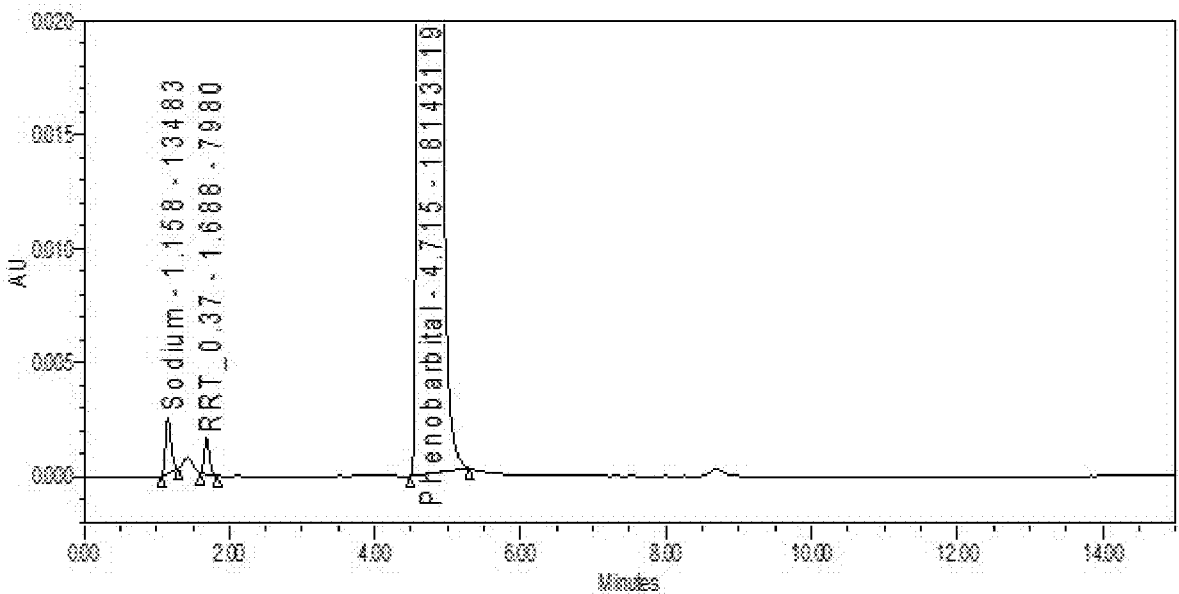
FIG. 4D is a chromatogram from an injection of the disclosed reconstituted lyophilized formulation of Phenobarbital Sodium at 65 mg/mL at initial time point for related substances by HPLC at a detection wavelength of 210 nm, according to embodiments of the present invention.
Figure 4E:
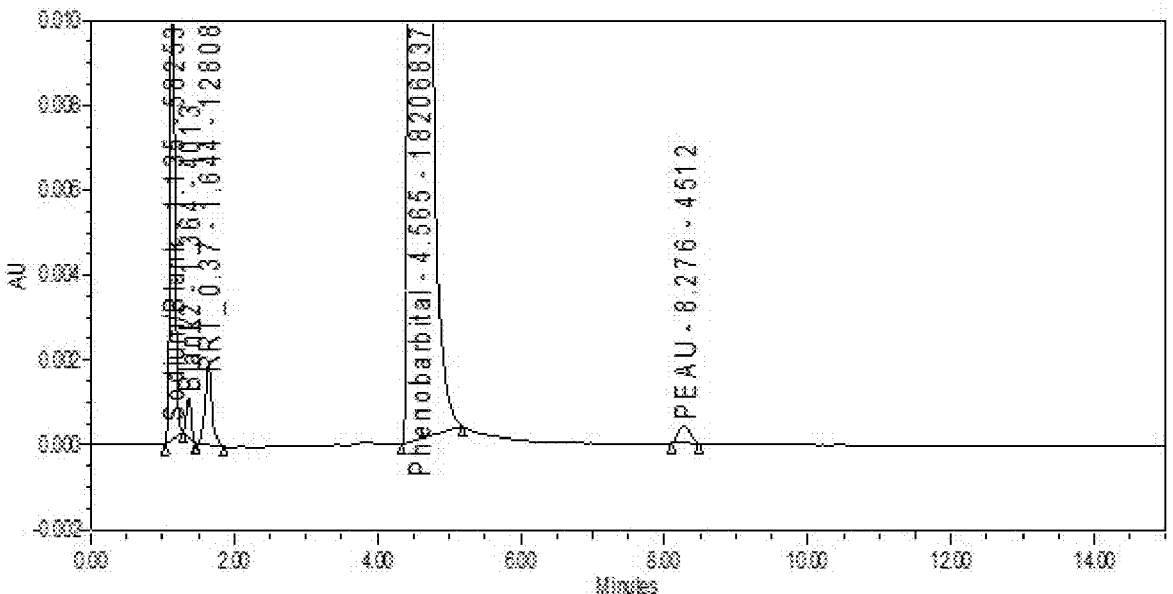
FIG. 4E is a chromatogram from an injection of the disclosed reconstituted lyophilized formulation of Phenobarbital Sodium at 65 mg/mL at 6 months from initial time point at room temperature (RT) for related substances by HPLC at a detection wavelength of 210 nm, according to embodiments of the present invention.
Figure 4F:
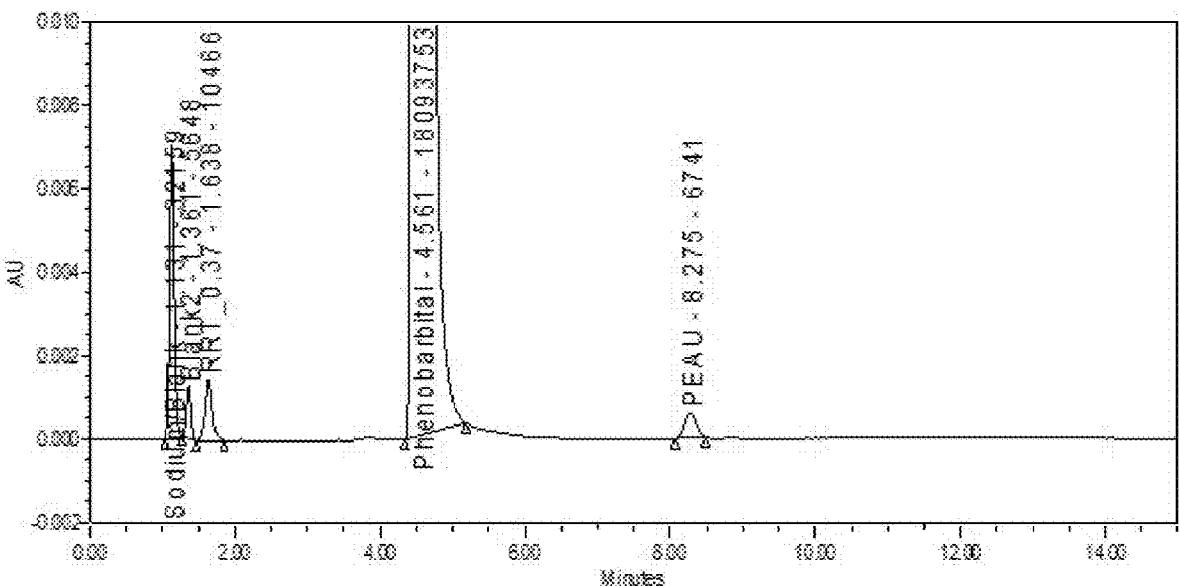
FIG. 4F is a chromatogram from an injection of the disclosed reconstituted lyophilized formulation of Phenobarbital Sodium at 65 mg/mL at 6 months from initial time point at accelerated stability conditions (ACC) for related substances by HPLC at a detection wavelength of 210 nm, according to embodiments of the present invention.
Figure 4G:
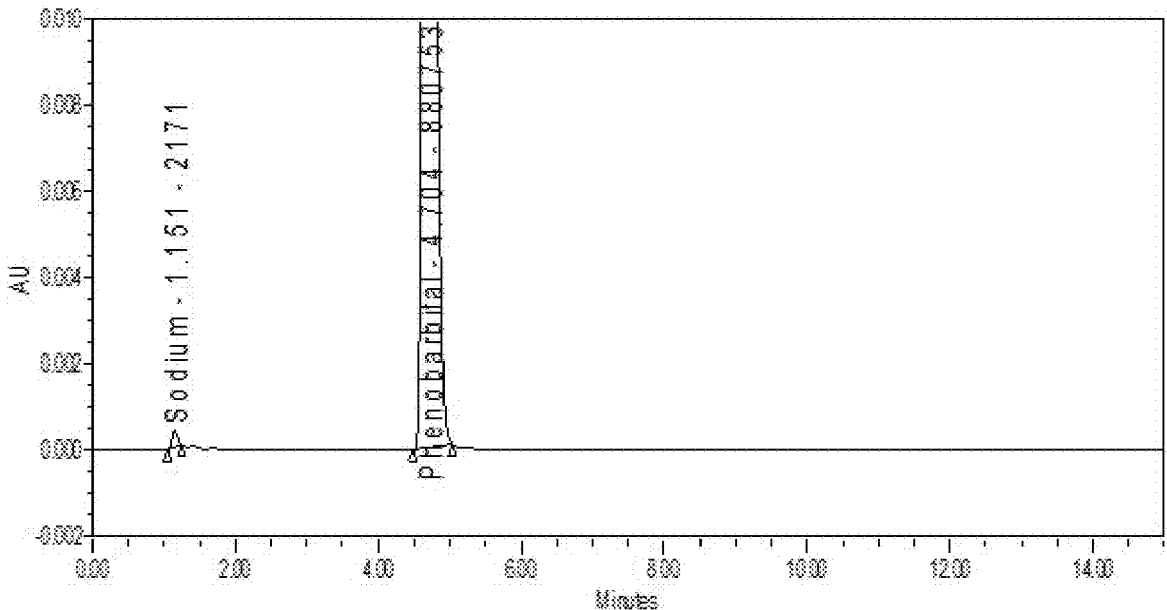
FIG. 4G is a chromatogram from an injection of the disclosed reconstituted lyophilized formulation of Phenobarbital Sodium at 130 mg/mL at initial time point for assay by HPLC at a detection wavelength of 254 nm, according to embodiments of the present invention.
Figure 4H:
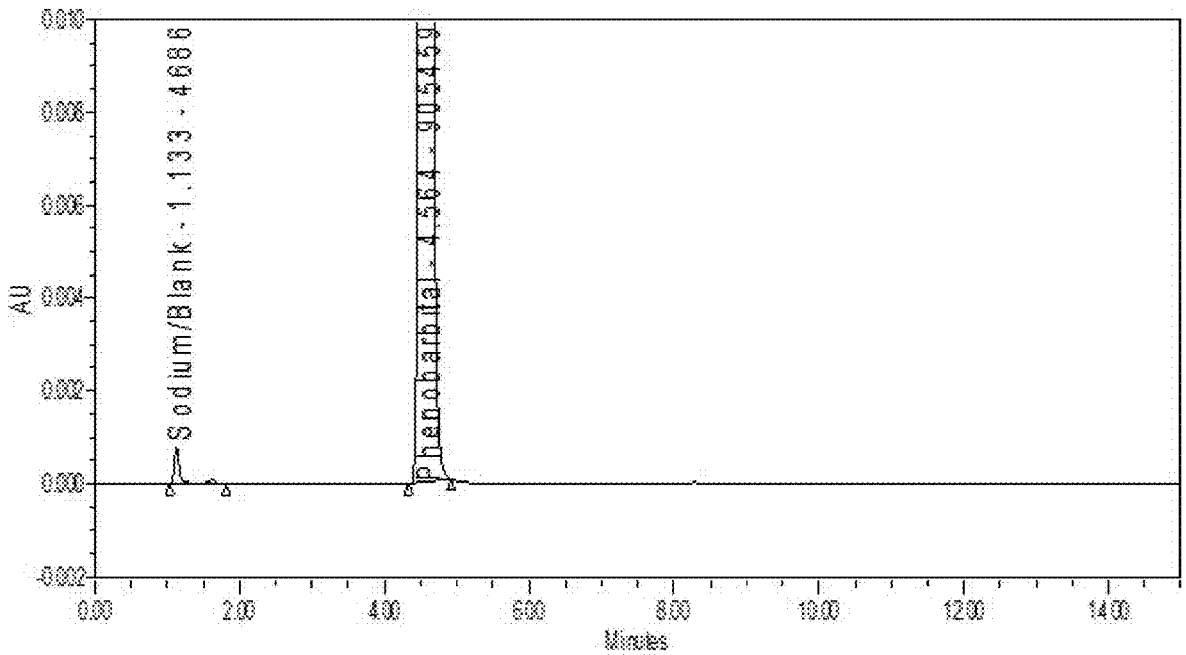
FIG. 4H is a chromatogram from an injection of the disclosed reconstituted lyophilized formulation of Phenobarbital Sodium at 130 mg/mL at 6 months from initial time point at room temperature (RT) for assay by HPLC at a detection wavelength of 254 nm, according to embodiments of the present invention.
Figure 4I:
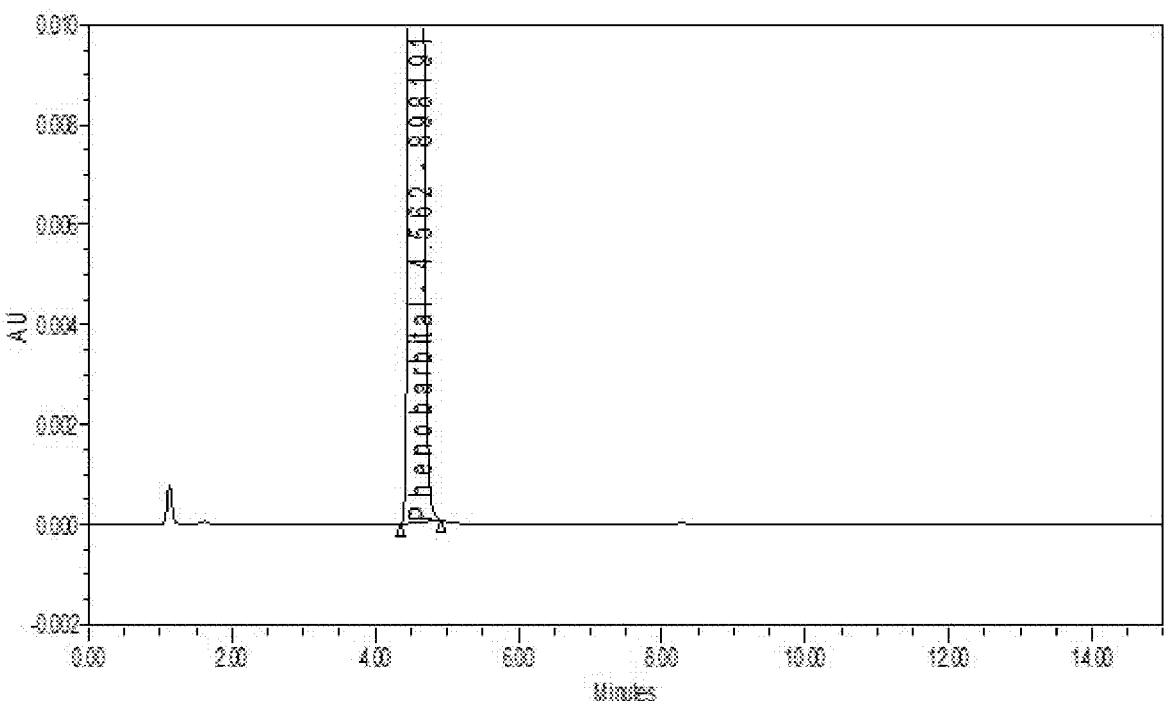
FIG. 4I is a chromatogram from an injection of the disclosed reconstituted lyophilized formulation of Phenobarbital Sodium at 130 mg/mL at 6 months from initial time point at accelerated stability conditions (ACC) for assay by HPLC at a detection wavelength of 254 nm, according to embodiments of the present invention.
Figure 4J:
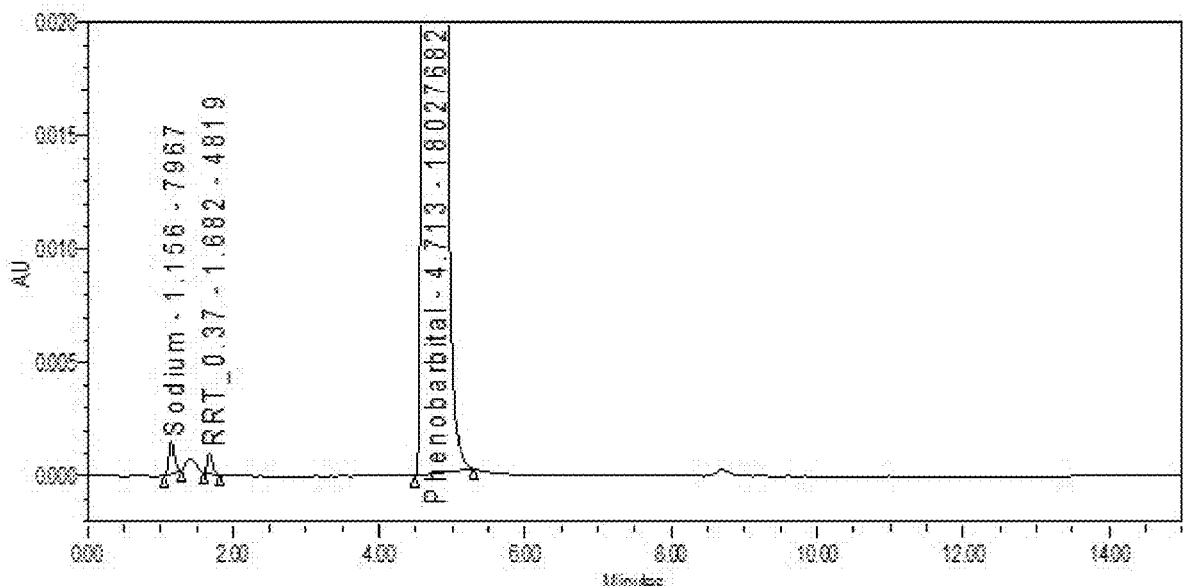
FIG. 4J is a chromatogram from an injection of the disclosed reconstituted lyophilized formulation of Phenobarbital Sodium at 130 mg/mL at initial time point for related substances by HPLC at a detection wavelength of 210 nm, according to embodiments of the present invention.
Figure 4K:
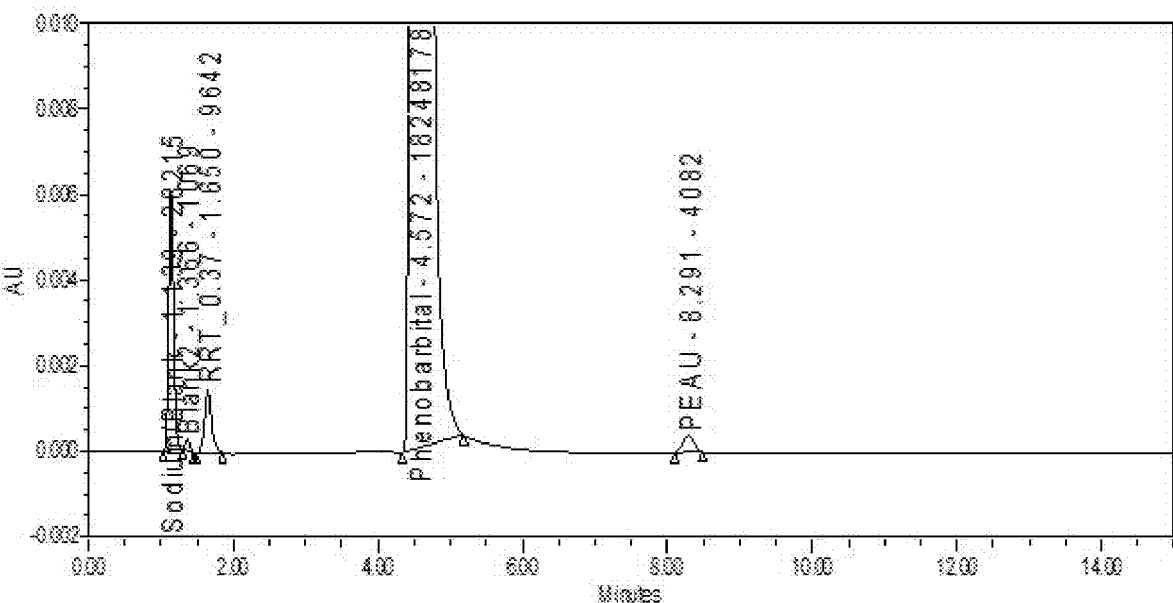
FIG. 4K is a chromatogram from an injection of the disclosed reconstituted lyophilized formulation of Phenobarbital Sodium at 130 mg/mL at 6 months from initial time point at room temperature (RT) for related substances by HPLC at a detection wavelength of 210 nm, according to embodiments of the present invention.
Figure 4L:
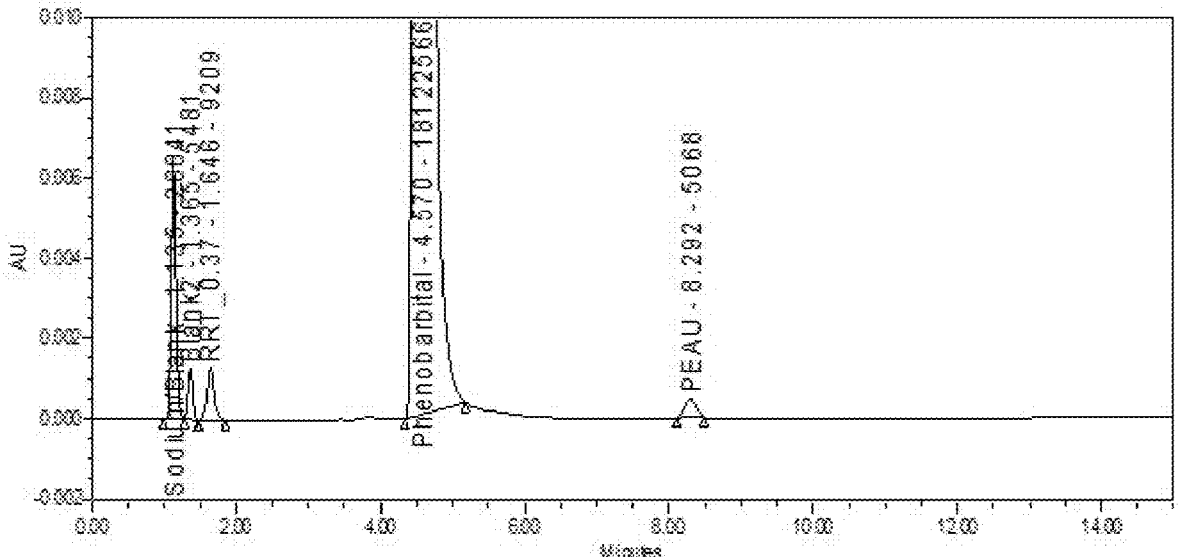
FIG. 4L is a chromatogram from an injection of the disclosed reconstituted lyophilized formulation of Phenobarbital Sodium at 130 mg/mL at 6 months from initial time point at accelerated stability conditions (ACC) for related substances by HPLC at a detection wavelength of 210 nm, according to embodiments of the present invention.
Figure 5A:
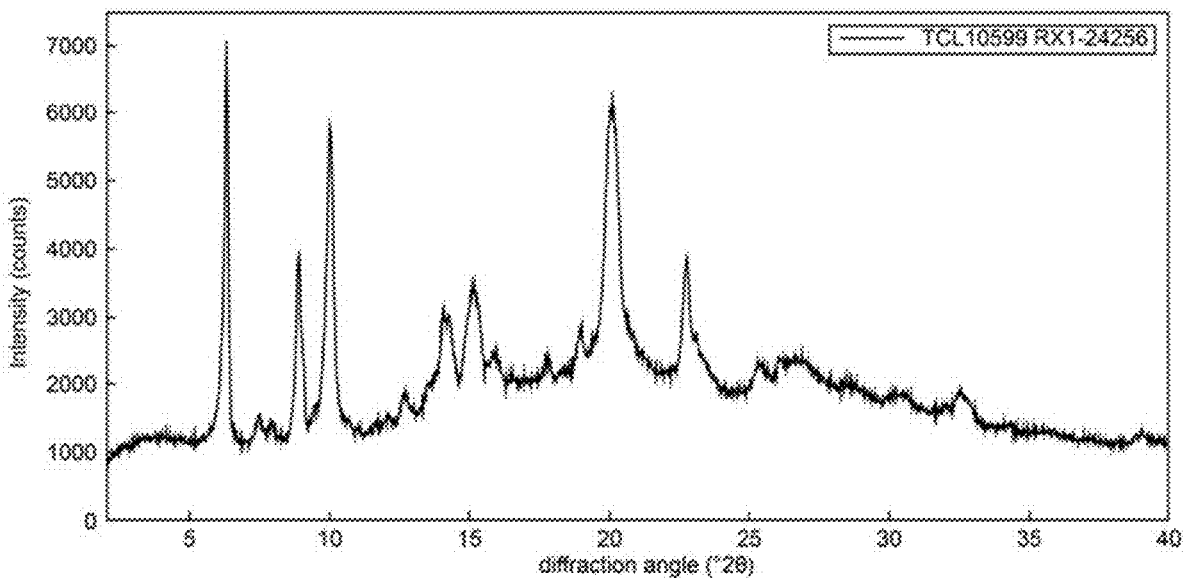
FIG. 5A is an X-ray powder diffraction (XRPD) pattern of Phenobarbital Sodium Grade P

The contemplated method for producing a storage-stable lyophilized Phenobarbital Sodium composition includes adding purified Phenobarbital Sodium to water. Preferably the purified Phenobarbital Sodium solid is purchased from a chemical supplier that adheres to the United States Pharmacopeia (USP) manufacturing and synthesis guidelines. The USP grade of the Phenobarbital Sodium is preferably USP "purified" or "practical" (P) grade indicating that it is a good quality chemical. As understood in the art, the USP grade (P) active pharmaceutical ingredient (API) of Phenobarbital Sodium is not suitable for administration because it is not sterile, is hygroscopic, and as such, maintaining anhydrous conditions of this grade of API is not feasible. Structurally, the analyzed USP grade P API is polymorphous—containing both crystalline and non-crystalline material. With reference to FIG. 5A, an X-ray powder diffraction (XRPD) pattern is shown of this compound.

Considering the need to avoid hydrolysis of the Phenobarbital Sodium, the Phenobarbital Sodium is preferably added to Water for Injection and later lyophilized to obtain a stable lyophilized finished product. In order to remove dissolved oxygen ($O_2$) gas from the water (e.g., Water for Injection), it is also preferred that the water is sparged with nitrogen ($N_2$) or other inert gas prior to the addition of the Phenobarbital Sodium solid. For effective sparging, a volume of about 100-200 ml water is sparged with nitrogen gas for at least 30 minutes. In exemplary protocols for producing either 65 mg, 130 mg of lyophilized Phenobarbital Sodium, 100 milliliters (ml) of Water for Injection is nitrogen sparged for 30 minutes. In additional embodiments, the water may also be cooled to approximately 2 to 8° C. In preferred embodiments, the water is cooled to approximately 2 to 8° C.

The addition of the Phenobarbital Sodium solid to the water (e.g., deionized nitrogen sparged water cooled to 2 to 8° C.) may be carried out using any suitable mixing. Preferably, the water (e.g., Water for Injection) is first added to a glass/stainless steel container for nitrogen sparging and cooling, and this prepped water remains in the glass/stainless steel container or a measured amount is transferred to a preferably weighed glass container/stainless steel container and the Phenobarbital Sodium solid is added thereto. For mixing, any suitable mixing may be used. For example, a magnetic stir bar may be added to the glass/stainless steel container. Upon addition of the Phenobarbital Sodium solid to the water, the mixture is stirred.

An additional consideration for stability of the Phenobarbital Sodium is maintaining a pH between 9.2 and 10.2 in the bulk solution of Phenobarbital Sodium. After dissolution of the Phenobarbital Sodium solid in the water, the pH is adjusted to within this range of 9.2 and 10.2. Accordingly, the pH of the water solubilized Phenobarbital Sodium is first measured upon dissolution. If the pH is higher than 10.2 or lower than 9.2, the pH is adjusted. For example, if necessary, the pH may be lowered to or between 9.2 and 10.2 using Hydrochloric acid (HCl) and the pH may be increased to or between 9.2 and 10.2 using Sodium Hydroxide (NaOH).

Following the pH measurement and any adjustment, the Phenobarbital Sodium solution is preferably filtered to remove any foreign particles. For example, the Phenobarbital Sodium solution may be filtered using a 0.2 μm (or 0.22 μm) membrane filter. For example, the membrane filter may be polyvinylidene difluoride (PVDF) or any other compatible filter membranes such as Polyethersulfone (PES) filter.

According to aspects of the contemplated method, the Phenobarbital Sodium solution dissolved in the water (e.g., nitrogen sparged Water for Injection cooled to 2 to 8° C.) having a pH of or between 9.2 and 10.2 and preferably filtered is ready for Lyophilization. Depending on the desired amount of the lyophilized Phenobarbital Sodium product, the Phenobarbital Sodium solution may be lyophilized in any amount or the solution may be aliquoted into sterile containers (e.g., vials). For example, in order to obtain a measured dose of lyophilized Phenobarbital Sodium in a container, the glass container, water, and Phenobarbital Sodium solid are weighed prior to mixing in order to determine an actual weight of the Phenobarbital Sodium after pH measurement and adjustment. For example, to produce 65 mg or 130 mg doses of lyophilized Phenobarbital Sodium, a batch may be dissolved, mixed, pH adjusted if necessary, and filtered and then aliquoted into single use dose vials for lyophilization. In a specific example, a 50 mL batch of Phenobarbital Sodium solution may be prepared where for 65 mg doses, 3.25 grams of Phenobarbital Sodium solid (e.g., USP Grade P) is added to 40 ml of water (e.g., nitrogen sparged Water for Injection cooled to 5 to 8° C.) and for 130 mg doses, 6.5 grams of the Phenobarbital Sodium is added to the 40 ml of water. Following dissolution, pH adjustment if necessary, adjusting final volume to 50.0 mL and filtering, 1 ml aliquots of this Phenobarbital Sodium solution are added to open (e.g., unstoppered) vials and then loosely stoppered (e.g., with lyophilization rubber stoppers) prior to lyophilization. Following lyophilization, each vial contains 65 mg or 130 mg of lyophilized Phenobarbital Sodium.

10

In further embodiments, following lyophilization, the vials may be completely closed (e.g., stoppered) under vacuum.

Another embodiment is directed to a pharmaceutical composition that consists of lyophilized amorphous Phenobarbital Sodium.

Another embodiment is directed to a method of producing a storage-stable form of lyophilized Phenobarbital sodium that forms no more than 0.2% phenylethylacetylurea (PEAU) when reconstituted in an aqueous solution. The method comprising: includes adding Phenobarbital Sodium to water to form a Phenobarbital Sodium solution, if necessary, adjusting the pH of the Phenobarbital Sodium solution to or between 9.2 to 10.2; and lyophilizing the Phenobarbital Sodium solution.

In one embodiment, the water is Water for Injection.

In another embodiment the Water for Injection is sparged with nitrogen prior to adding the Phenobarbital Sodium.

In another embodiment, the Water for Injection is sparged with nitrogen for at least 30 minutes prior to adding the Phenobarbital Sodium.

In another embodiment, the water is cooled to or between 2 to 8° C. prior to adding the Phenobarbital Sodium.

In another embodiment, the adjusting includes measuring the pH of the Phenobarbital Sodium solution, and if the pH is higher than 10.2, the adjusting includes adding Hydrochloric acid (HCl).

In another embodiment, the lyophilized Phenobarbital Sodium forms no more than 0.1% phenylethylacetylurea (PEAU) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium forms no more than 0.05% phenylethylacetylurea (PEAU) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium forms no detectable amount of 2-ethyl-2-phenylmalonamide (2EPMM) or alpha-phenylbutyrylguanidine (PBG) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium is stable up to at least 6 months at accelerated stability conditions (ACC) which is equivalent to 24 months at room temperature (RT).

In another embodiment, the stability of the lyophilized Phenobarbital Sodium is determined by adding the lyophilized Phenobarbital Sodium to an aqueous solution to form a reconstituted lyophilized Phenobarbital Sodium and analyzing to quantitate the amount of phenylethylacetylurea (PEAU), 2-ethyl-2-phenylmalonamide (2EPMM), and/or alpha-phenylbutyrylguanidine (PBG) in the reconstituted lyophilize Phenobarbital Sodium.

In another embodiment, the Phenobarbital Sodium solution is at a concentration of 65 mg/mL, 100 mg/mL, 130 mg/mL or 200 mg/mL.

In another embodiment, the method further includes filtering the Phenobarbital Sodium solution prior to lyophilizing.

In another embodiment, the method further includes aliquoting the Phenobarbital Sodium solution into a vial prior to lyophilization; and after lyophilization, applying a closure to the vial under vacuum.

Another embodiment is directed to a method of treating an individual in need of Phenobarbital Sodium. The method includes adding saline or dextrose to a composition containing lyophilized amorphous Phenobarbital Sodium immediately prior to administration to form a Phenobarbital Sodium solution; and administering the Phenobarbital Sodium solution to the individual.

In another embodiment, the individual suffers from epilepsy.

In another embodiment, the individual is a newborn suffering from neonatal epilepsy.

In another embodiment, the composition is a powder dose of 65 mg, 100, 130 mg or 200 mg.

In another embodiment, the administering includes intramuscular injection or intravenous injection.

Figure 5B:
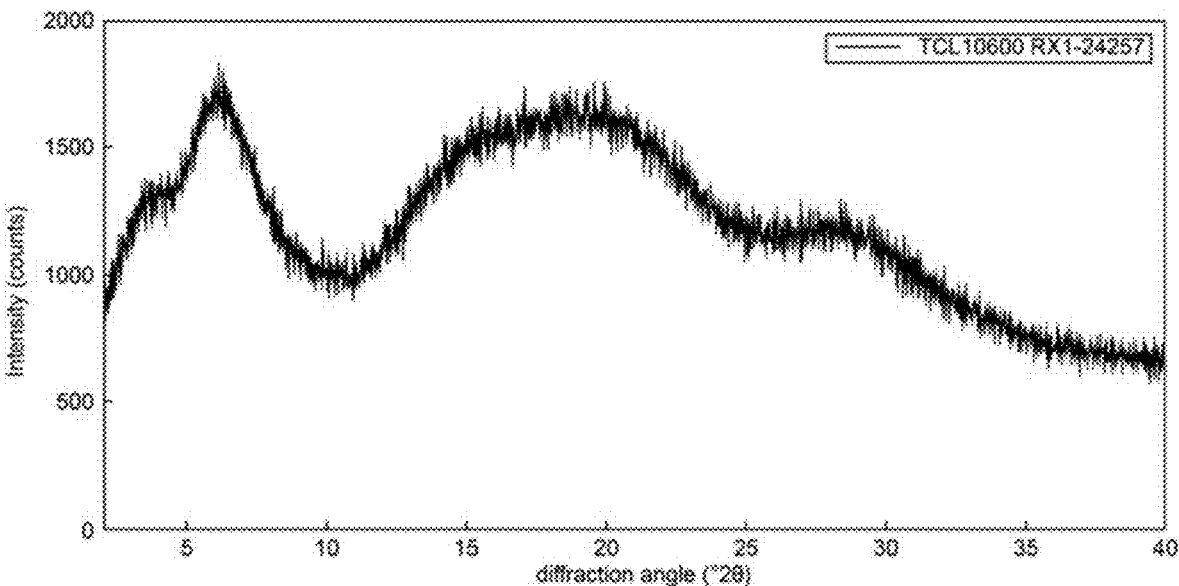
FIG. 5B is an XRPD pattern of Phenobarbital Sodium for Injection, USP, 65 mg/vial.
Figure 5C:
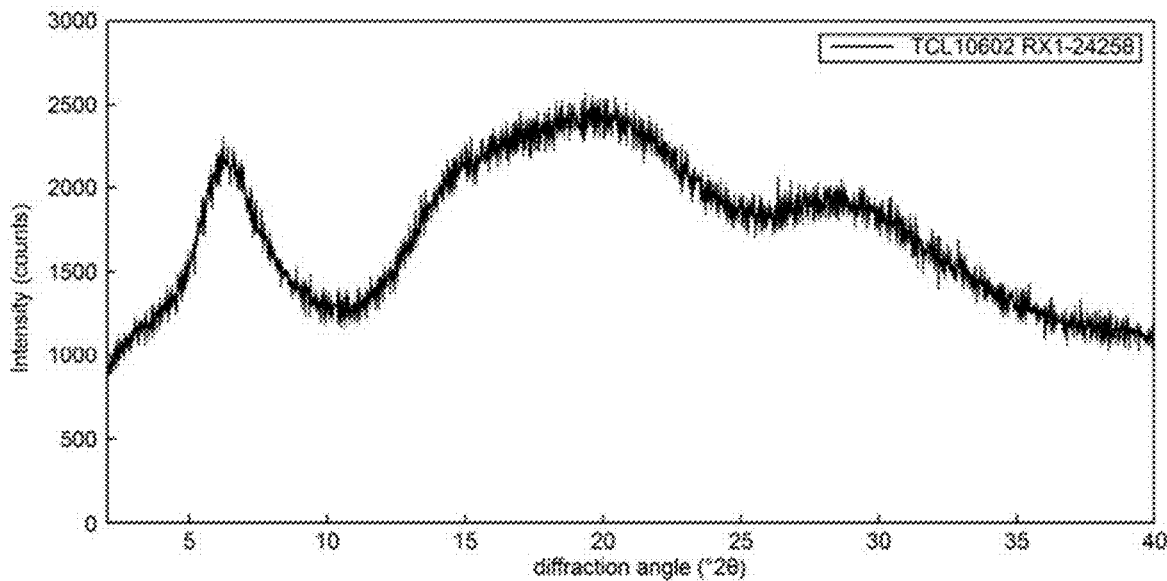
FIG. 5C is an XRPD pattern of Phenobarbital Sodium for Injection, USP, 130 mg/vial.
Figure 5D:
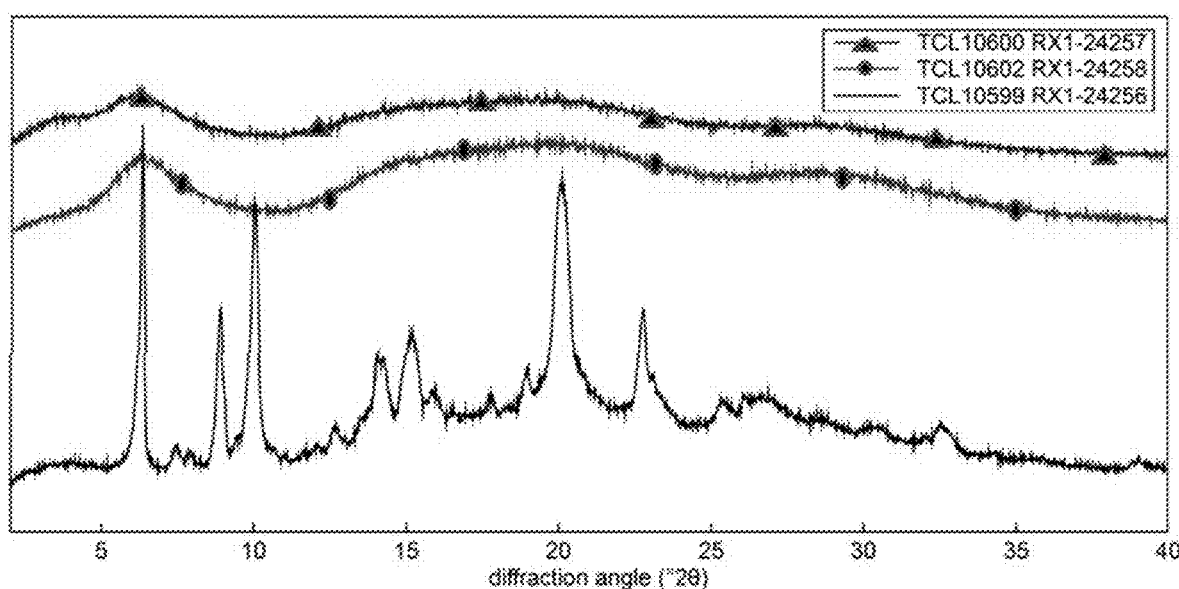
FIG. 5D is a stack plot of the XRPD patterns of FIGS. 5A, 5B, and 5C.

Surprisingly, the inventors have determined that the presently disclosed method produces a storage-stable lyophilized Phenobarbital Sodium that maintains its stability up to at least 6 months under accelerated stability conditions which is equivalent to 24 months at RT. With reference to FIGS. 5B-5C, the lyophilized Phenobarbital Sodium is amorphous. In particular, the lyophilized Phenobarbital Sodium is non-crystalline unlike the USP grade PAPI shown comparatively in FIG. 5D. The lyophilized Phenobarbital Sodium is stable and ready for reconstitution in either water for injection, 0.9% Saline or 5% Dextrose for intravenous (IV) or intramuscular (IM) administration. The presently disclosed formulation does not contain any organic solvents or preservatives which is specifically advantageous for administration to newborns and neonates. Moreover, the resulting lyophilized Phenobarbital Sodium forms below the quantitation limit of 0.05% phenylethylacetylurea (PEAU), and no detectable amount of 2-ethyl-2-phenylmalonamide (2EPMM) or alpha-phenylbutyrylguanidine (PBG) when reconstituted in water after storage of the lyophilized Phenobarbital Sodium for up to 6 months under accelerated stability conditions which is equivalent to 24 months at RT.

In a comparison analysis, the presently disclosed lyophilized powder of Phenobarbital Sodium at 65 mg or 130 mg doses was reconstituted in water and assayed for impurities and stability along with marketed liquid formulation of Phenobarbital Sodium for Injection USP, 65 mg/mL or 130 mg/mL (Westward Pharmaceuticals). The formulation details for this comparative analysis are presented in Table 1. Representative chromatograms from HPLC analysis are shown in FIGS. 2A-2H, 3A-3L, and 4A-4L.

TABLE 1

| | | Dosage form | |
| | | Liquid | Lyophilized |
| Components | Chemical name | mg/mL | mg/vial |
|---|---|---|---|
| Drug Substance | Phenobarbital Sodium | 65 or 130 | 65 or 130 |
| Inactive ingredients | Propylene Glycol | 705 | NA |
| | Benzyl alcohol | 15.6 | NA |
| | Ethanol | 78.9 | NA |
| | HCL | For pH adjustment | NA |
| | Water for Injection | QS (Quantity Supplied) | NA |

Lyophilized Phenobarbital Sodium for Injection USP, 65 mg/vial and 130 mg/vial
Liquid Phenobarbital Sodium for Injection USP, 65 mg/mL or 130 mg/mL With reference to Tables 2 and 3, the presently disclosed 65 mg lyophilized Phenobarbital Sodium composition was reconstituted in water and compared to the 65 mg Liquid Phenobarbital Sodium for Injection USP (65 mg/mL marketed Liquid Formulation) (Table 2) (FIGS. 3A-3F, FIGS. 4A-4F), and the presently disclosed 130 mg lyophilized Phenobarbital Sodium for Injection USP (130 mg/vial) composition was reconstituted in water and compared to the 130 mg liquid Phenobarbital Sodium for Injection USP (130 mg/mL marketed Liquid Formulation) (Table 3) (FIGS. 3G-3L, FIGS. 4G-4L). In addition to the noted characteristics of each product, the products were assayed for degradation products—phenylethylacetylurea (PEAU), 2-ethyl-2-phenylmalonamide (2EPMM), and alpha-phenylbutyrylguanidine (PBG) by HPLC analysis, as further described in the Examples. As indicated in both Tables 2 and 3, the initial amount of PEAU (phenylethylacetylurea) assayed in the 65 mg/mL and 130 mg/mL liquid formulations was 0.5% and 0.5%, respectively. Comparatively, no initial amount of PEAU was detected in either the 65 mg or 130 mg lyophilized Phenobarbital Sodium compositions. Furthermore, after 3 and 6 months from the date of manufacture, both the liquid and lyophilized formulations at 65 mg/mL and 130 mg/mL stored at room temperature (RT) (25° C.) and under accelerated stability conditions (ACC) at 40° C. were analyzed by HPLC for assay and related substances. Under these conditions, the amount of PEAU assayed in the 65 mg/mL liquid formulations at 3 months was 1.0% (RT) and 3.7% (ACC) and at 6 months was 1.4% (RT) and 5.8% (ACC) (Table 2). Similarly, the amount of PEAU assayed in 130 mg/mL liquid formulations at 3 months was 0.9% (RT) and 2.8% (ACC) and at 6 months was 1.1% (RT) and 4.3% (ACC) (Table 3). In contrast, for the presently disclosed lyophilized compositions, the amount of PEAU assayed at 3 and 6 months for the 65 mg and the 130 mg lyophilized Phenobarbital Sodium compositions was below quantitation limit (BQL) (0.05%) both at RT and ACC stability conditions (Tables 2-3).

TABLE 2

| | | | | | 65 mg/ml Liquid Formulation and 65 mg/vial Lyophilized Powder | | | | | |
|---|---|---|---|---|---|---|---|---|---|---|
| | | | | | Product Name | | | | | |
| | | Phenobarbital Sodium for Injection USP, 65 mg/mL (Marketed product) | | | | Phenobarbital Sodium for Injection USP, 65 mg/Vial (Nivagen formulation- NPH1907) | | | | |
| | | | | | Formulation Type | | | | | |
| | | | Liquid | | | | Lyophilized powder | | | |
| | | | | | Stability Data | | | | | |
| | | 3 Months | | 6 Months | | | 3 Months | | 6 Months | | 15 Months |
| Test | Initial | RT 25° C., 60% RH | ACC 40° C., 75% RH | RT 25° C., 60% RH | ACC 40° C., 75% RH | Initial | RT 25° C., 60% RH | ACC 40° C., 75% RH | RT 25° C., 60% RH | ACC 40° C., 75% RH | RT** 25° C., 60% RH |
|---|---|---|---|---|---|---|---|---|---|---|---|
| Description | CCVS | CCVS | CCVS | CCVS | CCVS | WLP | WLP | WLP | WLP | WLP | WLP |
| Appearance after reconstitution | NA | NA | NA | NA | NA | CCS | CCS | CCS | CCS | CCS | CCS |
| Identification | $ | $ | $ | $ | $ | $ | $ | $ | $ | $ | $ |
| pH* | 9.3 | 9.8 | 9.7 | 9.6 | 9.6 | 9.8 | 9.6 | 9.6 | 9.7 | 9.7 | 9.8 |
| % Assay of Phenobarbital Sodium | 102.4 | 97.6 | 103.1 | 96.3 | 86.7 | 99.1 | 98.7 | 97.4 | 100.0 | 99.3 | 96.0 |
| % degradation (Area percent) 2EPMM | ND | ND | BQL | BQL | BQL | ND | ND | ND | ND | ND | ND |
| PBG | ND | ND | ND | ND | ND | ND | ND | ND | ND | ND | ND |
| PEAU | 0.5 | 1.0 | 3.7 | 1.4 | 5.8 | ND | BQL | BQL | BQL | BQL | BQL |
| Any unspecified degradation product | BQL | BQL | 0.1 | BQL | 0.3 | BQL | BQL | BQL | 0.07 | 0.06 | 0.04 |
| Total degradation products | 0.5 | 1.0 | 3.8 | 1.4 | 6.1 | BQL | BQL | BQL | 0.07 | 0.06 | 0.04 |

CCVS: Clear Colorless Viscous Solution;
CCS: Clear Colorless Solution;
WLP: White Lyophilized powder
$: In Assay analysis, the retention time of Phenobarbital in standard and sample solutions should be same.
BQL: Below Quantitation Limit; (QL-0.05%);
ND: Not Detected
2EPMM: 2-Ethyl-2-Phenylmalonamide, monohydrate;
PBG: α-phenylbutyrylguanidine,
PEAU: phenylethylacetylurea or Pheneturide
*pH of both liquid and lyophilized formulations are measured at 65 mg/mL concentration
**The samples were stored at 30 ± 2° C., 65% RH ± 5
Notably, the Lyophilized powder was stable even after 15 months, and no significant increase in the impurities was observed, rendering such formulation superior to known liquid formulations and enable easy administration.

TABLE 3

| | | | | | 130 mg/mL Liquid Formulation and 130 mg/vial Lyophilized formulation | | | | | |
|---|---|---|---|---|---|---|---|---|---|---|
| | | | | | Product Name | | | | | |
| | | Phenobarbital Sodium for Injection USP, 130 mg/mL (Marketed product) | | | | Phenobarbital Sodium for Injection USP, 130 mg/vial (Nivagen formulation-NPH1912) | | | | |
| | | | | | Formulation Type | | | | | |
| | | | Liquid | | | | Lyophilized powder | | | |
| | | | | | Stability Data | | | | | |
| | | 3 Months | | 6 Months | | | 3 Months | | 6 Months | | 15 Months |
| Test | Initial | RT 25° C., 60% RH | ACC 40° C., 75% RH | RT 25° C., 60% RH | ACC 40° C., 75% RH | Initial | RT 25° C., 60% RH | ACC 40° C., 75% RH | RT 25° C., 60% RH | ACC 40° C., 75% RH | RT** 25° C., 60% RH |
|---|---|---|---|---|---|---|---|---|---|---|---|
| Description | CCVS | CCVS | CCVS | CCVS | CCVS | WLP | WLP | WLP | WLP | WLP | WLP |
| Appearance after | NA | NA | NA | NA | NA | CCS | CCS | CCS | CCS | CCS | CCS |

TABLE 3-continued

| | | | | | | | | | | |
|---|---|---|---|---|---|---|---|---|---|---|
| 130 mg/mL Liquid Formulation and 130 mg/vial Lyophilized formulation | | | | | | | | | | |
| Product Name | | | | | | | | | | |
| Phenobarbital Sodium for Injection USP, 130 mg/mL (Marketed product) | | | | | Phenobarbital Sodium for Injection USP, 130 mg/vial (Nivagen formulation-NPH1912) | | | | | |
| Formulation Type | | | | | | | | | | |
| Liquid | | | | | Lyophilized powder | | | | | |
| Stability Data | | | | | | | | | | |
| | | 3 Months | | 6 Months | | | 3 Months | | 6 Months | | 15 Months |
| Test | Initial | RT 25° C., 60% RH | ACC 40° C., 75% RH | RT 25° C., 60% RH | ACC 40° C., 75% RH | Initial | RT 25° C., 60% RH | ACC 40° C., 75% RH | RT 25° C., 60% RH | ACC 40° C., 75% RH | RT** 25° C., 60% RH |
| reconstitution Identification | $ | $ | $ | $ | $ | $ | $ | $ | $ | $ | $ |
| pH* | 9.5 | 9.9 | 9.9 | 9.8 | 9.7 | 9.8 | 9.8 | 9.8 | 9.8 | 9.8 | 10.0 |
| % Assay of Phenobarbital Sodium | 100.8 | 95.5 | 92.9 | 95.2 | 90.9 | 98.3 | 100.1 | 97.9 | 100.2 | 99.4 | 98.3 |
| Related Substances (% Area) 2EPMM | ND | ND | BQL | BQL | BQL | ND | ND | ND | ND | ND | ND |
| PBG | ND | ND | ND | ND | ND | ND | ND | ND | ND | ND | ND |
| PEAU | 0.5 | 0.9 | 2.8 | 1.1 | 4.3 | ND | BQL | BQL | BQL | BQL | BQL |
| Any unspecified degradation product | ND | BQL | 0.1 | BQL | 0.4 | BQL | BQL | BQL | 0.05 | 0.05 | 0.04 |
| Total degradation products | 0.5 | 0.9 | 2.9 | 1.1 | 4.7 | BQL | BQL | BQL | 0.05 | 0.05 | 0.04 |

CCVS: Clear Colorless Viscous Solution;
CCS: Clear Colorless Solution;
WLP: White Lyophilized powder
$: In Assay analysis, the retention time of Phenobarbital in standard and sample solutions should be same.
BQL: Below Quantitation Limit; (QL-0.05%);
ND: Not Detected
2EPMM: 2-Ethyl-2-Phenylmalonamide, monohydrate;
PBG: α-phenylbutyrylguanidine,
PEAU: phenylethylacetylurea or Pheneturide
*pH for liquid formulation is measured at 130 mg/mL and for lyophilized formulation at 100 mg/mL dilution
**The samples were stored at 30 ± 2° C., 65% RH ± 5

In typical embodiments, the method of reducing formation of degradation products of a lyophilized Phenobarbital Sodium composition reconstituted in water results in the reconstituted solution having no less than 96% Phenobarbital Sodium. In more typical embodiments, the reconstituted solution has no less than 97% Phenobarbital Sodium. In more preferred embodiments, the reconstituted solution has no less than 98% Phenobarbital Sodium. In additional or alternative embodiments, the reconstituted solution has no quantitative amount (e.g., 0.05% or less) of PEAU, 2 EPMM, or PBG.

According to contemplated embodiments, assaying the stability of the lyophilized Phenobarbital Sodium composition includes reconstituting the composition in water at a concentration of 65 mg/mL, 100 mg/mL, 130 mg/mL or 200 mg/mL.

Further aspects of the present disclosure include methods of treating an individual in need of Phenobarbital Sodium. For administration to an individual (e.g., a human patient) the lyophilized powder of Phenobarbital Sodium powder may be reconstituted in saline or dextrose as disclosed herein immediately prior to administration to form a Phenobarbital Sodium reconstituted solution. In particular embodiments, the individual in need of Phenobarbital Sodium suffers from epilepsy. In preferred embodiments, the individual in need of Phenobarbital Sodium is a newborn suffering from neonatal epilepsy. In other embodiments, the lyophilized Phenobarbital Sodium is a powder dose of 65 mg, 100 mg, 130 mg or 200 mg. In typical embodiments, the administering of the Phenobarbital Sodium reconstituted solution to the individual includes intramuscular injection or intravenous injection.

EXAMPLES

Lyophilization Microscopy. Lyophilization microscopy (FIGS. 1A-1F) was performed using a Leica DM LP microscope equipped with a Linkam FDCS196 stage, TMS93 controller, vacuum pump, LNP unit, and a Spot Insight color camera. A 20×, 040 N.A. objective was used with crossed polarizers and a first order red compensator to view sample. Images were acquired using Spot Advanced software (v.4.5.9).

Lyophilization parameters for the lyophilization microscopy including a start temperature of –50° C. with heating at 1° C./minute to –40° C. followed by heating at 0.5° C./minute to –32.0° C.

HPLC Assays. High Performance Liquid Chromatography (HPLC) was used to assay Phenobarbital Sodium standards and sample solutions as disclosed herein (e.g., Tables 2, 3, FIGS. 3A-3L, and 4A-4L). Both Ultra High-Performance Liquid Chromatographic system (UHPLC) and High-Performance Liquid Chromatographic system (HPLC) (ThermoFisher/Waters) were used together with Data Acquisition Software (Empower 3), equipped with UV and Photodiode Array Detector (UV and PDA), column thermostat and auto sampler compartments or equivalent HPLC system and software.

An exemplary HPLC assay protocol is provided in the following:

Instruments/Apparatus: HPLC with UV detector/PDA Detector, Analytical balance, Sonicator, Volumetric flasks, Beakers, Pipettes.

Reagents, Solvents, Standards: Phenobarbital Reference Standard, Deionized water/Water for Injection, Potassium Monobasic Phosphate, Acetonitrile.

Preparation of Mobile Phase Solutions: Potassium phosphate monobasic (7 mM) and Acetonitrile (70:30) pH 4.5-6.5; Diluent: Mobile phase as a diluent.

Wash Solvent: Water:Acetonitrile (70:30)

CHROMATOGRAPHIC CONDITIONS: The liquid chromatography equipped with a

| Parameters | Conditions |
|---|---|
| Column | L7 packaging column, 150 × 4.6 mm, Particle Size: 5 μm or equivalent |
| Flow rate | 0.9-1.2 mL/min. |
| Detection Wavelength | 254 ± 2 nm for assay and 210 ± 2 nm for Related Substances |
| Injection volume | 10 μL |
| Run time | 15 Minutes |
| Column Oven Temperature | 30° C. |
| Sampler Cooler Temperature | 25° C. |
| Retention Time | About 5 minutes for Phenobarbital |
| Pump Mode | Isocratic |

UV and PDA detector, an injector and a data processor is operated as follows:

Phenobarbital Assay Standard Solution: 0.2 mg/mL to 0.8 mg/mL in diluent; Phenobarbital Related Substances Standard Solution: 0.26 μg/mL to 15.6 μg/mL in diluent; Phenobarbital Related Substances resolution standard solution: 0.475 mg/mL Phenobarbital and about 1 μg/mL for related substances (2-Ethyl-2-Phenyl malonamide, monohydrate (2EPMM), Phenylbutyrylguanidine (PBG) and Phenylethylacetylurea (PEAU) in diluent; Phenobarbital Sodium Sample Solution for Assay: 0.26 mg/mL to 0.78 mg/mL in diluent Phenobarbital Sodium related Substances sample solution: 0.52 mg/mL of Phenobarbital Sodium and related substances 2-Ethyl-2-Phenylmalonamide, monohydrate (2EPMM), Phenyl butyrylguanidine (PBG) and Phenylethylacetylurea (PEAU) and any unspecified degradation products at 0.26 μg/mL to 13.2 μg/mL SYSTEM SUITABILITY REQUIREMENTS: The relative standard deviation of Phenobarbital peak from Six replication injections of related substances standard should not be more than 6.0%. The related standard deviation of Phenobarbital peak from five replicate injections in assay standard solution should not be more than 2.0%. Tailing factor for the Phenobarbital is not more than 2.0. USP Plate count for the Phenobarbital is not less than 2500. The S/N Ratio of the Sensitivity Standard Solution is NLT 10 for related substance test. The resolution between Phenobarbital peak and nearest impurity peak is NLT 1.5

Two alternative formulations are disclosed in Table 6. One of these formulations is 200 mg/vial, Phenobarbital Sodium reconstituted in 10 mL of Water for Injection or 5% Dextrose to obtain a concentration of 20 mg/mL. A second formulation is 200 mg/vial of Phenobarbital Sodium along with 90 mg Sodium Chloride reconstituted in 10 mL of Water for Injection to obtain a concentration of 20 mg/mL Phenobarbital Sodium for Injection and 9 mg/mL or 0.9% Sodium Chloride.

TABLE 6

Phenobarbital Sodium for Injection, USP, 200 mg/vial in 10 mL vial. Formulation Details.

| Ingredients | NPH2031 A (Bulk Solution at 100 mg · mL Phenobarbital Sodium) Compounding at 2-8° C. | | NPH2031 A (Bulk Solution at 100 mg · mL Phenobarbital Sodium and 45 mg/mL Sodium Chloride) Compounding at 2-8° C. Fill Volume: 2.1 mL | |
|---|---|---|---|---|
| | mg/mL (after reconstitution) | mg/vial | mg/mL (after reconstitution) | mg/vial |
| Phenobarbital Sodium | 20 | 200 | 20 | 200 |
| Sodium Chloride | NA | NA | 9 | 90 |
| WFI/DI Water | qs | qs | qs | qs |

Reconstitution Volume 10 mL; Diluents that can be used are Water for Injection, 0.9% Saline or 5% Dextrose.

These formulations along with the previously disclosed formulations were developed to enable physicians and medical staff at hospitals to easily reconstitute to a desired concentration (e.g., 20 mg/mL) and administer the medicine to patients in need thereof. The reconstituted solution is stable at 2-8° C. for 24 hrs and 3 to 4 hrs when stored at RT (see e.g., Tables 7, 8 and 9).

TABLE 7

Reconstituted Solution Stability of Phenobarbital Sodium for Injection USP, 200 mg/vial (NPH2031A Phenobarbital Sodium @ 200 mg/vial) (Reconstitution in 10 mL Water)

| Test | Spec. | Initial DOA: Jun. 5, 2020 | Reconstituted Solution Stability after 20 hrs DOA: Jun. 6, 2020 | |
|---|---|---|---|---|
| | | | 2-8° C. | RT |
| Description | WLP | WLP | WLP | WLP |
| Appearance | CCS | CCS | CCS | CCS |
| pH (20 mg/mL) | 9.2-10.2 | 9.9 | 9.7 | 9.8 |

TABLE 7-continued

Reconstituted Solution Stability of Phenobarbital Sodium for Injection USP, 200 mg/vial
(NPH2031A Phenobarbital Sodium @ 200 mg/vial) (Reconstitution in 10 mL Water)

| Test | Spec. | Initial DOA: Jun. 5, 2020 | Reconstituted Solution Stability after 20 hrs DOA: Jun. 6, 2020 | |
| --- | --- | --- | --- | --- |
| | | | 2-8° C. | RT |
| % Assay Phenobarbital Sodium | 90.0-105.0 | 100.1 | 100.1 | 100.1 |
| Related Substances (% Area) 2EPMM | NMT 0.2% | BQL | ND | ND |
| PBG | NMT 0.2% | ND | ND | ND |
| PEAU | NMT 0.2% | BQL | 0.03 | 0.03 |
| Any unspecified degradation product | NMT 0.2% | BQL | 0.06 | 0.24 |
| Total degradation products | NMT 1.5% | BQL | 0.09 | 0.27 |
| Water Content by Karl Fischer | NMT 3.0% | 0.84 | NA | NA |
| Note Book Reference | | 192045-163 to 189 | 192045- 163-183 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 8

Reconstituted Solution Stability of Phenobarbital Sodium
for Injection USP, 200 mg/vial in Sodium Chloride (NPH2031B
Phenobarbital Sodium @ 200 mg/vial and Sodium Chloride
@ 90 mg/vial) (Reconstitution in 10 mL Water)

| Test | Specification | Initial | Reconstituted Solution Stability after 20 hrs | |
| --- | --- | --- | --- | --- |
| | | | 2-8° C. | RT |
| Description Appearance | WLP CCS | WLP CCS | WLP CCS | WLP CCS |
| pH (20 mg/mL) | 9.2-10.2 | 9.8 | 9.7 | 9.8 |
| % Assay Phenobarbital Sodium | 90.0-105.0 | 103.3 | 103.4 | 102.8 |
| Related Substances (% Area) 2EPMM | NMT 0.2% | BQL | ND | BQL |
| PBG | NMT 0.2% | ND | ND | ND |
| PEAU | NMT 0.2% | BQL | 0.03 | 0.03 |
| Any unspecified degradation product | NMT 0.2% | BQL | 0.06 | 0.27 |

TABLE 8-continued

Reconstituted Solution Stability of Phenobarbital Sodium
for Injection USP, 200 mg/vial in Sodium Chloride (NPH2031B
Phenobarbital Sodium @ 200 mg/vial and Sodium Chloride
@ 90 mg/vial) (Reconstitution in 10 mL Water)

| Test | Specification | Initial | Reconstituted Solution Stability after 20 hrs | |
| --- | --- | --- | --- | --- |
| | | | 2-8° C. | RT |
| Total degradation products | NMT 1.5% | BQL | 0.09 | 0.3 |
| Water Content by Karl Fischer | NMT 3.0% | 0.84 | NA | NA |

WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 9

Reconstituted Solution Stability of Phenobarbital Sodium for Injection
USP, 130 mg/vial (NPH2030) (20 mg/mL dilution In Water)

| Tests | Shelf life Specifications | Initial | Time | | | | | |
| --- | --- | --- | --- | --- | --- | --- | --- | --- |
| | | | 2 hrs | | 4 hrs | | 24 hrs | |
| | | | 2-8 C. | RT | 2-8 C. | RT | 2-8 C. | RT |
| Appearance | CCS | CCS | CCS | CCS | CCS | CCS | CCS | CCS |
| pH (20 mg/mL dilution) | 9.2-10.2 | 9.5 | 9.5 | 9.6 | 9.6 | 9.5 | 9.6 | 9.5 |
| Assay of Phenobarbital Sodium | 90.0%-105.0% | 99.8 | 102.1 | 100.8 | 101.7 | 101.2 | 100.4 | 100.3 |

TABLE 9-continued

Reconstituted Solution Stability of Phenobarbital Sodium for Injection
USP, 130 mg/vial (NPH2030) (20 mg/mL dilution In Water)

| Tests | Shelf life Specifications | Initial | Time | | | | | |
|---|---|---|---|---|---|---|---|---|
| | | | 2 hrs | | 4 hrs | | 24 hrs | |
| | | | 2-8 C. | RT | 2-8 C. | RT | 2-8 C. | RT |
| Related Substances (% Area) 2EPMM | NMT 0.2% | ND | ND | ND | ND | ND | ND | BQL |
| PBG | NMT 0.2% | ND | ND | ND | ND | ND | ND | ND |
| PEAU | NMT 0.2% | BQL | BQL | BQL | BQL | BQL | BQL | BQL |
| Any unspecified degradation product @ RRT 0.37 | NMT 0.2% | 0.015 | 0.02 | 0.04 | 0.02 | 0.06 | 0.04 | 0.18 |
| Total degradation products | NMT 1.5% | 0.015 | 0.02 | 0.04 | 0.02 | 0.06 | 0.04 | 0.18 |
| Osmolality mOsmol/Kg | To be reported | 158 | NP | NP | NP | NP | 159 | 158 |

CCS: Clear colourless solution;
ND: Not detected;
BQL: Below Quantitation limit,
NP: Not performed;
2EPMM: 2-ethylphenylmalonamide monohydrate;
PBG: Phenylbutyrylguanidine;
PEAU: Phenylethylacetylurea Six months stability data for Phenobarbital Sodium for Injection, USP, 65 mg/vial is included in Table 10. Six months stability data for Phenobarbital Sodium for Injection, USP, 130 mg/vial is included in Table 11. Three months stability data for Phenobarbital Sodium for Injection, USP, 200 mg/vial is included in Table 12. Three months stability data for Phenobarbital Sodium for Injection, USP (Phenobarbital Sodium and 9% Saline), 200 mg/vial is included in Table 13.

TABLE 10

Product Name Phenobarbital Sodium for Injection USP, 65 mg/vial
Batch#NPH2020 Fill Volume: 1.05 mL Date Manufactured: Jan. 20, 2020
Vial Make 2 mL Clear Glass Vial: 13 mm Lyo rubber stopper; Seal: 13 mm Flip off plastic with Al seal.
API: Phenobarbital Sodium, USP Grade P
Configuration Inverted Stability 25° C., 60% RH (RT) & 40° C., 75% RH (ACC)

| Test | Spec. | Initial DOA: Feb. 18, 2020 | 1 Month DOA: Mar. 23, 2020 | | 3 Months DOA: May 20, 2020 | | 6 Months DOA: Sep. 4, 2020 | |
|---|---|---|---|---|---|---|---|---|
| | | | RT | ACC | RT | ACC | RT | ACC |
| Description | WLP | WLP | WLP | WLP | WLP | WLP | WLP | WLP |
| Appearance | CCS | CCS | CCS | CCS | CCS | CCS | CCS | CCS |
| pH (65 mg/mL) | 9.2-10.2 | 9.9 | 9.9 | 9.9 | 9.9 | 9.9 | 9.6 | 9.6 |
| % Assay Phenobarbital Sodium | 90.0%-105.0% | 98.6 | 101.6 | 101.5 | 101.3 | 100.5 | 100.0 | 101.2 |
| Related Substances (% Area) 2EPMM | NMT 0.2% | BQL | ND | ND | ND | ND | ND | ND |
| PBG | NMT 0.2% | ND | ND | ND | ND | ND | ND | ND |
| PEAU | NMT 0.2% | BQL | BQL | BQL | BQL | BQL | BQL | BQL |
| Any unspecified degradation product | NMT 0.2% | BQL | BQL | BQL | BQL | BQL | BQL | BQL |
| Total degradation products | NMT 1.5% | BQL | BQL | BQL | BQL | BQL | BQL | BQL |

TABLE 10-continued

Product Name Phenobarbital Sodium for Injection USP, 65 mg/vial
Batch#NPH2020 Fill Volume: 1.05 mL Date Manufactured: Jan. 20, 2020
Vial Make 2 mL Clear Glass Vial: 13 mm Lyo rubber stopper; Seal: 13 mm Flip off plastic with Al seal.
API: Phenobarbital Sodium, USP Grade P
Configuration Inverted Stability 25° C., 60% RH (RT) & 40° C., 75% RH (ACC)

| | | Initial DOA: | 1 Month DOA: Mar. 23, 2020 | | 3 Months DOA: May 20, 2020 | | 6 Months DOA: Sep. 4, 2020 | |
| --- | --- | --- | --- | --- | --- | --- | --- | --- |
| Test | Spec. | Feb. 18, 2020 | RT | ACC | RT | ACC | RT | ACC |
| Water Content by Karl Fischer | NMT 3.0% | 0.6 | 0.9 | 1.3 | 1.4 | 1.5 | 1.5 | 2.1 |
| Note Book Reference | | 192039-150 to 158 | 192045- 23 to 45 | | 192045-135 to 153 | | 192051-84 to 122 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea;

TABLE 11

Product Name Phenobarbital Sodium for Injection USP, 130 mg/vial
Batch#NPH2021 Fill Volume: 1.05 mL Date Manufactured: Jan. 20, 2020
Vial Make 2 mL Clear Glass Vial Date Initiated: Feb. 14, 2020
API Mfg. Phenobarbital Sodium, USP Grade P, Re test Date: Nov. 16, 2023
Stopper Used 13 mm Grey Rubber stopper Flip Off Seals: 13 mm Plastic with Aluminum Seal
Configuration Inverted Stability 25° C., 60% RH (RT) & 40° C., 75% RH (ACC)

| | | Initial DOA: | 1 Month DOA: Mar. 23, 2020 | | 3 Months DOA: May 20, 2020 | | 6 Months DOA: Sep. 4, 2020 | | 24 Months DOA: 18 Mar. 2022 |
| --- | --- | --- | --- | --- | --- | --- | --- | --- | --- |
| Test | Spec. | Feb. 18, 2020 | RT | ACC | RT | ACC | RT | ACC | RT |
| Description | WLP | WLP | WLP | WLP | WLP | WLP | WLP | WLP | WLP |
| Appearance | CCS | CCS | CCS | CCS | CCS | CCS | CCS | CCS | CCS |
| pH (100 mg/mL) | 9.2-10.2 | 10.0 | 10.0 | 10.0 | 10.0 | 10.0 | 9.7 | 9.7 | 9.8 |
| % Assay Phenobarbital Sodium | 90.0%-105.0% | 100.3 | 99.7 | 99.3 | 100.0 | 99.6 | 99.1 | 98.3 | 99.8 |
| Related Substances 2EPMM | NMT 0.2% | BQL | ND | ND | ND | ND | ND | ND | ND |
| PBG | NMT 0.2% | ND | ND | ND | ND | ND | ND | ND | ND |
| PEAU | NMT 0.2% | BQL | BQL | BQL | BQL | BQL | BQL | BQL | BQL |
| Any unspecified degradation product | NMT 0.2% | BQL | BQL | BQL | BQL | BQL | BQL | BQL | BQL |
| Total degradation products | NMT 1.5% | BQL | BQL | BQL | BQL | BQL | BQL | BQL | BQL |
| Water Content by Karl Fischer | NMT 3.0% | 0.7 | 0.7 | 0.9 | 0.9 | 1.1 | 1.0 | 1.3 | 1.4 |
| Note Book Reference | | 192039-150 to 158 | 192045- 23 to 45 | | 192045-135 to 151 | | 192051-84 to 122 | | 192099- 157, 159, 167, 170 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea;

TABLE 12

Product Name Phenobarbital Sodium for Injection USP, 200 mg/vial
Batch#NPH2031A Fill Volume: 2.1 mL Date Manufactured: Jun. 3, 2020
Vial Make 10 mL Tubular Serum Bottle clear Date Initiated: Jun. 9, 2020
API Mfg. Phenobarbital Sodium, USP Grade P, C-IV:,
Stopper Used 20 mm Igloo Bromobutyl Lyophilization
Rubber stopper Flip Off Seals: 20 mm Red Plastic
top flip off with Aluminum Seal, Lot#224203
Configuration Inverted Stability 25° C.,
60% RH (RT) & 40° C., 75% RH (ACC)

|  |  | Initial DOA: | 3 Months DOA: Sep. 4, 2020 | |
| --- | --- | --- | --- | --- |
| Test | Spec. | Jun. 5, 2020 | RT | ACC |
| Description | WLP | WLP | WLP | WLP |
| Appearance | CCS | CCS | CCS | CCS |
| pH (20 mg/mL) | 9.2-10.2 | 9.9 | 9.6 | 9.7 |
| % Assay Phenobarbital Sodium | 90.0-105.0 | 100.1 | 98.1 | 101.0 |
| Related Substances (% Area) 2EPMM | NMT 0.2% | ND | ND | ND |
| PBG | NMT 0.2% | ND | ND | ND |
| PEAU | NMT 0.2% | BQL | BQL | BQL |
| Any unspecified degradation product @RRT 0.37 | NMT 0.2% | BQL | 0.06 | 0.05 |

TABLE 12-continued

Product Name Phenobarbital Sodium for Injection USP, 200 mg/vial
Batch#NPH2031A Fill Volume: 2.1 mL Date Manufactured: Jun. 3, 2020
Vial Make 10 mL Tubular Serum Bottle clear Date Initiated: Jun. 9, 2020
API Mfg. Phenobarbital Sodium, USP Grade P, C-IV:,
Stopper Used 20 mm Igloo Bromobutyl Lyophilization
Rubber stopper Flip Off Seals: 20 mm Red Plastic
top flip off with Aluminum Seal, Lot#224203
Configuration Inverted Stability 25° C.,
60% RH (RT) & 40° C., 75% RH (ACC)

|  |  | Initial DOA: | 3 Months DOA: Sep. 4, 2020 | |
| --- | --- | --- | --- | --- |
| Test | Spec. | Jun. 5, 2020 | RT | ACC |
| Total degradation products | NMT 1.5% | BQL | 0.06 | 0.05 |
| Water Content by Karl Fischer | NMT 3.0% | 1.1 | 1.0 | 1.3 |
| Note Book Reference |  | 192045-163 to 189 | 192051- 84 to 122 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 13

Product Name Phenobarbital Sodium for Injection USP, 200 mg/vial (Phenobarbital Sodium
and 9% Saline/vial) Batch#NPH2031B Fill Volume: 2.1 mL Date Manufactured: Jun. 3, 2020
Vial Make 10 mL Tubular Serum Bottle clear Date Initiated: Jun. 9, 2020
API Mfg. Phenobarbital Sodium, USP Grade P, C-IV Re test Date: Jul. 20, 2024
Stopper Used 20 mm Lyophilization Rubber stopper Flip Off Seals:
20 mm Red Plastic top flip off with Aluminum Seal
Configuration Inverted Stability 25° C., 60% RH (RT) & 40° C., 75% RH (ACC)

|  |  | Initial DOA: | 3 Months DOA: Sep. 4, 2020 | | 6 Months DOA: Dec. 11, 2020 | | 12 months DOA: 11 Apr. 2022 |
| --- | --- | --- | --- | --- | --- | --- | --- |
| Test | Spec. | Jun. 5, 2020 | RT | ACC | RT | ACC | RT |
| Description | WLP | WLP | WLP | WLP | WLP | WLP | WLP |
| Appearance | CCS | CCS | CCS | CCS | CCS | CCS | CCS |
| pH (20 mg/mL) | 9.2-10.2 | 9.8 | 9.5 | 9.5 | 9.6 | 9.6 | 9.5 |
| % Assay Phenobarbital Sodium | 90.0-105.0 | 103.3 | 102.8 | 103.6 | 104.0 | 103.7 | 99.9 |
| Related Substances (% Area) 2EPMM | NMT 0.2% | BQL | ND | ND | ND | ND | ND |
| PBG | NMT 0.2% | ND | ND | ND | ND | ND | ND |
| PEAU | NMT 0.2% | BQL | BQL | BQL | BQL | 0.05 | (BQL) |
| Any unspecified degradation product @RRT 0.37 | NMT 0.2% | BQL | 0.06 | 0.05 | 0.06 | 0.05 | (BQL) |
| Total degradation products | NMT 1.5% | BQL | 0.06 | 0.05 | 0.06 | 0.10 | BQL |
| Water Content by Karl Fischer | NMT 4.0% | 0.8 | 0.9 | 1.1 | NP | NP | 1.2 |
| Note Book Reference |  | 192045-163 to 189 | 192051- 84 to 122 | | 192067-78 to 88 | | 192034-137 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea Data for Osmolality, Particulate matter and assay for Sodium Chloride is disclosed in Table 14.

TABLE 14

| | Osmolality* (mOsmol/Kg) (Specification: | Particulate Matter (By Light Obscuration method) Ref: USP<788> | | Assay of Sodium Chloride (titrimetric; Ref USP monograph |
|---|---|---|---|---|
| Batch No | To be reported) Reconstitution in 10 mL (20 mg/mL) | ≥10 μM Specification: (NMT 6000 particles/vial) | ≥25 μM Specification: (NMT 600 particles/vial | for Sodium Chloride Injection Specification: (95.0%-105.0%) |
| NPH2031A (200 mg/vial) | 148 | 80.0 | 0.67 | NA |
| NPH2031B (200 mg/vial) (Phenobarbital Sodium 200 mg, 9% Sodium Chloride) | 372 | 171 | 1.33 | 99.99 |
| Water -Blank | 0 | NA | NA | NA |
| 0.9% Sodium Chloride | 270 | NA | NA | NA |

Phenobarbital Sodium for Injection, USP, 200 mg/vial in Water or Sodium Chloride - Osmolality, Particulate Matter and Assay for Sodium Chloride.

Lyophilization parameters used for the 65 mg/vial, 100 mg/vial, 130 mg/vial and 200 mg/vial are disclosed in Table 15.

TABLE 15

Lyophilization Cycle parameters.

| | | Lyophilization Cycle 1* | | | | Lyophilization Cycle 2** | | | |
|---|---|---|---|---|---|---|---|---|---|
| Section | Phase | Condenser set point C. | Vacuum [mTorr] | Temperature ° C. | Hold Time [mm] | Condenser set point ° C. | Vacuum [mTorr] | Temperature ° C. | Hold Time [mm] |
| 1 | Loading | | off | 5 | n.a. | | off | −5 | n.a. |
| 2 | Freezing | | off | −5 | 5 | | off | −5 | 10 |
| 3 | Freezing | | off | −50 | 60 | | off | −52 | 120 (Ramp) |
| 4 | Freezing | | off | −10 | 30 | | off | −52 | 180 (Hold) |
| 5 | Freezing | | off | −50 | 120 | | n.a. | n.a. | n.a. |
| 6 | Evacuation | −50 | 75 | −50 | 30 | −60 | 50 | −45 | 30 |
| 7 | Primary drying | | 75 | −50 | 400 (Hold) | | 50 | −42 | 100 (Ramp) |
| 8 | Primary drying | | 75 | −45 | 350 (Hold) | | 50 | −42 | 1120 (Hold) |
| 9 | Primary drying | | 75 | −43 | 300 (Hold) | | n.a. | n.a. | n.a. |
| 10 | Primary drying | | 75 | −35 | 250 (Hold) | | n.a. | n.a. | n.a. |
| 11 | Primary drying | | 75 | −20 | 60 (Hold) | | n.a. | n.a. | n.a. |
| 12 | Primary drying | | 75 | 0 | 120 (Hold) | | n.a. | n.a. | n.a. |
| 13 | secondary drying | | 75 | 50 | 120 (Hold) | | 50 | 35 | 100 (Ramp) |
| 14 | secondary drying | | 75 | 25 | 120 (Hold) | | 50 | 35 | 420 (Hold) |

Lyophilization Cycle 1*: 65 mg/vial, 130 mg/vial and 100 mg/vial samples disclosed in Tables 1, 2, 3, 16 and 17

Lyophilization Cycle 2**: NPH2031A (200 mg/vial Phenobarbital Sodium) and NPH2031B (200 mg/vial in Phenobarbital Sodium and 90 mg/vial Sodium Chloride, NPH2020 (65 mg/vial) and NPH2021 (130 mg/vial)

65

Six months stability data for Phenobarbital Sodium for Injection USP, 100 mg/vial is included in Table 16.

TABLE 16

Product Name Phenobarbital Sodium for Injection USP, 100 mg/vial Batch#NPH1980 Fill Volume: 1.0 mL Date Manufactured: Sep. 25, 2019
Vial Make 5 mL Clear Untreated 5 mL Clear Treated Date Initiated: Sep. 30, 2019
API Mfg. Phenobarbital Sodium, USP Grade P, C-IV:, Re test Date:
Stopper Used 13 mm Grey Bromobutyl 2 leg Lyophilization Rubber stopper Flip Off Seals: 13 mm Red Plastic top flip off with Aluminum Seal
Configuration Inverted Stability 25° C., 60% RH (RT) & 40° C., 75% RH (ACC)

| | | Initial DOA: Sep. 27, 2019 | | 1 Month DOA: Oct. 31, 2019 | | | | 3 Months DOA: Jan. 10, 2020 | | | | 6 Months DOA: Apr. 8, 2020 | | | |
| | | | | RT | | ACC | | RT | | ACC | | RT | | ACC | |
| Test | Spec. | UT | T | UT | T | UT | T | UT | T | UT | T | UT | T | UT | T |
|---|---|---|---|---|---|---|---|---|---|---|---|---|---|---|---|
| Description | WLP | WLP | WLP | WLP | WLP | WLP | WLP | WLP | WLP | WLP | WLP | WLP | WLP | WLP | WLP |
| Appearance | CCS | CCS | CCS | CCS | CCS | CCS | CCS | CCS | CCS | CCS | CCS | CCS | CCS | CCS | CCS |
| pH (100 mg/mL) | 9.2-10.2 | 9.7 | 9.7 | 9.6 | 9.7 | 9.6 | 9.6 | 9.7 | 9.7 | 9.7 | 9.7 | 9.8 | 9.9 | 9.8 | 9.9 |
| % Assay Phenobarbital Sodium | 90.0%-105.0% | 98.4 | 97.6 | 98.6 | 99.0 | 99.0 | 100.4 | 99.1 | 99.7 | 97.0 | 96.9 | 97.7 | 98.3 | 97.2 | 97.6 |
| % Impurity 2EPMM | NMT 0.2% | ND | ND | ND | ND | ND | ND | BQL | BQL | BQL | BQL | ND | ND | ND | ND |
| PBG | NMT 0.2% | ND | ND | ND | ND | ND | ND | ND | ND | ND | ND | ND | ND | ND | ND |
| PEAU | NMT 0.2% | BQL | BQL | BQL | BQL | BQL | BQL | BQL | BQL | BQL | BQL | BQL | BQL | BQL | BQL |
| Any unspecified degradation product | NMT 0.2% | 0.06 | 0.06 | 0.05 | 0.05 | 0.05 | 0.05 | BQL | BQL | BQL | BQL | BQL | BQL | BQL | BQL |
| Total Impurities | NMT 2.0% | 0.06 | 0.06 | 0.05 | 0.05 | 0.05 | 0.05 | BQL | BQL | BQL | BQL | BQL | BQL | BQL | BQL |
| Water Content by Karl Fischer | NMT 3.0% | 0.7 | 0.6 | 1.0 | 0.9 | 1.1 | 1.3 | 1.2 | 1.1 | 1.6 | 1.4 | 1.6 | 1.2 | 1.5 | 2.0 |
| Note Book Reference | | 192031-91 to 101 | | 192031-169 to 183 | | | | 192039-44 to 52 | | | | 192045-36 to 85 | | | |

DOA: Date of Analysis
WLP: White Lyophilized powder;
CCS: Clear Colorless Solution, 1 minute after reconstitution;
UT: Untreated;
T: Treated
ND: Not Detected;
NMT: Not More Than;
BQL: Below Quantitation Limit (0.05%)
2EPMM: 2-Ethyl-2-Phenylmalonamide, monohydrate;
PBG: $\alpha$-Phenylbutyrylguanidine;
PEAU: Phenylethylacetylurea

TABLE 17

Phenobarbital Sodium for Injection,
USP, 100 mg/vial Formulation Details.

| Ingredients | NPH1980 (Bulk Solution at 100 mg · mL Phenobarbital Sodium) Compounding at 2-8° Fill Volume 1.0 mL | | |
| | mg/mL (after reconstitution) | mg/vial | Batch Quantity (100 mL) |
|---|---|---|---|
| Phenobarbital Sodium | 20 | 100 | 10.113 g |
| WFI/DI Water | qs | qs | Qs to 100 mL or 103.3 g |

Diluents that can be used: Water for Injection, 0.9% Saline or 5% Dextrose
Proposed Reconstitution Volume: 5 mL Representative chromatograms and/or corresponding calculations are shown in FIGS. 2A-2H, 3A-3L, 4A-4L, and Tables 2 and 3.

The results for further extended stability studies are presented below in which commercially available phenobarbital sodium, USP Grade P was dissolved in water to produce an aqueous solution having a pH of between 9.2 and 10.2, and in which the aqueous solution was then filled into lyophilization vials in an amount of between 65 mg per vial and 200 mg per vial at a maximum concentration of phe-nobarbital of 100 mg/ml. Lyophilization was performed as in Table 15 noted above. Stability studies were then performed at standard conditions (RT: 25° C., 60% relative humidity) and accelerated conditions (ACC: 40° C., 75% relative humidity) for a period of up to 37 months.

After the storage conditions indicated in the tables below, the lyophilized product was then dissolved in water (or saline or dextrose) and subjected to analysis for degradation products of phenobarbital. Specifically, the inventors investigated the levels of degradation by quantifying the remaining phenobarbital and by quantifying 2-ethyl-2-phenylmalonamide (2EPMM), alpha-phenylbutyrylguanidine (PBG), and phenylethylacetylurea (PEAU), as well as other unspecified degradation products. Remarkably, and as can be seen from the data below, the lyophilized amorphous phenobarbital had a storage stability at 25° C. and 60% relative humidity for up to and beyond three years and did readily dissolve upon reconstitution.

Table 18 depicts exemplary results for 65 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained below quantitation limit (0.05%).

TABLE 18

| (65 mg/vial, up to 24 months) | | | | | | | | |
|---|---|---|---|---|---|---|---|---|

| Product Name | Phenobarbital Sodium for Injection USP, 65 mg/vial | | Batch# NPH2020 Fill Volume: 1.05 mL | | Date Manufactured: Jan. 20, 2020 | | | |
|---|---|---|---|---|---|---|---|---|
| Vial Make | 2 mL Fiolax Clear Blow Back Vial | | | | Date Initiated: Feb. 14, 2020 | | | |
| API Mfg. | | Phenobarbital Sodium, USP Grade P, C-IV: | | | | | | |
| Stopper Used | | 13 mm Grey Bromobutyl 2 leg Lyophilization Rubber stopper | | Flip Off Seals: 13 mm Red Plastic top flip off with Aluminum Seal | | | | |
| Configuration | Inverted | Stability | | 25° C., 60% RH (RT) & 40° C., 75% RH (ACC) | | | | |

| Test | Spec. | Initial DOA: Feb. 18, 2020 | 1 Month DOA: Mar. 23, 2020 | | 3 Months DOA: May 20, 2020 | | 6 Months DOA: Sep. 4, 2020 | | 24 Months DOA: Mar. 18, 2022 |
|---|---|---|---|---|---|---|---|---|---|
| | | | RT | ACC | RT | ACC | RT | ACC | RT |
| Description | WLP | WLP | WLP | WLP | WLP | WLP | WLP | WLP | WLP |
| Appearance | CCS | CCS | CCS | CCS | CCS | CCS | CCS | CCS | CCS |
| pH (65 mg/mL) | 9.2-10.2 | 9.9 | 9.9 | 9.9 | 9.9 | 9.9 | 9.6 | 9.6 | 9.7 |
| % Assay Phenobarbital Sodium | 90.0%-105.0% | 98.6 | 101.6 | 101.5 | 101.3 | 100.3 | 100.0 | 101.2 | 101.2 |
| Related Substances 2EPMM | NMT 0.2% | BQL | ND | ND | ND | ND | ND | ND | ND |
| PBG | NMT 0.2% | ND | ND | ND | ND | ND | ND | ND | ND |
| PEAU | NMT 0.2% | BQL | BQL | BQL | BQL | BQL | BQL | BQL | BQL |
| Any unspecified degradation product | NMT 0.2% | BQL | BQL | BQL | BQL | BQL | BQL | BQL | BQL |
| Total degradation products | NMT 1.5% | BQL | BQL | BQL | BQL | BQL | BQL | BQL | BQL |
| Water Content by Karl Fischer | NMT 3.0% | 0.7 | 0.9 | 1.3 | 1.4 | 1.5 | 1.6 | 2.1 | 1.8 |
| Note Book Reference | | 192039-150 to 158 | 192045-23 to 45 | | 192045-135 to 151 | | 192051-84 to 122 | | 192099-157, 159, 167,170 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea;

Table 19 depicts exemplary results for 65 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained below quantitation limit (0.05%) or barely above quantitation limit.

TABLE 19

| (65 mg/vial, up to 37 months) | | | |
|---|---|---|---|

| Product Name | Phenobarbital Sodium for Injection USP, 65 mg/vial | Batch# NPH1907 | Date Manufactured: Feb. 21, 2019 |
|---|---|---|---|
| Vial Make | 2 mL Fiolax Clear Blow Back Vial | | Date Initiated: Feb. 25, 2019 |

TABLE 19-continued (65 mg/vial, up to 37 months)

| Test | | | 1 Month DOA: Mar. 28, 2019 | | 3 Months DOA: May 24, 2019 | | 6 Months DOA: Aug. 28, 2019 | | 15 Months DOA: Jun. 12, 2020 | 37 Months |
|---|---|---|---|---|---|---|---|---|---|---|
| API Mfg. Stopper Used | | | 13 mm Grey Bromobutyl 2 leg Lyophilization Rubber stopper | Phenobarbital Sodium, USP Grade P, C-IV: | | | Flip Off Seals: 13 mm Red Plastic top flip off with Aluminum Seal | | | |
| Configuration | | | Inverted Stability | | | | 25° C. ± 2° C., 60% RH ± 5% (RT) & 40° C., ± 2° C., 75% RH ± 5% (ACC) | | | |
| | Initial DOA: Spec. | RT | ACC | RT | ACC | RT | ACC | RT | *RT | **RT |
| Description | White to almost white lyophilized poweder | * | * | * | * | * | * | * | * | |
| Appearance | CCS | CCS | CCS | CCS | CCS | CCS | CCS | CCS | CCS | |
| pH (65 mg/mL | 9.2-10.2 | 9.8 | 10.0 | 10.1 | 9.6 | 9.6 | 9.7 | 9.7 | 9.8 | |
| % Assay Phenobarbital Sodium | NMT 0.2% | ND | ND | ND | ND | ND | ND | ND | ND | |
| Related Substances 2EPMM | NMT 0.2% | ND | ND | ND | ND | ND | ND | ND | ND | |
| PBG | NMT 0.2% | ND | ND | ND | ND | ND | ND | ND | ND | |
| PEAU | NMT 0.2% | ND | BQL | BQL | BQL | BQL | BQL | BQL | BQL | |
| Any unspecified degredation product | NMT 0.2% | BQL | BQL | BQL | BQL | BQL | 0.07 | 0.06 | 0.04 | |
| Total dedregation products | NMT 1.5% | BQL | BQL | BQL | BQL | BQL | 0.07 | 0.06 | 0.04 | |
| Water Content by Karl Fischer | NMT 3.0% | 0.8 | 1.1 | 1.5 | 1.6 | 1.7 | 1.2 | 2.2 | 2.0 | |
| Note Book Reference | 192019-41,44,45,47 | 192019-122,123,126,127 | | 192025-25,30,31,34 | | 192031-8,12,14,16,17,18 | | 192051-2 to 11 | | |

DOA: Date of Analysis
WLP: White Lyophilized Powder,
CCS: Clear Colorless Solution, 1 minute after reconstitution;

Table 20 depicts exemplary results for 100 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained below quantitation limit (0.05%) or barely above quantitation limit.

TABLE 20

(100 mg/vial, up to 30 months)

| | | | | |
|---|---|---|---|---|
| Product Name | | Phenobarbital Sodium for Injection USP, 100 mg/vial | Batch# NPH1980 Fill Volume: 1.0 mL | Date Manufactured: Sep. 25, 2019 |
| Vial Make | | 2 mL Clear Untreated 5 mL Clear Treated | | Date Initiated: Sep. 30, 2019 |
| API Mfg. Stopper Used | | 13 mm Grey Bromobutyl 2 leg Lyophilization Rubber stopper | Phenobarbital Sodium, USP Grade P, C-IV: Flip Off Seals: 13 mm Red Plastic top flip off with Aluminum Seal | |
| Configuration | Inverted | Stability 25° C., | | 60% RH (RT) & 40° C., 75% RH (ACC) |
| | | | 1 Month DOA: Oct. 31, 2019 | 3 Months DOA: Jan. 10, 2020 |
| | Initial DOA: Sep. | | | |

TABLE 20-continued

| | | (100 mg/vial, up to 30 months) | | | | | | | | | |
|---|---|---|---|---|---|---|---|---|---|---|---|
| | | 27, 2019 | | RT | | ACC | | RT | | ACC | |
| Text | Spec. | UT | T | UT | T | UT | T | UT | T | UT | T |
| De-scription | WLP | WLP | WLP | WLP | WLP | WLP | WLP | WLP | WLP | WLP | WLP |
| Ap-pearance | CCS | CCS | CCS | CCS | CCS | CCS | CCS | CCS | CCS | CCS | CCS |
| pH (100 mg/mL) | 9.2-10.2 | 9.7 | 9.7 | 9.6 | 9.7 | 9.6 | 9.6 | 9.7 | 9.7 | 9.7 | 9.7 |
| % Assay of Pheno-barbital | 90.0%-105.0% | 98.4 | 97.6 | 98.6 | 99.0 | 98.0 | 100.4 | 99.1 | 98.7 | 97.0 | 96.9 |
| % Impurity 2EPMM | NMT 0.2% | ND | ND | ND | ND | ND | ND | BQL | BQL | BQL | BQL |
| PBG | NMT 0.2% | ND | ND | ND | ND | ND | ND | ND | ND | ND | ND |
| PEAU | NMT 0.2% | BQL | BQL | ND | ND | BQL | BQL | BQL | BQL | BQL | BQL |
| Any un-specified de-gradation product @ RRT0.37 | NMT 0.2% | 0.06 | 0.06 | 0.05 | 0.0 | 0.05 | 0.05 | BQL | BQL | BQL | BQL |
| Total Impurities | NMT 1.5% | 0.06 | 0.06 | 0.05 | 0.05 | 0.05 | 0.05 | BQL | BQL | BQL | BQL |
| Water Content by Karl Fischer | NMT 4.0% | 0.7 | 0.6 | 1.0 | 0.9 | 1.1 | 1.1 | 1.2 | 1.1 | 1.6 | 1.4 |
| Note Book Reference | | 192031-91 to 101 | | | | 192031-169 to 183 | | | | 192039-44 to 52 | |

| | | 6 Months DOA: | | | | 30 Months DOA: | |
|---|---|---|---|---|---|---|---|
| | | Apr. 8, 2020 | | | | Mar. 18, 2022 | |
| | | RT | | ACC | | RT | |
| Text | Spec. | UT | T | UT | T | UT | T |
| De-scription | WLP | WLP | WLP | WLP | WLP | WLP | WLP |
| Ap pearance | CCS | CCS | CCS | CCS | CCS | CCS | CCS |
| pH (100 mg/mL) | 9.2-10.2 | 9.8 | 9.9 | 9.8 | 9.9 | 9.6 | 9.6 |
| % Assay of Pheno-barbital | 90.0%-105.0% | 97.7 | 98.3 | 97.2 | 97.6 | 99.2 | 100.0 |
| % Impurity 2EPMM | NMT 0.2% | BQL | BQL | BQL | BQL | BQL | BQL |
| PBG | NMT 0.2% | ND | ND | ND | ND | ND | ND |
| PEAU | NMT 0.2% | BQL | BQL | BQL | BQL | BQL | BQL |
| Any un-specified de-gradation product @ RRT0.37 | NMT 0.2% | BQL | BQL | BQL | BQL | BQL | BQL |
| Total Impurities | NMT 1.5% | BQL | BQL | BQL | BQL | BQL | BQL |
| Water | NMT 4.0% | 1.6 | 1.2 | 1.5 | 2.0 | 2.1 | 1.8 |

TABLE 20-continued

| (100 mg/vial, up to 30 months) | | |
|---|---|---|
| Content by Karl Fischer | | |
| Note Book Reference | 192045-46 to 85 | 192039- 157, 159, 170157, 159, 167, 170 |

DOA: Date of Analysis;
WLP: White Lyophilized Powder;
CCS: Clear Colorless Solution, 1 minute after reconstitution;
UT: Untreated;
T: Treated
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea Table 21 depicts exemplary results for 130 mg per vial [20] phenobarbital sodium stored at standard and accelerated conditions where under all tested conditions 2EPMM, PBG, and PEAU remained undetectable or below quantitation limit (0.05%). Likewise, unspecified degradation products and total degradation products remained at or below quantitation limit (0.05%).

TABLE 21

| (130 mg/vial, up to 37 months) | | | | | | | |
|---|---|---|---|---|---|---|---|
| Product Name | Phenobarbital Sodium for Injection USP, 130 mg/vial | | | Batch#NPH1912 | | Date Manufactured: Feb. 23, 2019 | |
| Vial Make | 2 mL Fiolax Clear Blow Back Vial | | | Date Initiated: Feb. 25, 2019 | | | |
| | API Mfg. | | | Phenobarbital Sodium, USP Grade P, C-IV: | | | |
| Stopper Used | 13 mm Grey Bromobutyl 2 leg Lyophilization Rubber stopper | | | Flip Off Seals: 13 mm Red Plastic top flip off with Aluminum Seal | | | |
| Config-uration | Inverted | | Stability | 25° C. ± 2° C., 60% RH ± 5% (RT) & 40° C., ± 2° C., 75% RH ± 5% (ACC) | | | |
| | | | | 1 Month DOA: Mar. 28, 2019 | | 3 Months DOA: May 24, 2019 | |
| | | Initial | | | | | |
| Test | Spec. | DOA: Feb. 28, 2019 | RT | ACC | | RT | ACC |
| Description | WLP | WLP | WLP | WLP | | WLP | WLP |
| Appearance | CCS | CCS | CCS | CCS | | CCS | CCS |
| pH (100 mg/mL) | 9.2-10.2 | 9.8 | 10.0 | 9.9 | | 9.7 | 9.7 |
| % Assay Pheno-barbital Sodium | 90.0%-105.0% | 98.3 | 97.1 | 98.3 | | 100.1 | 97.9 |
| Related Substances 2EPMM | NMT 0.2% | ND | ND | ND | | ND | ND |
| PBG | NMT 0.2% | ND | ND | ND | | ND | ND |
| PEAU | NMT 0.2% | ND | BQL | BQL | | BQL | BQL |
| Any unspecified degradation product | NMT 0.2% | BQL | BQL | BQL | | BQL | BQL |
| Total Degradation products | NMT 1.5% | BQL | BQL | BQL | | BQL | BQL |
| Water Content by Karl Fischer | NMT 4.0% | 0.6 | 1.1 | 1.2 | | 1.1 | 1.3 |
| Note Book Reference | | 192019- 41, 44, 45, 47 | 192019- 122, 123, 125, 126 | | | 192025- 24, 30, 31, 34 | |

TABLE 21-continued

| (130 mg/vial, up to 37 months) | | | | | |
|---|---|---|---|---|---|
| | | 6 Months DOA: Aug. 28, 2019 | | 15 Months DOA: Jun. 12, 2020 | 37 Months DOA: 18 Mar. 2022 |
| Test | Spec. | RT | ACC | RT | RT |
| Description | WLP | WLP | WLP | WLP | WLP |
| Appearance | CCS | CCS | CCS | CCS | CCS |
| pH (100 mg/mL) | 9.2-10.2 | 9.8 | 9.8 | 10.0 | 9.8 |
| % Assay Pheno-barbital Sodium | 90.0%-105.0% | 98.8 | 99.4 | 98.3 | 99.2 |
| Related Substances 2EPMM | NMT 0.2% | ND | ND | ND | ND |
| PBG | NMT 0.2% | ND | ND | ND | ND |
| PEAU | NMT 0.2% | BQL | BQL | BQL | BQL |
| Any unspecified degradation product | NMT 0.2% | BQL | 0.05 | BQL | BQL |
| Total Degradation products | NMT 1.5% | BQL | 0.05 | BQL | BQL |
| Water Content by Karl Fischer | NMT 4.0% | 1.9 | 1.4 | 1.4 | 1.5 |
| | Note Book Reference | 192031-8, 12, 14, 16, 17, 18 | | 192051-2 to 11 | 192099-157, 159, 167, 170 |

DOA: Date of analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea Table 22A depicts exemplary results for 130 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained below quantitation limit (0.05%).

TABLE 22A

| (130 mg/vial, up to 24 months) | | | | | |
|---|---|---|---|---|---|
| Product Name | Phenobarbital Sodium for Injection USP, 130 mg/vial | | Batch#NPH2021 Fill Volume: 1.05 mL | | Date Manufactured: Jan. 20, 2020 |
| Vial Make | | 2 mL Fiolax Clear Blow Back Vial | | | Date Initiated: Feb. 14, 2020 |
| | API Mfg. | | | Phenobarbital Sodium, USP Grade P, C-IV: | |
| Stopper Used | | 13 mm Grey Bromobutyl 2 leg Lyophilization Rubber stopper | | | Flip Off Seals: 13 mm Red Plastic top flip off with Aluminum Seal |
| Config-uration | Inverted | | Stability 25° C., | | 60% RH (RT) & 40° C., 75% RH (ACC) |
| | | | 1 Month DOA: Mar. 23, 2020 | 3 Months DOA: May 20, 2020 | 6 Months DOA: Sep. 4, 2020 | 24 Months DOA: 18 Mar. 2022 |
| | | Initial DOA: Feb. 18, | | | |

TABLE 22A-continued

| | | | | | | | | | |
|---|---|---|---|---|---|---|---|---|---|
| (130 mg/vial, up to 24 months) | | | | | | | | | |
| Test Description | Spec. WLP | 2020 WLP | RT WLP | ACC WLP | RT WLP | ACC WLP | RT WLP | ACC WLP | RT WLP |
| Appearance | CCS | CCS | CCS | CCS | CCS | CCS | CCS | CCS | CCS |
| pH (100 mg/mL) | 9.2-10.2 | 10.0 | 10.0 | 10.0 | 10.0 | 10.0 | 9.7 | 9.7 | 9.8 |
| % Assay Phenobarbital Sodium | 90.0%-105.0% | 100.3 | 99.7 | 99.3 | 100.0 | 99.6 | 99.1 | 98.3 | 99.8 |
| Related Substances 2EPMM | NMT 0.2% | BQL | ND | ND | ND | ND | ND | ND | ND |
| PBG | NMT 0.2% | ND | ND | ND | ND | ND | ND | ND | ND |
| PEAU | NMT 0.2% | BQL | BQL | BQL | BQL | BQL | BQL | BQL | BQL |
| Any unspecified degradation product | NMT 0.2% | BQL | BQL | BQL | BQL | BQL | BQL | BQL | BQL |
| Total degradation products | NMT 1.5% | BQL | BQL | BQL | BQL | BQL | BQL | BQL | BQL |
| Water Content by Karl Fischer | NMT 4.0% | 0.7 | 0.7 | 0.9 | 0.9 | 1.1 | 1.0 | 1.3 | 1.4 |
| Note Book Reference | | 192039-150 to 158 | 192045-23 to 45 | | 192045-135 to 151 | | 192051-84 to 122 | | 192099-157, 159, 167, 170 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea;

Table 22B depicts exemplary results for 200 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained near or below quantitation limit (0.05%).

TABLE 22B

| | | | | | | | |
|---|---|---|---|---|---|---|---|
| (200 mg/vial, up to 22 months) | | | | | | | |
| Product Name | | Phenobarbital Sodium for Injection USP, 200 mg/vial | | Batch#NPH2031A Fill Volume: 2.1 mL | | Date Manufactured: Jun. 3, 2020 | |
| Vial Make | | 10 mL Tubular Serum Bottle clear | | | Date Initiated: Jun. 9, 2020 | | |
| | API Mfg. | | | | Phenobarbital Sodium, USP Grade P, C-IV: | | |
| Stopper Used | | 20 mm Igloo Bromobutyl Lyophilization Rubber stopper | | | Flip Off Seals: 20 mm Red Plastic top flip off with Aluminum Seal | | |
| | | Configuration Inverted Stability 25° C., 60% RH (RT) & 40° C., 75% RH (ACC) | | | | | |
| | | | | 3 Months DOA: Sep. 4, 2020 | | 6 months DOA: Dec. 11, 2020 | 11 mouths DOA: 11 Apr. 2022 |
| Test | Spec. | Initial DOA: Jun. 5, 2020 | RT | ACC | RT | ACC | RT |
| Description | WLP | WLP | WLP | WLP | WLP | WLP | WLP |
| Appearance | CCS | CCS | CCS | CCS | CCS | CCS | CCS |
| pH (20 mg/mL) | 9.2-10.2 | 9.9 | 9.6 | 9.7 | 9.7 | 9.7 | 9.5 |
| % Assay Phenobarbital Sodium | 90.0-105.0 | 100.1 | 98.1 | 101.0 | 100.8 | 102.5 | 98.2 |

TABLE 22B-continued

| | | | | | | | |
|---|---|---|---|---|---|---|---|
| (200 mg/vial, up to 22 months) | | | | | | | |
| Related Substances (% Area) 2EPMM | NMT 0.2% | ND | ND | ND | ND | ND | ND |
| PBG | NMT 0.2% | ND | ND | ND | ND | ND | ND |
| PEAU | NMT 0.2% | BQL | BQL | BQL | BQL | BQL | BQL |
| Any unspecified degradation product @RRT 0.37 | NMT 0.2% | BQL | 0.06 | 0.05 | 0.06 | 0.05 | (BQL) |
| Total degradation products | NMT 1.5% | BQL | 0.06 | 0.05 | 0.06 | 0.05 | (BQL) |
| Water Content by Karl Fischer | NMT 3.0% | 1.1 | 1.0 | 1.3 | 1.2 | 1.6 | 1.5 |
| Note Book Reference | | 192045-163 to 189 | 192051-84 to 122 | | 192067-78 to 88 | | 192034-137 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: $\alpha$-Phenylbutyrylguanidine;
PEAU: Phenylethylacetylurea Table 23 depicts exemplary results for 200 mg per vial phenobarbital sodium stored at standard and accelerated conditions where under all tested conditions 2EPMM, PBG, and PEAU remained undetectable or below quantitation limit (0.05%). Likewise, unspecified degradation products and total degradation products remained near or below quantitation limit (0.05%). In contrast to Table 22, this formulation was filled into the vial using a 9% saline solution. The final concentration of the saline after reconstitution in 10 mL of water for injection will be 0.9%.

TABLE 23

| | | | | | | | |
|---|---|---|---|---|---|---|---|
| (200 mg/vial, up to 12 months) | | | | | | | |
| Product Name | Phenobarbital Sodium for Injection USP, 200 mg/vial (Phenobarbital Sodiumand 9% Saline/vial) | | Batch#NPH2031B Fill Volume: 2.1 mL | | Date Manufactured: Jun. 3, 2020 | | |
| Vial Make | 10 mL Tubular Serum Bottle clear API Mfg. | | | Date Initiated: Jun. 9, 2020 Phenobarbital Solution, USP Grade P, C-IV: | | | |
| Stopper Used | 20 mm Igloo Bromobutyl Lyophilization Rubber stopper | | | Flip Off Seals: 20 mm Red Plastic top flip off with Aluminum Seal | | | |
| Configuration | Inverted | | Stability 3 Months Initial | 25° C., 60% RH (RT) & 40° C., 75% RH (ACC) 6 Months | | | 12 months |
| Test | Spec. | Initial DOA: Jun. 5, 2020 | DOA: Sep. 4, 2020 RT | DOA: Dec. 11, 2020 ACC | RT | ACC | DOA: 11 Apr. 2022 RT |
| Description | WLP | WLP | WLP | WLP | WLP | WLP | WLP |
| Appearance | CCS | CCS | CCS | CCS | CCS | CCS | CCS |
| pH (20 mg/mL) | 9.2-10.2 | 9.8 | 9.5 | 9.5 | 9.6 | 9.6 | 9.5 |
| % Assay Phenobarbital Sodium | 90.0-105.0 | 103.3 | 102.8 | 103.6 | 104.0 | 103.7 | 99.9 |
| Related Substances (% Area) 2EPMM | NMT 0.2% | BQL | ND | ND | ND | ND | ND |
| PBG | NMT 0.2% | ND | ND | ND | ND | ND | ND |
| PEAU | NMT 0.2% | BQL | BQL | BQL | BQL | 0.05 | (BQL) |
| Any unspecified degradation product @RRT 0.37 | NMT 0.2% | BQL | 0.06 | 0.05 | 0.06 | 0.05 | (BQL) |
| Total degradation products | NMT 1.5% | BQL | 0.06 | 0.05 | 0.06 | 0.10 | BQL |

TABLE 23-continued

| (200 mg/vial, up to 12 months) | | | | | | | |
|---|---|---|---|---|---|---|---|
| Water Content by Karl Fischer | NMT 4.0% | 0.8 | 0.9 | 1.1 | NP | NP | 1.2 |
| Note Book Reference | | 192045-163 to 189 | 192051- 84 to 122 | | 192867-78 to 88 | | 192034-137 |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea To further investigate if the nature of the reconstitution solution would have an adverse effect on stability after reconstitution, the inventors used 65 mg of lyophilized amorphous phenobarbital in a vial and dissolved the lyophilized material with 0.9% or 5% dextrose to a final concentration of 1 mg/ml. In an additional set of experiments, the inventors used 130 mg of lyophilized amorphous phenobarbital in a vial and dissolved the lyophilized material with 0.9% or 5% dextrose or water to a final concentration of 20 mg/ml. The so reconstituted solutions were then kept under refrigeration (2-8° C.) or at standard conditions (25° C.) for the indicated times in the tables below. The levels of degradation were determined by quantifying the remaining phenobarbital and by quantifying 2-ethyl-2-phenylmalonamide (2EPMM), alpha-phenylbutyrylguanidine (PBG), and phenylethylacetylurea (PEAU), as well as other unspecified degradation products. Once more, under all tested conditions, the stability of the so reconstituted compositions was unexpectedly high.

Table 24 depicts exemplary results for 65 mg per vial phenobarbital sodium reconstituted with 5% dextrose to 1 mg/ml that was stored under refrigeration or at standard conditions. Under all tested conditions 2EPMM, PBG, and PEAU remained undetectable or below quantitation limit (0.05%). Likewise, unspecified degradation products and total degradation products remained near or below quantitation limit (0.05%).

TABLE 24

(65 mg/vial, reconstituted to 1 mg/ml in 5% dextrose, up to 24 hrs)
Admixture Study of Phenobarbital Sodium for Injection USP, 65 mg/vial (NPB2020) (1 mg/mL dilution in 5% Dextrose)

| Specifications | Tests | Initial | Time | | | | | | | | | | | |
|---|---|---|---|---|---|---|---|---|---|---|---|---|---|---|
| | | | 1 hr | | 2.5 hr | | 4 hrs | | 6 hrs | | 9 hrs | | 24 hrs | |
| | | | 2-8 C. | RT | 2-8 C. | RT | 2-8 C. | RT | 2-8 C. | RT | 2-8 C. | RT | 2-8 C. | RT |
| Complies | Appearance | CCS | CCS | CCS | CCS | CCS | CCS | CCS | CCS | CCS | CCS | CCS | CCS | CCS |
| pH To be reported | pH (1 mg/mL dilution) | 8.8 | 8.8 | 8.8 | 8.8 | 8.8 | 8.8 | 8.7 | 8.8 | 8.7 | 8.7 | 8.7 | 8.7 | 8.5 |
| Assay 90%-105% | Assay of Phenobarbital Sodium | 95.4 | 95.7 | 95.6 | 95.9 | 95.4 | 95.9 | 97.1 | 95.6 | 95.9 | 94.6 | 97.1 | 95.1 | 96.1 |
| 2EPMM NMT0.2% | Related Substances (% Area) 2EPMM | ND | ND | ND | ND | ND | ND | BQL | ND | ND | ND | BQL | ND | BQL |
| PEG NMT0.2% | PBG | ND | ND | ND | ND | ND | ND | ND | ND | ND | ND | ND | ND | ND |
| PEAU NMT0.2% | PEAU | ND | ND | BQL | BQL | BQL | ND | BQL | BQL | ND | BQL | BQL | BQL | BQL |
| Unspecified degradation product NMT 0.2% | Any unspecified degradation product @ RRT 0.29 | ND | ND | BDL | ND | BDL | ND | BDL | ND | 0.02 | BDL | 0.02 | BDL | 0.03 |
| | Any unspecified degradation product @ RRT 0.37 | 0.01 | 0.01 | 0.01 | 0.01 | 0.01 | 0.01 | 0.02 | 0.01 | 0.02 | 0.01 | 0.03 | 0.02 | 0.05 |
| Osmolality To be reported | Osmolality (mOsmol/Kg) | 254 | NP | Np | NP | NP | NP | NP | NP | NP | NP | NP | 255 | 253 |
| NMT 1.5% | Total degradation products | BQL | BQL | BQL | BQL | BQL | BQL | BQL | BQL | BQL | BQL | BQL | BQL | 0.08 |

CCS: Clear colorless solution;
ND: Not detected;
BDL: Below detection limit;
BQL: Below Quantitation limit;
NP: Not performed;
2EPMM: 2-ethylphenylmalonamide monohydrate;
PBG: Phenylbutyrylguanidine;
PEAU: Phenylethylacetylurea Table 25 depicts exemplary results for 65 mg per vial phenobarbital sodium reconstituted with 0.9% saline to 1 mg/ml that was stored under refrigeration or at standard conditions. Under all tested conditions 2EPMM, PBG, and PEAU remained undetectable or below quantitation limit (0.05%). Likewise, unspecified degradation products and total degradation products remained near or below quantitation limit (0.05%).

TABLE 25

(65 mg/vial, reconstituted to 1 mg/ml in 0.9% saline, up to 24 hrs)

Admixture study of Phenobarbital Sodium for Injection
USP, 65 mg/vial (NPH2020) (1 mg/mL) dilution in 0.9% Saline)

| | | | Time | | | | | | | | | | | |
| | | | 1 hr | | 2.5 hrs | | 4 hrs | | 6 hrs | | 9 hrs | | 24 hrs | |
| Specifications | Test | Initial | 2-8 C. | RT | 2-8 C. | RT | 2-8 C. | RT | 2-8 C. | RT | 2-8 C. | RT | 2-8 C. | RT |
|---|---|---|---|---|---|---|---|---|---|---|---|---|---|---|
| Complies | Description | CCS | CCS | CCS | CCS | CCS | CCS | CCS | CCS | CCS | CCS | CCS | CCS | CCS |
| pH<br>To be reported | pH (1 mg/mL dilution) | 9.0 | 8.8 | 8.9 | 9.0 | 9.0 | 8.9 | 8.9 | 8.9 | 8.9 | 8.7 | 8.8 | 8.5 | 8.4 |
| Assay<br>90%-105% | Assay of Phenobarbital Sodium | 95.8 | 96 | 94.3 | 95.4 | 93.6 | 95.5 | 95.2 | 95.8 | 93.9 | 94.6 | 96.4 | 95.2 | 95.3 |
| 2EPMM<br>NMT 0.2% | Related Substances (% Area) 2EPMM | ND | ND | ND | ND | ND | ND | BQL | ND | ND | ND | BQL | ND | BQL |
| PBG<br>NMT 0.2% | PBG | ND | ND | ND | ND | ND | ND | ND | ND | ND | ND | ND | ND | ND |
| PEAU<br>NMT 0.2% | PEAU | BQL | ND | BQL | BQL | BQL | BQL | BQL | BQL | ND | BQL | BQL | BQL | BQL |
| Unspecified degradation product<br>NMT 0.2% | Any unspecified degradation product @ RRT 0.29 | BDL | BDL | BDL | BDL | BDL | BDL | BDL | BDL | BDL | BDL | BDL | BDL | BDL |
| | Any unspecified degradation product @ RRT 0.037 | 0.02 | 0.02 | 0.03 | 0.02 | 0.03 | 0.02 | 0.04 | 0.02 | 0.04 | 0.03 | 0.05 | 0.03 | 0.1 |
| NMT 1.5% | Total degradation products | BQL | BQL | BQL | BQL | BQL | BQL | BQL | BQL | BQL | BQL | 0.05 | BQL | 0.1 |
| Osmolality<br>To be reported | Osmolality (mOsmol/Kg) | 288 | NP | NP | NP | NP | NP | NP | NP | NP | NP | NP | 286 | 287 |

CCS: Clear colorless solution;
ND: Not detected;
BQL: Below Quantitation limit;
NP: Not performed;
2EPMM: 2-ethylphenylmalonamide monohydrate;
PBG: Phenylbutyrylguanidine;
PEAU: Phenylethylacetylurea
BQL: Below Quantitation limit (0.05%)

Table 26 depicts exemplary results for 130 mg per vial phenobarbital sodium reconstituted with 0.9% saline to 20 mg/ml that was stored under refrigeration or at standard conditions. Under all tested conditions 2EPMM, PBG, and PEAU remained undetectable or below quantitation limit (0.05%). Likewise, unspecified degradation products and total degradation products remained near or below quantitation limit (0.05%).

TABLE 26

(130 mg/vial, reconstituted to 20 mg/ml in 0.9% saline, up to 24 hrs)
Admixture study of Phenobarbital Sodium for Injection USP,
130 mg/vial (NPH2030) (20 mg/mL dilution In 0.9% Saline)

| | | Time | | | | | |
| | | 30 min | | 90 min | | 240 min | |
| Tests | Initial | 2-8 C. | RT | 2-8 C. | RT | 2-8 C. | RT |
|---|---|---|---|---|---|---|---|
| Appearance | CCS | CCS | CCS | CCS | CCS | CCS | CCS |
| pH (20 mg/mL dilution) | 9.4 | 9.4 | 9.3 | 9.4 | 9.3 | 9.4 | 9.4 |
| Assay of Phenobarbital Sodium | 104.1 | 103.6 | 102.4 | 103.3 | 102.7 | 103.2 | 102.9 |
| Related Substances (% Area) 2EPMM | ND | ND | ND | ND | ND | ND | BQL |

TABLE 26-continued

| (130 mg/vial, reconstituted to 20 mg/ml in 0.9% saline, up to 24 hrs) Admixture study of Phenobarbital Sodium for Injection USP, 130 mg/vial (NPH2030) (20 mg/mL dilution In 0.9% Saline) | | | | | | | |
|---|---|---|---|---|---|---|---|
| PBG | ND | ND | ND | ND | ND | ND | ND |
| PEAU | BQL | BQL | BQL | BQL | BQL | BQL | BQL |
| Any unspecified degradation product @ RRT 0.37 | BQL | 0.03 | 0.04 | 0.03 | 0.05 | 0.03 | 0.07 |
| Total degradation products | BQL | 0.03 | 0.04 | 0.03 | 0.05 | 0.03 | 0.07 |
| Osmolality (mOsmol/Kg) | 418 | NP | NP | NP | NP | NP | NP |

|  | Time | | | | | |
|---|---|---|---|---|---|---|
|  | 6 hrs | | 9.5 hrs | | 24 hrs | |
| Tests | 2-8 C. | RT | 2-8 C. | RT | 2-8 C. | RT |
| Appearance | CCS | CCS | CCS | CCS | CCS | CCS |
| pH (20 mg/mL dilution) | 9.4 | 9.4 | 9.4 | 9.2 | 9.4 | 9.3 |
| Assay of Phenobarbital Sodium | 103.4 | 102.9 | 99.5 | 103.3 | 103.3 | 101.3 |
| Related Substances (% Area) 2EPMM | ND | BQL | ND | BQL | ND | BQL |
| PBG | ND | ND | ND | ND | ND | ND |
| PEAU | BQL | BQL | BQL | BQL | BQL | BQL |
| Any unspecified degradation product @ RRT 0.37 | 0.03 | 0.09 | 0.03 | 0.13 | 0.04 | 0.24 |
| Total degradation products | 0.03 | 0.09 | 0.03 | 0.13 | 0.04 | 0.24 |
| Osmolality (mOsmol/Kg) | NP | NP | 420 | 418 | 417 | 419 |

CCS: Clear colorless solution;
ND: Not detected;
BQL: Below Quantitation limit;
NP: Not performed;
2EPMM: 2-ethylphenylmalonamide monohydrate;
PBG: Phenylbutyrylguanidine;
PEAU: Phenylethylacetylurea Table 27 depicts exemplary results for 130 mg per vial phenobarbital sodium reconstituted with 5% dextrose to 20 mg/ml that was stored under refrigeration or at standard conditions. Under all tested conditions 2EPMM, PBG, and PEAU remained undetectable or below quantitation limit (0.05%). Likewise, unspecified degradation products and total degradation products remained near or below quantitation limit (0.05%).

TABLE 27

| (130 mg/vial, reconstituted to 20 mg/ml in 5% saline, up to 24 hrs) Admixture study of Phenobarbital Sodium for Injection USP, 130 mg/vial (NPH2030) (20 mg/mL dilution In 5% Dextrose) | | | | | | | |
|---|---|---|---|---|---|---|---|
|  |  | Time | | | | | |
|  |  | 30 min | | 90 min | | 4 hrs | |
| Test | Initial | 2-8 C. | RT | 2-8 C. | RT | 2-8 C. | RT |
| Appearance | CCS | CCS | CCS | CCS | CCS | CCS | CCS |
| pH (20 mg/mL dilution) | 9.4 | 9.4 | 9.3 | 9.4 | 9.4 | 9.4 | 9.3 |
| Assay of Phenobarbital Sodium | 101 | 102 | 100 | 101.5 | 102 | 100.9 | 101.1 |
| Related Substances (% Area) 2EPMM | ND | ND | ND | ND | ND | ND | BQL |
| PBG | ND | ND | ND | ND | ND | ND | ND |
| PEAU | BQL | BQL | BQL | BQL | BQL | BQL | BQL |
| Any unspecified degradation product @ RRT 0.37 | 0.02 | 0.02 | 0.03 | 0.03 | 0.04 | 0.03 | 0.06 |
| Total degradation products | 0.02 | 0.02 | 0.03 | 0.03 | 0.04 | 0.03 | 0.06 |
| Osmolality (mOsmol/Kg) | 379 | NP | NP | NP | NP | NP | NP |

TABLE 27-continued (130 mg/vial, reconstituted to 20 mg/ml in 5% saline, up to 24 hrs)
Admixture study of Phenobarbital Sodium for Injection USP,
130 mg/vial (NPH2030) (20 mg/mL dilution In 5% Dextrose)

| Test | Time | | | | | |
| | 6 hrs | | 9.5 hrs | | 14 hrs | |
| | 2-8 C. | RT | 2-8 C. | RT | 2-8 C. | RT |
| --- | --- | --- | --- | --- | --- | --- |
| Appearance | CCS | CCS | CCS | CCS | CCS | CCS |
| pH (20 mg/mL dilution) | 9.3 | 9.3 | 9.4 | 9.3 | 9.4 | 9.4 |
| Assay of Phenobarbital Sodium | 101.7 | 101.6 | 101.6 | 102.1 | 102.4 | 102.2 |
| Related Substances (% Area) 2EPMM | ND | ND | ND | BQL | ND | BQL |
| PBG | ND | ND | ND | ND | ND | ND |
| PEAU | BQL | BQL | BQL | BQL | BQL | BQL |
| Any unspecified degradation product @ RRT 0.37 | 0.03 | 0.08 | 0.03 | 0.11 | 0.04 | 0.19 |
| Total degradation products | 0.03 | 0.08 | 0.03 | 0.11 | 0.04 | 0.19 |
| Osmolality (mOsmol/Kg) | NP | NP | 379 | 380 | 377 | 379 |

CCS: Clear colorless solution;
ND: Not detected;
BQL: Below Quantitation limit;
NP: Not performed;
2EPMM: 2-ethylphenylmalonamide monohydrate;
PBG: Phenylbutyrylguanidine;
PEAU: Phenylethylacetylurea Table 28 depicts exemplary results for 130 mg per vial phenobarbital sodium reconstituted with water to 20 mg/ml that was stored under refrigeration or at standard conditions. Under all tested conditions 2EPMM, PBG, and PEAU remained undetectable or below quantitation limit (0.05%). Likewise, unspecified degradation products and total degradation products remained near or below quantitation limit (0.05%).

TABLE 28

(130 mg/vial, reconstituted to 20 mg/ml in water, up to 24 hrs)
Admixture study of Phenobarbital Sodium for Injection USP, 130 mg/vial (NPH2030)
(20 mg/mL dilution In Water)

| Tests | | Time | | | | | |
| | | 2 hrs | | 4 hrs | | 24 hrs | |
| | Initial | 2-8 C. | RT | 2-8 C. | RT | 2-8 C. | RT |
| --- | --- | --- | --- | --- | --- | --- | --- |
| Appearance | CCS | CCS | CCS | CCS | CCS | CCS | CCS |
| pH (20 mg/mL dilution) | 9.5 | 9.5 | 9.6 | 9.6 | 9.5 | 9.6 | 9.5 |
| Assay of Phenobarbital Sodium | 99.8 | 102.1 | 100.8 | 101.7 | 101.2 | 100.4 | 100.3 |
| Related Substances (% Area) 2EPMM | ND | ND | ND | ND | ND | ND | BQL |
| PBG | ND | ND | ND | ND | ND | ND | ND |
| PEAU | BQL | BQL | BQL | BQL | BQL | BQL | BQL |
| Any unspecified degradation product @ RRT 0.37 | 0.02 | 0.02 | 0.04 | 0.02 | 0.06 | 0.04 | 0.18 |
| Total degradation products | 0.02 | 0.02 | 0.04 | 0.02 | 0.06 | 0.04 | 0.18 |
| Osmolality mOsmol/Kg | 158 | NP | NP | NP | NP | 159 | 158 |

CCS: Clear colourless solution;

ND: Not detected;

BQL: Below Quantitation limit;

NP: Not performed;

2EPMM: 2-ethylphenylmalonamide monohydrate;

PBG: Phenylbutyrylguanidine;

PEAU: Phenylethylacetylurea

In further experiments, the inventors investigated if stable lyophilized phenobarbital preparations could be prepared (in crystalline and/or amorphous forms, depending on solvent) using one or more water miscible co-solvents. To that end, the inventors tested isopropanol, tert-butanol, ethanol, and acetonitrile as co-solvents. Most typically, the co-solvent(s) will be present in an amount of at least 1.0%, or at least 1.5%, or at least 2.0%, or at least 2.5%, or at least 3.0%, or at least 3.5%, or at least 4.0%, or at least 4.5%, or at least 5.0%, or at least 5.5%, or at least 6.0%, or at least 7.0%, or at least 8.0%, or at least 9.0%, or at least 10%, or at least 25%, or at least 50%, or at least 75%. Therefore, suitable quantities of co-solvent(s) include those between 1.0 and 3.0%, or between 2.5% and 5.0%, or between 3.0% and 7.5%, or between 5.0% and 10%, or between 10% and 25%, or between 25% and 50%, or between 50% and 75%, and even higher. For example, and as shown in more detail below, the concentration of the organic co-solvent was as high as 90%. Lyophilization conditions and results are shown below. Tables 29A and 29B depict formulation details used in the lyophilization and stability experiments. Two formulations were prepared for each strength (65 mg and 130 mg), one with 5% Isopropanol and the other with 5% Tertiary Butanol, and other co-solvents (here acetonitrile and ethanol) were also evaluated. The organic solvent was added after the Phenobarbital Sodium was dissolved in water, mixed well and adjusted to final volume with water. Later the bulk solution is filled in vials and lyophilized using the Lyo cycle parameters shown in Table 30. After the Lyo cycle was completed, the finished product was analyzed for assay, related substances, pH, moisture content and residual solvents.

TABLE 29A

| | | | | | Formulations with t-butanol and isopropanol as organic co-solvent | | |
|---|---|---|---|---|
| Ingredients | Bulk Solution | CAS Number | Concentration in mL | Total volume (50 mL) |
| Phenobarbital Sodium, USP C-IV | 65 mg/mL | NA | 65.73 mg (~65 mg Phenobarbital Sodium after LOD correction) | 3.287 g |
| | 130 mg/mL | | 131.469 mg (~130 mg Phenobarbital sodium after LOD correction) | 6.573 g |
| Tertiary Butanol | 5% | 75-65-0 | (0.05 ml or 0.039 g) | 2.5 ml or 1.95 g |
| Isopropanol | | 67-63-0 | (0.05 ml or 0.0393 g) | 2.5 ml or 1.963 g |
| DI Water/Water for Injection | N/A | | Q.S. to 1 mL | Q.S. to 50 mL |

TABLE 29B

| | | | |
|---|---|---|---|
| | | Formulations with ethanol and acetonitrile as organic co-solvent | |
| Ingredients | Bulk Solution Formulation prepared at 25° C. | Total Volume (100 mL Batch Size) | |
| | | NPH22035 | NPH22034 |
| Phenobarbital Sodium | 130 mg/mL | 13.38 g | 13.38 g |
| Ethanol | Qs | — | Qs to total volume 100 mL |
| Acetonitrile | Qs | Qs to total volume 100 mL | — |
| Water for Injection/ DI water | 10% | 10 ml | 10 ml |

TABLE 30

| | | | | |
|---|---|---|---|---|
| | | Lyophilization protocol | | |
| Section | Phase | Hold Time [mm] | Temperature ° C. | Vacuum [mTorr] |
| 1 | Loading | n.a. | 5 | off |
| 2 | Freezing | 5 | −5 | off |
| 3 | Freezing | 60 | −50 | off |
| 4 | Freezing | 30 | −10 | off |
| 5 | Freezing | 120 | −50 | off |
| 6 | Evacuation | 30 | −50 | 75 |
| 7 | Primary drying | 400 | −50 | 75 |
| 8 | Primary drying | 350 | −45 | 75 |
| 9 | Primary drying | 300 | −43 | 75 |
| 10 | Primary drying | 250 | −35 | 75 |
| 11 | Primary drying | 60 | −20 | 75 |
| 12 | Primary drying | 120 | 0 | 75 |
| 13 | Secondary drying | 120 | 50 | 75 |
| 14 | Secondary drying | 120 | 25 | 75 |

Table 31 depicts results for 65 mg and 130 mg per vial phenobarbital sodium (from a bulk solution containing 5% tert-butanol) stored at standard and accelerated conditions where under all tested conditions 2EPMM, PBG, and PEAU remained undetectable or below quantitation limit (0.05%). Likewise, unspecified degradation products and total degradation products remained near or below quantitation limit (0.05%).

TABLE 31

(65/130 mg/vial, 5% tert-butanol, up to 3 months)
Product Name Phenobarbital Sodium for Injection, USP Lyophilized Powder. Bulk solution
prepared in 5% Tertiary Butanol Date Manufactured: Feb. 21, 2019 Date Initiated: Sep. 5, 2019
Configuration Inverted Stability 25° C., 60% RH (RT) & 40° C., 75% RH (ACC)

| | | NPH1965 (65 mg/vial) | | | NPH1967 (130 mg/vial) | | |
| | | | 3 Months DOA: Dec. 20, 2019 | | | 3 Months DOA: Dec. 20, 2019 | |
| | | Initial | | | Initial | | |
| Test | Spec. | DOA: Sep. 7, 2019 | RT | ACC | DOA: Dec. 20, 2019 | RT | ACC |
|---|---|---|---|---|---|---|---|
| Description | WLP | WLP | WLP | WLP | WLP | WLP | WLP |
| Appearance | CCS | CCS | CCS | CCS | CCS | CCS | CCS |
| pH (65 mg/mL) | 9.2-10.2 | 9.7 | 9.7 | 9.7 | 9.8 | 9.8 | 9.8 |
| pH (100 mg/mL) for 130 mg/vial strength | | | | | | | |
| % Assay Phenobarbital Sodium | 90.0%-105% | 98.2 | 98.8 | 97.7 | 100.0 | 99.9 | 99.9 |
| Related Substances 2EPMM | NMT 0.2% | ND | ND | ND | ND | ND | ND |
| PBG | NMT 0.2% | ND | ND | ND | ND | ND | ND |
| PEAU | NMT 0.2% | BQL | BQL | BQL | BQL | BQL | BQL |
| Any other degradation product | NMT 0.2% | 0.09 | BQL | BQL | 0.09 | BQL | BQL |
| Total degradation products | NMT 1.5% | 0.09 | BQL | BQL | BQL | BQL | BQL |
| Water Content by Karl Fischer | NMT 4.0% | 0.4 | NT | NP | 0.3 | NP | NP |
| % Residual Solvent (Tertiary butanol) | To be reported | 1.2 | 0.6 | 0.8 | 4.4 | 2.9 | 1.7 |
| Note Book Reference | | 192031-46 to 52 | 192039-9 to 23 | | 192031-46 to 52 | 192039-9 to 23 | |

LP: White Lyophilized Powder;
CCS: Clear Colorless Solution, 1 minute after reconstitution;
DOA: Date of analysis
ND: Not Detected;
NP: Not performed;
NMT: Not More Than;
BQL: Below Quantitation Limit (0.05%)
2EPMM: 2-Ethyl-2-Phenylmalonamide, monohydrate;
PBG: α-Phenylbutylguanidine;
PEAU: Phenylethylacetylurea Table 32 depicts results for 65 mg and 130 mg per vial phenobarbital sodium (from a bulk solution containing 5% isopropanol) stored at standard and accelerated conditions where under all tested conditions 2EPMM, PBG, and PEAU remained undetectable or below quantitation limit (0.05%). Likewise, unspecified degradation products and total degradation products remained near or below quantitation limit (0.05).

TABLE 32

(65/130 mg/vial, 5% isopropanol, up to 3 months)
Product Name Phenobarbital Sodium for Injection, USP Lyophilized Powder. Bulk solution
prepared in 5% Isopropanol Date Manufactured: Feb. 21, 2019 Date Initiated: Sep. 5, 2019
Configuration Inverted Stability 25° C., 60% RH (RT) & 40° C., 75% RH (ACC)

| | | NPH1966 (65 mg/vial) | | | NPH1968 (130 mg/vial) | | |
| | | | 3 Months DOA: Dec. 20, 2019 | | | 3 Months DOA: Dec. 29, 2019 | |
| | | Initial | | | Initial | | |
| Test | Spec. | DOA: Sep. 7, 2019 | RT | ACC | DOA: Sep. 7, 2019 | RT | ACC |
|---|---|---|---|---|---|---|---|
| Description | WLP | WLP | WLP | WLP | WLP | WLP | WLP |
| Appearance | CCS | CCS | CCS | CCS | CCS | CCS | CCS |
| pH (65 mg/mL) | 9.2-10.2 | 9.6 | 9.6 | 9.7 | 9.8 | 9.7 | 9.7 |
| pH (100 mg/mL) for 130 mg/vial strength | | | | | | | |
| % Assay Phenobarbital Sodium | 90.0%-105% | 99.7 | 98.8 | 100.0 | 100.0 | 101.1 | 99.1 |
| Related Substances 2EPMM | NMT 0.2% | ND | ND | ND | ND | ND | ND |
| PBG | NMT 0.2% | ND | ND | ND | ND | ND | ND |
| PEAU | NMT 0.2% | BQL | BQL | BQL | BQL | BQL | BQL |
| Any other degradation product | NMT 0.2% | 0.08 | BQL | BQL | 0.09 | BQL | BQL |
| Total degradation products | NMT 1.5% | 0.08 | BQL | BQL | BQL | BQL | BQL |
| Water Content by Karl Fischer | NMT 4.0% | 0.3 | NP | NP | 0.3 | NP | NP |

TABLE 32-continued (65/130 mg/vial, 5% isopropanol, up to 3 months)
Product Name Phenobarbital Sodium for Injection, USP Lyophilized Powder. Bulk solution
prepared in 5% Isopropanol Date Manufactured: Feb. 21, 2019 Date Initiated: Sep. 5, 2019
Configuration Inverted Stability 25° C., 60% RH (RT) & 40° C., 75% RH (ACC)

| | | NPH1966 (65 mg/vial) | | | NPH1968 (130 mg/vial) | | |
| | | | 3 Months DOA: Dec. 20, 2019 | | | 3 Months DOA: Dec. 29, 2019 | |
| | | Initial | | | Initial | | |
| Test | Spec. | DOA: Sep. 7, 2019 | RT | ACC | DOA: Sep. 7, 2019 | RT | ACC |
|------|-------|-------|----|-----|-------|----|-----|
| % Residual Solvent (Isopropanol) | To be reported | 1.7 | 0.7 | 0.7 | 1.7 | 1.4 | 1.4 |
| Note Book Reference | | 192031-46 to 52 | 192039-9 to 23 | | 192031-46 to 52 | 192039-9 to 23 | |

WLP: White Lyophilized Powder;
CCS: Clear Colorless Solution, 1 minute after reconstitution;
DOA: Date of analysis
ND: Not Detected;
NP: Not performed;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea Table 33 depicts initial results for 65 mg and 130 mg per vial lyophilized phenobarbital sodium from respective bulk solutions containing ethanol or acetonitrile as co-solvent (to obtain 65 mg/vial, 0.5 mL of the bulk solution was filled in the vials and for 130 mg/vial strength, 1 ml of the bulk solution was filled in the vials prior to lyophilization). For all test products, 2EPMM, PBG, and PEAU remained undetectable or below quantitation limit (0.05%). Notably, unspecified degradation products and total degradation products also remained undetectable or below quantitation limit (0.05%).

TABLE 33

(65/130 mg/vial, acetonitrile or ethanol as co-solvents)

| | | Initial NPH22035 Formulation in Acetonitrile:Water | | Initial NPH22834 Formulation in Ethanol:Water | |
| Test | Spec. | 65 mg Fill volume (0.5 mL) | 130 mg Fill Volume (1 mL) | 65 mg Fill volume (0.5 mL) | 130 mg Fill Volume (1 mL) |
|------|-------|------|------|------|------|
| Description | WLP | WLP | WLP | WLP | WLP |
| Appearance | CCS | CCS | CCS | CCS | CCS |
| pH (65 mg/mL) | 9.2-10.2 | NA | NA | NA | NA |
| % Assay Phenobarbital Sodium | 90.0%-105.0% | 103.6 | 101.2 | 100.2 | 98.3 |
| Related Substances 2EPMM | NMT 0.2% | ND | ND | ND | ND |
| PBG | NMT 0.2% | ND | ND | ND | ND |
| PEAU | NMT 0.2% | BQL | BQL | BQL | BQL |
| Any unspecified degradation product | NMT 0.2% | ND | ND | ND | ND |
| Total degradation products | NMT 1.5% | BQL | BQL | BQL | BQL |
| Water Content by Karl Fischer | NMT 3.0% | 0.4 | 0.4 | 0.2 | 0.2 |
| Residual Solvent | To be reported | NA | NA | 3.2 | 19.2 |

WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea
NA: Not available Notably, the results indicated that the above formulations were also storage stable over at least three months as evidenced by all known impurities below quantitation limit as shown in Tables 31 and 32. However, an unknown impurity was observed above LOQ level. Interestingly, the residual solvents tertiary butanol and isopropanol were not completely removed after the first cycle of secondary drying. Tertiary butanol and isopropanol were observed above 0.5% in the 65 mg and 130 mg strength products. The same vials were then subjected to additional secondary drying at 25° C. for 30 min and 50° C. for 120 min, and the samples were analyzed for residual solvent after the second cycle of secondary drying.

After the additional secondary drying steps, residual tert-butanol and isopropanol were observed at lower quantities, respectively. As can be readily seen, the organic solvents could be reduced in quantities, but were not completely removed, possibly suggesting that the tested organic solvents could form a bond in the crystal lattice of phenobarbital. However, further process modifications may possibly result in additional reduction of residual co-solvent, requiring extensive experimentation. Similar formulations were prepared in organic solvents ethanol and acetonitrile. Here as well, the residual solvent ethanol was not completely removed, but further process modifications may possibly result in additional reduction of residual co-solvent, requiring extensive experimentation.

Organic solvents such as isopropanol, tertiary butanol, ethanol and acetonitrile were investigated as co-solvents during the lyophilization. Two co solvents tertiary butanol and Isopropanol were used as co-solvents at 5%. The 3M stability data for the formulation with IPA and tert-butanol indicates that although no known degradation products were observed above quantitation limit, the residual solvents could not be removed completely after lyophilization. When ethanol was used as a co solvent similar results were observed. In view of the fact that organic solvents are toxic to all age groups, and in particular to neonates and because residual solvents are typically trapped in the crystal lattice of the Phenobarbital, the lyophilized product with only water as solvent is preferred over formulations containing any organic co solvents.

X-Ray Powder Diffraction. With reference to FIGS. 5A-5D, XRPD was performed using the Rigaku Smart-Lab X-ray diffraction system configured for reflection Bragg-Brentano geometry using a line source X-ray beam. The X-ray source is a Cu Long Fine Focus tube that was operated at 40 kV and 44 mA. That source provides an incident beam profile at the sample that changes from a narrow line at high angles to a broad rectangle at low angles. Beam conditioning slits were used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths. The samples were placed in a low-background, silicon holder using light manual pressure to keep the sample surfaces flat and level with the reference surface of the holder. The samples were analyzed from 2 to 40° 2θ using a continuous scan of 6° 2θ per minute with an effective step size of 0.02° 2θ.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A pharmaceutical product, comprising:
a container enclosing sterile storage stable lyophilized amorphous phenobarbital;
wherein the lyophilized phenobarbital is storage stable such that, upon storage at 25° C. and 60% relative humidity for 3 months and reconstitution with water to a concentration of 65 mg/mL, less than 0.05% of degradation products from the phenobarbital are detectable in the reconstituted solution;
wherein the degradation products are selected form the group consisting of 2-ethyl-2-phenylmalonamide (2EPMM), alpha-phenylbutyrylguanidine (PBG), and phenylethylacetylurea (PEAU); and
wherein the lyophilized phenobarbital is stored under vacuum in the container.

2. The product of claim 1, wherein no more than 0.05% total degradation products, including 2EPMM, PBG, and PEAU, are detectable in the reconstituted solution.

3. The product of claim 1, wherein the lyophilized amorphous phenobarbital contains no more than 1.8% water.

4. The product of claim 1, wherein the lyophilized amorphous phenobarbital contains no more than 1.5% water.

5. The product of claim 1, wherein at least 90% of total lyophilized phenobarbital is amorphous phenobarbital.

6. The product of claim 1, wherein the lyophilized amorphous phenobarbital is storage stable such that, upon storage at 25° C. and 60% relative humidity for 6 months and reconstitution with water, less than 0.05% of degradation products from the phenobarbital are detectable in the reconstituted solution.

7. The product of claim 6, wherein no more than 0.05% total degradation products, including 2EPMM, PBG, and PEAU, are detectable in the reconstituted solution.

8. The product of claim 1, wherein the container contains 65 mg of the sterile storage stable lyophilized amorphous phenobarbital.

9. The product of claim 1, wherein the container contains 130 mg of the sterile storage stable lyophilized amorphous phenobarbital.

10. The product of claim 1, wherein the container contains 65-200 mg of the sterile storage stable lyophilized amorphous phenobarbital.

11. The product of claim 1, wherein the lyophilized amorphous phenobarbital is storage stable such that, upon storage at 40° C. and 75% relative humidity for 3 months and reconstitution with water, less than 0.05% of degradation products from the phenobarbital are detectable in the reconstituted solution.

12. The product of claim 11, wherein no more than 0.1% total degradation products, including 2EPMM, PBG, and PEAU, are detectable in the reconstituted solution.

13. The product of claim 1, wherein the lyophilized amorphous phenobarbital is storage stable such that, upon storage at 40° C. and 75% relative humidity for 6 months and reconstitution with water, less than 0.05% of degradation products from the phenobarbital are detectable in the reconstituted solution.

14. A method of preparing a phenobarbital solution in an aqueous carrier, comprising:

reconstituting the pharmaceutical product of claim 1 in the container in an aqueous carrier to produce a clear colorless solution comprising the phenobarbital;

wherein the clear colorless solution comprises, upon reconstitution to a concentration of 65 mg/mL, initial quantities of degradation products from the phenobarbital in an amount of less than 0.05%; and wherein the degradation products are selected form the group consisting of 2-ethyl-2-phenylmalonamide (2EPMM), alpha-phenylbutyrylguanidine (PBG), and phenylethylacetylurea (PEAU).

15. The method of claim 14, wherein the clear colorless solution comprises, upon reconstitution, initial quantities of total degradation products, including 2EPMM, PBG, and PEAU, in an amount of no more than 0.05%.

16. The method of claim 14, wherein the aqueous carrier is water for injection, a 0.9% saline solution, or a 5% dextrose solution.

17. The method of claim 14, wherein the clear colorless solution comprises the phenobarbital at a concentration of 20 mg/mL.

18. The method of claim 14, wherein the clear colorless solution contains, upon storage for 20 hours at 25° C. and 60% relative humidity, less than 0.05% of degradation products from the phenobarbital.

19. The method of claim 18, wherein the clear colorless solution contains, upon storage for 20 hours at 25° C. and 60% relative humidity, no more than 0.3% total degradation products, including 2EPMM, PBG, and PEAU.

20. The method of claim 16, wherein the clear colorless solution has, upon reconstitution, an initial pH of between 9.5 and 9.9.

\* \* \* \* \*